(12) United States Patent
Ostertag et al.

(10) Patent No.: US 8,722,964 B2
(45) Date of Patent: May 13, 2014

(54) GENETICALLY ENGINEERED OR TRANSGENIC RATS EXHIBITING A CANCER PHENOTYPE DUE TO A DISRUPTION OF GERMLINE TUMOR SUPPRESSOR GENES

(75) Inventors: Eric M. Ostertag, Lexington, KY (US); John Stuart Crawford, Lexington, KY (US)

(73) Assignee: Transposagen Biopharmaceuticals, Inc., Lexington, KY (US)

( * ) Notice: Subject to any disclaimer, the term of this patent is extended or adjusted under 35 U.S.C. 154(b) by 182 days.

(21) Appl. No.: 12/766,284

(22) Filed: Apr. 23, 2010

(65) Prior Publication Data

US 2010/0287628 A1  Nov. 11, 2010

Related U.S. Application Data

(60) Provisional application No. 61/172,016, filed on Apr. 23, 2009.

(51) Int. Cl.
  *C12N 15/00* (2006.01)
  *A01K 67/027* (2006.01)
  *C12N 15/85* (2006.01)

(52) U.S. Cl.
  CPC ....... *A01K 67/0278* (2013.01); *A01K 2217/075* (2013.01); *A01K 2217/203* (2013.01); *C12N 15/85* (2013.01); *C12N 2015/8527* (2013.01); *C12N 2015/8536* (2013.01); *C12N 2015/8572* (2013.01)
  USPC ....... 800/10; 800/3; 800/14; 800/25; 435/463

(58) Field of Classification Search
  CPC ............... C12N 15/85; C12N 15/8527; C12N 15/8536; C12N 15/8572; A01K 2217/075; A01K 2217/203
  See application file for complete search history.

(56) References Cited

U.S. PATENT DOCUMENTS

| | | | |
|---|---|---|---|
| 4,670,388 A | 6/1987 | Rubin et al. | |
| 4,736,866 A | 4/1988 | Leder et al. | |
| 4,870,009 A | 9/1989 | Evans et al. | |
| 4,873,191 A | 10/1989 | Wagner et al. | |
| 4,897,355 A | 1/1990 | Eppstein et al. | |
| 4,945,050 A | 7/1990 | Sanford et al. | |
| 4,949,317 A | 8/1990 | McQuitty et al. | |
| 5,489,742 A | 2/1996 | Hammer et al. | |
| 5,569,824 A * | 10/1996 | Donehower et al. ............ 800/10 |
| 5,654,182 A | 8/1997 | Wahl et al. | |
| 5,719,055 A | 2/1998 | Cooper | |
| 5,792,924 A | 8/1998 | Yoder et al. | |
| 6,207,876 B1 | 3/2001 | Kellems et al. | |
| 6,218,185 B1 | 4/2001 | Shirk et al. | |
| 6,225,121 B1 | 5/2001 | Savakis et al. | |
| 6,432,639 B1 | 8/2002 | Lichter et al. | |
| 6,475,798 B2 | 11/2002 | Fogarty et al. | |
| 6,489,458 B2 | 12/2002 | Hackett et al. | |
| 6,962,810 B2 | 11/2005 | Fraser et al. | |
| 6,989,441 B2 | 1/2006 | Curtis | |
| 7,148,203 B2 | 12/2006 | Hackett et al. | |
| 7,223,557 B2 | 5/2007 | Lee et al. | |
| 7,262,336 B2 | 8/2007 | Young et al. | |
| 7,504,223 B2 | 3/2009 | Srivastava et al. | |
| 7,985,739 B2 | 7/2011 | Kay et al. | |
| 7,998,993 B2 | 8/2011 | Perner et al. | |
| 8,084,616 B2 | 12/2011 | Gomtsyan et al. | |
| 8,137,907 B2 | 3/2012 | Zender et al. | |
| 8,558,055 B2 | 10/2013 | Ostertag et al. | |
| 2002/0016975 A1 | 2/2002 | Hackett et al. | |
| 2002/0028513 A1 | 3/2002 | Fogarty et al. | |
| 2002/0072101 A1 | 6/2002 | Gaughan et al. | |
| 2002/0088017 A1 | 7/2002 | Kellems et al. | |
| 2003/0049728 A1 | 3/2003 | Julius et al. | |
| 2004/0025197 A1 | 2/2004 | Young et al. | |
| 2006/0026699 A1 | 2/2006 | Largaespada et al. | |
| 2006/0194750 A1 | 8/2006 | Shuster et al. | |
| 2007/0022486 A1 | 1/2007 | Allen | |
| 2007/0209083 A1 | 9/2007 | Thiam et al. | |
| 2009/0131302 A1 | 5/2009 | Pasricha et al. | |
| 2011/0035816 A1 | 2/2011 | Ostertag et al. | |
| 2011/0145936 A1 | 6/2011 | Ostertag et al. | |
| 2012/0151609 A1 | 6/2012 | Ostertag et al. | |
| 2012/0177577 A1 | 7/2012 | Ostertag et al. | |

FOREIGN PATENT DOCUMENTS

| | | |
|---|---|---|
| JP | 2006 141228 | 6/2006 |
| WO | WO 97/07668 | 3/1997 |
| WO | WO 97/07669 | 3/1997 |
| WO | WO 00/15650 | 3/2000 |
| WO | WO 02/44210 A2 | 6/2002 |
| WO | WO 2005/020683 | 3/2005 |

(Continued)

OTHER PUBLICATIONS

Collier et al. Cancer gene discovery in solid tumours using transposon-based somatic mutagenesis in the mouse .Nature, 2005, vol. 436, pp. 272-276.*
Kitada et al. Transposon-tagged mutagenesis in the rat. Nature Methods, 2007, vol. 4, pp. 131-133.*
van Boxel et al. Homozygous and heterozygous p53 knockout rats develop metastasizing sarcomas with high frequency. American J Pathol, 2011, vol. 179, pp. 1616-1622.*
Yeung et al. Susceptibility to renal carcinoma in the Eker rat involves a tumor suppressor gene on chromosome. PNAS, 1993, vol. 90, pp. 8038-8042.*
Kobayashi et al. A germline insertion in the tuberous sclerosis (Tsc2) gene gives rise to the Eker rat model of dominantly inherited cancer. Nature Genetics, 1995, vol. 9. pp. 70-74.*

(Continued)

*Primary Examiner* — Deborah Crouch
(74) *Attorney, Agent, or Firm* — Frost Brown Todd LLC

(57) ABSTRACT

This invention relates to the engineering of animal cells, preferably mammalian, more preferably rat, that are deficient due to the disruption of tumor suppressor gene(s) or gene product(s). In another aspect, the invention relates to genetically modified rats, as well as the descendants and ancestors of such animals, which are animal models of human cancer and methods of their use.

34 Claims, 4 Drawing Sheets

(56) References Cited

FOREIGN PATENT DOCUMENTS

| | | |
|---|---|---|
| WO | WO 2005/053512 A2 | 6/2005 |
| WO | WO 2007/053637 A2 | 5/2007 |
| WO | WO 2008/015403 A1 | 2/2008 |
| WO | WO 2009/037707 A2 | 3/2009 |
| WO | WO 2009/050484 | 4/2009 |
| WO | WO 2009/055629 A2 | 4/2009 |
| WO | WO 2009/055749 A1 | 4/2009 |
| WO | WO 2009/061152 A2 | 5/2009 |
| WO | WO 2009/071334 | 6/2009 |
| WO | WO 2009/072882 | 6/2009 |
| WO | WO 2009/084034 A2 | 7/2009 |
| WO | WO 2010/124200 A2 | 10/2010 |
| WO | WO 2011/014721 | 2/2011 |
| WO | WO 2011/022634 A2 | 2/2011 |

OTHER PUBLICATIONS

Kuff et al. Intracisternal A-particle genes as movable elements in the mouse genome. PNAS, 1983, vol. 80, pp. 1992-1996.*
Acsadi, G. et al., "Human dystrophin expression in mdx mice after intramuscular injection of DNA constructs," Nature, vol. 352, (1991) pp. 815-818.
Bagshawe, K.D., "A cytotoxic agent can be generated selectively at cancer sites," Br. J. Cancer, vol. 58 (1988) pp. 700-703.
Bagshawe, K.D., "Towards generating cytotoxic agents at cancer sites," Br. J. Cancer, vol. 60 (1989) pp. 275-281.
Battelli et al., "T lymphocyte killing by a xanthine-oxidase-containing immunotoxin," Cancer Immunol. Immunother., vol. 35 (1992) pp. 421-425.
Berghammer, A.J. et al., "A Universal Marker for Genetically Modified Insects," Nature, vol. 402 (1999) pp. 370-371.
Bessereau, J.L. et al., "Mobilization of a Drosophila transposon in the Caenorhabditis elegans germ line," Nature, vol. 413 (Sep. 2001) pp. 70-74.
Bhasin, A. et al., Characterization of a Tn5 pre-cleavage synaptic complex, J. Mol. Biol., vol. 302 (2000) pp. 49-63.
Brigham et al., "Expression of a Prokaryotic Gene in Cultured Lung Endothelial Cells after Lipofection with a Plasmid Vector," Am. J. Resp. Cell. Mol. Biol, vol. 1 (1989) pp. 95-100.
Brinster, R.L. et al., "Factors Affecting the Efficiency of Introducing Foreign DNA into Mice by Microinjecting Eggs," Proc. Nat. Acad. Sci. USA, vol. 82(13) (1985) pp. 4438-4442.
Brown, V. I. et al., "Molecular and Cellular Mechanisms of Receptor-Mediated Endocytosis," DNA and Cell Biology, vol. 10(6) (1991) pp. 399-409.
Burres, V. et al., "The ICESt1 element of Streptococcus thermophilus belongs to a large family of integrative and conjugative elements that exchange modules and change their specificity of integration," Plasmid, vol. 48(2) (2002) pp. 77-97.
Capecchi, M.R., "Altering the Genome by Homologous Recombination," Science, vol. 244(4910) (1989) pp. 1288-1292.
Cheng, Q. et al., "Specificity determinants for bacteriophage Hong Kong 022 integrase: analysis of mutants with relaxed core-binding specificities," Mol. Microbiol., vol. 36(2) (2000) pp. 424-436.
Claesson, M.H. et al, "Antibodies Directed Against Monomorphic and Evolutionary Conserved Self Epitopes may be Generated in 'Knock-Out' Mice. Development of Monoclonal Antibodies Directed Against Monomorphic MHC Class I Determinants," Scan. J. Immunol., vol. 40 (1994) pp. 257-254.
Cui, Z. et al., "Structure-Function Analysis of the Inverted Terminal Repeats of the Sleeping Beauty Transposon," J. Mol. Biol., vol. 318 (2002) pp. 1221-1235.
Declerck, P.J. et al, "Generation of Monoclonal Antibodies against Autologous Proteins in Gene-inactivated Mice," J. Biol. Chem., vol. 270(15) (1995) pp. 8397-8400.
Felgner, P.L. et al, "Lipofection: A Highly Efficient, Lipid-Mediated DNA-Transfection Procedure" Proc. Natl. Acad. Sci. USA, vol. 84(21) (1987) pp. 7413-7417.

Franz, G. et al, "Minos, a new transposable element from Drosophila hydei, is a member of the Tc1-like family of transposons," Nucl. Acids Res., vol. 19(23) (1991) p. 6646.
Hammer, R.E. et al, "Spontaneous Inflammatory Disease in Transgenic Rats Expressing HLA-B27 and Human $\beta_2$m: An Animal Model of HLA-B27-Associated Human Disorders," Cell, vol. 63 (1990) pp. 1099-1112.
Hickman, A.B. et al., "Molecular organization in site-specific recombination: The catalytic domain of bacteriophage HP1 integrase at 2.7 A resolution," Cell, vol. 89 (1997) pp. 227-237.
Houdebine, L.M. et al., "Transgenesis in fish," Experientia, vol. 47 (1991) pp. 891-897.
Hughes, B.J. et al., "Monoclonal Antibody Targeting of Liposomes to Mouse Lung in Vivo," Cancer Research, vol. 49 (1989) pp. 6214-6220.
Ivics, Z. et al., "Identification of functional domains and evolution of Tc1-like I transposable elements," Proc. Natl. Acad. Sci. USA, vol. 93(10) (1996) pp. 5008-5013.
Izsvak, Z. et al., "Characterization of a Tc1-like transposable element in zebrafish (Dario rerio)," Mol. Gen. Genet., vol. 247 (1995) pp. 312-322.
Izsvak, Z. et al., "Sleeping Beauty, a wide host-range transposon vector for genetic transformation in vertebrates," J. Mol. Biol., vol. 302 (2000) pp. 93-102.
Jakobovits, A., "Humanizing the mouse genome," Curr. Biol., vol. 4(8) (1994) pp. 761-763.
Joyner, A.L., et al., "Production of a mutation in mouse En-2 gene by homologous recombination in embryonic stem cells," Nature, vol. 338 (1989) pp. 153-156.
Ke, Z. et al, "Quetzal: a transposon of the Tc1 family in the mosquito Anolpheles albimanus," Genetica, vol. 98 (1996) pp. 141-147.
Kinsey, J.A., "Tad, a LINE-Like Transposable Element of Neurospora, Can Transpose Between Nuclei in Heterokaryons," Genetics, vol. 126 (Oct. 1990) pp. 317-323.
Kuduvalli, P.N. et al, "Target DNA structure plays a critical role in Tn7 transposition." EMBO J., vol. 20(4) (2001) pp, 924-932.
Lakso, M. et al., "Targeted Oncogene Activation by Site-Specific Recombination in Transgenic Mice,"PNAS, vol. 89(14) (1992).pp. 6232-6236.
Lam, W.L. et al., "Discovery of amphibian Tc1-like transposon families," J. Mol. Biol., vol. 257 (1996) pp. 359-366.
Lampe, D.J. et al, "Factors affecting transposition of the Himar1 Mariner transposon in vitro," Genetics, vol. 149(1) (1998) pp. 179-187.
Li, Y. et al, "The P1 plasmid in action: time-lapse photomicroscopy reveals some unexpected aspects of plasmid partition," Plasmid, vol. 48(3) (2002) pp. 174-178.
Lin S., "Transgenic Zebrafish," Methods Mol. Bio., vol. 136 (2000) pp. 375-383.
Litzinger, D.C. et al., "Biodistribution and immunotargetability of ganglioside-stabilized dioleoylphosphatidylethanolamine liposomes," Biochimica et Biophysica Acta, vol. 1104 (1992) pp. 179-187.
Luan, D.D. et al., "Reverse Transcription of R2Bm RNA IS Primed by a Nick at the Chromosomal Target Site: A Mechanism for Non-LTR Retrotransposition," Cell, vol. 72 (1993) pp. 595-605.
Luan, D.D. et al, "RNA Template Requirements for Target DNA-Primed Reverse Transcription by the R2 Retrotransposable Element," Mol. Cell Biol., vol. 15(7) (1995) pp. 3882-3891.
Marra, D. et al., "Regulation of excision of the conjugative transposon," Mol. Microbiol, vol. 31(2) (1999) pp. 609-621.
Merriman, P.J. et al., "S elements: a family of Tc1-like transposons in the genome of Drosolphila melanogaster," Genetics, vol. 141 (1995) pp. 1425-1438.
Nunes-Duby, S.E. et al, "Similarities and differences among 105 members of the Int family of site-specific recombinases," Nuc. Acids Res., vol. 26(2) (1998) pp. 391-406.
O'Gorman, S. et al., "Recombinase-Mediated Gene Activation and Site-Specific Integration in Mammalian Cells," Science, vol. 251(4999) (1991) pp. 1351-1355.
Pietersz, G.A. et al., "Antibody Conjugates for the Treatment of Cancer," Immunolog. Reviews, vol. 129 (1992) pp. 57-80.

(56) References Cited

OTHER PUBLICATIONS

Pursel, V.G. et al., "Genetic Engineering of Livestock," Science, vol. 244(4910) (1989) pp. 1281-1288.

Rezende, L.F. et al., "Essential Amino Acid Residues in the Single-stranded DNA-binding Protein of Bacteriophage T7, Identification of the Dimer Interface," J. Biol. Chem., vol. 277(52) (2002) pp. 50643-50653.

Roffler, S. et al., "Anti-neoplastic glucuronide prodrug treatment of human tumor cells targeted with a monoclonal antibody-enzyme conjugate," Biochem. Pharmacol., vol. 42(10) (1991) pp. 2062-2065.

Rubin, G.M. et al., "Genetic Transformation of *Drosophila* with Transposable Element Vectors," Science, vol. 218(4570) (1982) pp. 348-353.

Rubin, G.M. et al., "Vectors for P element mediated gene transfer in *Drosophila*," Nucleic Acids Res., vol. 11(18) (1983) pp. 6341-6351.

Senter, P.D. et al, "Generation of 5-Fluorouracil from 5-Fluorocytosine by Monoclonal Antibody-Cytosine Deaminase Conjugates," Bioconjugate Chem., vol. 2 (1991) pp. 447-451.

Senter, P.D. et al., "Generation of Cytotoxic Agents by Targeted Enzymes," Bioconjugate Chem., vol. 4 (1993) pp. 3-9.

Shoemaker, N. B. et al., "The Bacteroides mobilizable insertion element, NBU1, integrates into the 3' end of a Leu-tRNA gene and has an integrase that is a member of the lambda integrase family," J. Bacteriol., vol. 178(12) (1996) pp. 3594-3600.

Sun, X. et al, "Conditional inactivation of Fgf4 reveals complexity of signaling during limb bud development," Nat. Genet., vol. 25 (2000) pp. 83-86.

The Gene Ontology Consortium, "Gene Ontology: tool for the unification of biology," Nature Genetics, vol. 25 (May. 2000) pp. 25-29.

Toshiki, T. et al., "Germline transformation of the silkworm *Bombyx mori* L. using a piggyback transposon-derived vector," Nat. Biotechnol., vol. 18 (1) (Jan. 2000) pp. 81-84.

Tu, Z. et al., "Intra- and inter-specific diversity of Tc-3 like transposons in nematodes and insects and implications for their evolution and transposition," Gene, vol. 282 (2002) pp. 133-142.

Wilmut, I. et al, "Viable offspring derived from fetal and adult mammalian cells," Nature, vol. 385 (1997) pp. 810-813.

Wolff, J.A. et al., "Direct Gene Transfer into Mouse Muscle in Vivo," Science, vol. 247(4949) (1990) pp. 1465-1468.

Zhang, L. et al., "DNA-binding activity and subunit interaction of the mariner transposase," Nucleic Acids Res., vol. 29(17) (2001) pp. 3566-3575.

Amos-Landgraf, et al. A target-selected Apc-mutant rat kindred enhances the modeling of familial human colon cancer, Proc Natl Acad Sci USA 2007, 104:4036-4041.

Chang, et al. Tumourigenesis associated with the p53 tumour suppressor gene, Br J Cancer 1993, 68:653-661.

Charreau, et al. Transgenesis in rats: technical aspects and models, Transgenic Research, 1996, pp. 223-234, vol. 5.

Clarke, AR. Murine models of neoplasia: functional analysis of the tumour suppressor genes Rb-1 and p53, Cancer Metastasis Rev 1995, 14:125-148.

Corpet, et al. How good are rodent models of carcinogenesis in predicting efficacy in humans? A systematic review and meta-analysis of colon chemoprevention in rats, mice and men, European Journal of Cancer, Sep. 2005, pp. 1911-1922, vol. 41, Issue 13.

Cotroneo, et al. Characterizing a rat Brca2 knockout model, Oncogene 2007, 26:1626-1635.

Donehower,et al. Mice deficient for p53 are developmentally normal but susceptible to spontaneous tumours, Nature, Mar. 19, 1992, pp. 215-221, vol. 356.

Dong et al. B7-H1, a third member of the B7 family, co-stimulates T-cell proliferation and interleukin-10 secretion, Nature Medicine, Dec. 1999, p. 1365-1369, vol. 5, No. 12.

Geurts, et al. Knockout rats via embryo microinjection of zinc-finger nucleases, Science 2009, 325:433.

Harvey, et al. Spontaneous and carcinogen-induced tumorigenesis in p53-deficient mice, Nat Genet 1993, 5:225-229.

Hollstein, et al. p53 mutations in human cancers, Science 1991, 253:49-53.

Huang, et al. Beyond knockout rats: new insights into finer genome manipulation in rats, Cell Cyde 2011, 10:1059-1066.

Jacks, et al Tumor spectrum analysis in p53-mutant mice, Current Biology, 1994, pp. 1-7, vol. 4, No. 1.

Jacob, HJ. Functional genomics and rat models, Genome Res 1999, 9:1013-1016.

Karray et al. Complete Loss of *Fas Ligand* Gene Causes Massive Lymphoproliferation and Early Death, Indicating a Risdual Activity of *gld* Allele, The Journal of Immunology, 2004, pp. 2118-2125, vol. 172.

Kitada, et al. Transposon-tagged mutagenesis in the rat, Nature Methods, Feb. 2007, pp. 131-133, vol. 4, No. 2.

Krug, et al. Tumor suppressor genes in normal and malignant hematopoiesis, Oncogene 2002, 21:3475-3495.

Kullberg, et al *Helicobacter hepaticus*-Induced Colitis in Interleukin-10-Deficient Mice: Cytokine Requirements for the Induction and Maintenance of Intestinal Inflammation, Infection and Immunity, Jul. 2001, pp. 4232-4241, vol. 69, No. 7.

Kullberg, et al. *Helicobacter hepaticus* Triggers Colitis in Specific-Pathogen-Free Interleukin-10 (IL-10)-Deficient Mice through an IL-12- and Gamma Interferon-Dependent Mechanism, Infection and Immunity, Nov. 1998, pp. 5157-5166, vol. 66, No. 11.

Lindblad-Toh, Kerstin, Three's company: Publication of the rat genome sequence will not only advance physiological studies in this paragon of laboratory animals, but also greatly enhance the power of comparative research into mammalian genomes, Nature, Apr. 1, 2004, pp. 475-476, vol. 428.

Malkin, et al. Germ line p53 mutations in a familial syndrome of breast cancer, sarcomas, and other neoplasms, Science 1990, 250:1233-1238.

Nakagama, et al. Modeling human colon cancer in rodents using a food-borne carcinogen, PhIP, Cancer Science, Oct. 2005, pp. 627-639, vol. 96, No. 10.

Nandi, et al. Hormones and mammary carcinogenesis in mice, rats, and humans: A unifying hypothesis, PNAS, Apr. 1995, pp. 3650-3657, vol. 92.

Nobuyuki, et al. A new colon and mammary carcinogen in cooked food, 2-amino-1-methyl-6-phenylimidazo[4,5-*b*]pyridine (PhIP), Carcinogenesis, 1991, pp. 1503-1506, vol. 12, No. 8.

Nordlinger, et al. Experimental model of colon cancer: Recurrences after surgery alone or associated with intraperitoneal 5-fluorouracil chemotherapy, Diseases of the Colon & Rectum, Aug. 1991, pp. 658-663, vol. 34.

Preudhomme, et al. Very low incidence of p53 antibodies in adult non-Hodgkin's lymphoma and multiple myeloma, Br J Haematol 1998, 100:184-186.

Purdie, et al. Tumour incidence, spectrum and ploidy in mice with a large deletion in the p53 gene, Oncogene 1994, 9:603-609 [Abstract Only].

Riley, et al. Transcriptional control of human p53-regulated genes, Natl Rev Mol Cell Biol 2008, 9:402-412.

Russo, et al. Comparative study of human and rat mammary tumorigenesis, Lab Invest, Mar. 1990 pp. 244-278, vol. 62(3) [Title Only].

Smits, et al. Generation of gene knockouts and mutant models in the laboratory rat by ENU-driven target-selected mutagenesis, Pharmacogenet Genomics 2006, 16:159-169.

Smits, et al. Genetically Engineered Rat Models for Breast Cancer, Breast Disease, 2007, pp. 53-61, vol. 28.

Son, et al. Orofile of early occurring spontaneous tumors in Han Wistar rats, Toxicol Pathol 2010, 38:292-296.

Tong, et al. Production of p53 gene knockout rats by homologous recombination in embryonic stem cells, Nature 2010, 467:211-213.

Tsubura, et al, Animal Models of N-Methyl-N-nitrosourea-induced Mammary Cancer and Retinal Degeneration with Special Emphasis on Therapeutic Trials, in vivo, Jan.-Feb. 2011, pp. 11-22, vol. 25, No. 1 [Abstract Only].

Van Boxtel, et al. ENU mutagenesis to generate genetically modified rat models, Methods Mol Biol 2010, 597:151-167 [Abstract Only].

Van Boxtel, et al. Improved generation of rat gene knockouts by target-selected mutagenesis in mismatch repair-deficient animals, BMC Genomics 2008, 9:460.

(56) References Cited

OTHER PUBLICATIONS

Van Boxtel, et al. Lack of DNA mismatch repair protein MSH6 in the rat results in hereditary non-polyposis colorectal cancer-like tumorigenesis, Carcinogenesis 2008, 29:1290-1297.

Van Boxtel, et al. Rat traps: filling the toolbox for manipulating the rat genome, Genome Biol 2010, 11:217.

Wang, et al. Difference in the Response of *neu* and *ras* Oncogene-induced Rat Mammary Carcinomas to Early and Late Ovariectomy, Cancer Research, Aug. 1, 1992, pp. 4102-4105, vol. 52.

Zan, et al. Production of knockout rats using ENU mutagenesis and a yeast-based screening assay, Nat Biotechnol 2003, 21:645-651.

Aitman, T. J., et al, Progress and prospects in rat genetics: a community view, Nature Genetics, May 2008, pp. 516-522, vol. 40, No. 5.

Geurts, A.M., et al, Generation of gene-specific mutated rats using zinc-finger nucleases, Rat Genomics: Methods of Molecular Biology, 2010, pp. 211-225, vol. 597 (Abstract only).

Jacob, H.J., et al, Gene Targeting in the Rat: Advances and Opportunities, Trends Genet., Dec. 2010, pp. 510-518, vol. 26(12).

Jacob, H.J., et al, Rat genetics: attaching physiology and pharmacology to the genome, Nature Reviews|Genetics, Jan. 2002, pp. 33-42, vol. 3.

Lu, B. Generation of rat mutants using a coat color-tagged Sleeping Beauty transposon system, Mamm Genome, 2007, pp. 338-346, vol. 18.

Mashimo, T, et al., Generation of knockout rats with X-linked severe combined immunodeficiency (X-SCID) using zinc-finger nucleases, PLoS One, Jan. 2010, pp. e8870 (1-7), vol. 5, Issue 1.

Anonymous, Gene Cyp7b1Tn(sb-T2/Bart3)2.306Mcwi, Tar Genome Database, http://rgd.mcw.edu/tools/genes/genes_view.cgi?id=2303974 (Mar. 3, 2003).

Anonymous, "Strain F344-Cyp7b1Tn(sb-T2/Bart3)2.306Mcwi," Rat Genome Database, http://rgd.mcw.edu/tools/strains/strains_view.cgi?id=2303976 (Mar. 3, 2009).

Asamoto, M. et al., "Connexin 32 Dominant-Negative Mutant Transgenic Rats are Resistant to Hepatic Damage by Chemicals," Hepatology, Jul. 1, 2004, pp. 205-210, vol. 40(1).

Baghdasaryan, A., et al. "Role of hepatic phospholipids in development of liver injury in *Mdr2* (*Abcb4*) knockout mice," Liver International, Aug. 2008, pp. 948-958, vol. 28, Issue 7 (Abstract only).

Baisong, L. et a l., "Generation of rat mutants using a coat color-tagged *Sleeping Beauty* transposon system," Mammalian Genome, Jun. 2007, pp. 338-346, vol. 18, No. 5.

Blackburn et al. "Adenosine Deaminase-deficient Mice Generated Using a Two-stage Genetic Engineering Strategy Exhibit a Combined Immunodeficiency," The Journal of Biological Chemistry, Feb. 27, 1998, pp. 5093-5100, vol. 273, No. 9, The American Society for Biochemistry and Molecular Biology, Inc.

Blackburn et al. "Adenosine mediates IL-13-induced inflammation and remodeling in the lung and interacts in an IL-13-adenosine amplification pathway," The Journal of Clinical Investigation, Aug. 2003, pp. 332-344, vol. 112, No. 3.

Blackburn et al., "Disruption of the adenosine deaminase gene causes hepatocellular impairment and perinatal lethality in mice," Proc. Natl. Acad. Sci. USA, Apr. 1995, pp. 3673-3677, vol. 92.

Breedveld, P. et al., "The Effect of Bcrpl (Abcg2) on the In vivo Pharmacokinetics and Brain Penetration of Imatinib Mesylate (Gleevec): Implications for the Use of Breast Cancer Resistance Protein and P-Glycoprotein Inhibitors to enable the Brain Penetration of Imatinib in Patients," Cancer Research, 2005, pp. 2577-2582, vol. 65(7).

Bucheton et al. "The Molecular Basis of I-R Hybrid Dysgenesis in *Drosophila melanogaster*: Identification, Cloning, and Properties of the I Factor," Cell, 1984, pp. 153-163, vol. 38, Issue 1.

Buehr, M., et al. "Capture of Authentic Embryonic Stem Cells from Rat Blastocysts," Cell, Dec. 26, 2008, pp. 1287-1298, vol. 135, No. 7, Elsevier Inc.

Chen, Y.-L., et al., "Nocistatin and nociceptin exert opposite effects on the excitability of central amygdale nucleus-periaquedactal gray projection neurons," Molecular and Cellular Neuroscience, 2009, pp. 76-88, vol. 40.

Clark, J., et al, "A future for transgenic livestock," Nature Reviews, Oct. 2003, pp. 825-833, vol. 4.

Elg, S. et al., "Cellular Subtype Distribution and Developmental Regulation of TRCP Channel Members in the Mouse Dorsal Root Ganglion," The Journal of Comparative Neurology, 2007, pp. 35-46, vol. 503, Wiley-Liss, Inc.

Fields, M.L. et al., "The Influence of Effector T Cells and Fas Ligand on Lupus-Associated B Cells," The Journal of Immunology, Jul. 1, 2005, pp. 104-111, vol. 175(1).

Freichel, M. et al, "Lack of an endothelial store-operated $Ca^{2+}$ current impairs agonist-dependent vasorelaxation in TRP4−/− mice," Nature Cell Biology, Feb. 2001, pp. 121-127, vol. 3.

Gene Targeting, A Practical Approach, IRL Press at Oxford University Press (1993).

Geurts, A.M., et al, "Conditional gene expression in the mouse using a *Sleeping Beauty* gene-trap transposon," BioMed Central Biotechnology, 2006, pp. 1-15, vol. 6:30.

Ghebranious, N. et al, "The Mouse Equivalent of the Human p53ser249 Mutation p53ser246 Enhances Aflatoxin Hepatocarcinogenesis in Hepatitis B Surface Antigen Transgenic and p53 Heterozygous Null Mice," Hepatology, Dec. 2003, pp. 967-973, vol. 27, Issue 4.

Gonzalez, F.J., "Role of cytochromes P450 in chemical toxicity and oxidative stress: Studies with CYP2E1," Mutation Research, Jan. 6, 2005, pp. 101-110, vol. 569 (1-2).

Halestrap, A.P. et al, "The SLC16 gene family—from monocarboxylate.transporters (MCTs) to aromatic amino acid transporters and beyond," European Journal of Physiol., 2004, pp. 619-628, vol. 447.

Hogan, B., Manipulating the Mouse Embryo, Cold Spring Harbor Laboratory Press, Cold Spring Harbor, N.Y., (1986).

Homberg, J.R. et al., "Complete Knockout of the Nociceptin/Orphanin FQ Receptor in the Rat Does Not Induce Compensatory Changes in μ, δ and κ Opioid Receptors," Neuroscience, 2009, pp. 308-315, vol. 163.

Hu, H.-Z., et al., "2-Aminoethoxydiphenyl Borate Is a common Activator of TRPV1, TRPV2, and TRPV3*," The Journal of Biological Chemistry, Aug. 20, 2004, pp. 35741-35748, vol. 279, No. 34, The American Society for Biochemistry and Molecular Biology, Inc.

Justice, M. J., et al, "Mouse ENU Mutagenesis," Human Molecular Genetics, 1999, pp. 1955-1963, vol. 8, No. 10.

Kage, K. et al., "Dominant-negative inhibition of breast cancer resistance protein as drug efflux pump through the inhibition of S-S dependent homodimerization," International Journal of Cancer, Feb. 10, 2002, pp. 626-630, vol. 97(5).

Keng, V.W., et at, "Region-specific saturation germline mutagenesis in mice using the *Sleeping Beauty* tranposon system," Nature Methods, Oct. 2005, pp. 763-769, vol. 2, No. 10.

Kitada, K. et al "Generating mutant rats using the Sleeping Beauty transposon system," Methods: A Companion to Methods in Enzymology, 2009, pp. 236-242, vol. 49, Academic Press Inc., New York, NY, US.

Kley, N.J. et al., "A Universal Marker for Transgenic Insects," Nature, Nov. 25, 1999, pp. 370-371, vol. 402, Macmillan Magazines Ltd.

Kloeckener-Gruissem, B., et al. "Mutation of Solute Carrier SLC16A12 Associates with Syndrome Combining Juvenile Cataract with Microcornea and Renal Glucosuria," The American Journal of Human Genetics, Mar. 2008, pp. 772-779, vol. 82.

Kogan, G L, et al, "The GATE retrotransposon in *Drosophila melanogaster*: mobility in heterochromatin and aspects of its expression in germ line tissues," Molecular Genetics and Genomics, Mar. 14, 2003, pp. 234-242, vol. 269, No. 2.

Lam, P. et al., "Bile Acid Transport in Sister of P-Glycoprotein (ABCB11) Knockout Mice," Biochemistry, 2005, pp. 12598-12605, vol. 44(37).

Lee, S.S.T. et al., "Role of CYP2E1 in the Hepatotoxicity of Acetaminophen," J. Biol. Chem., 1996, pp. 1-16, vol. 271(20).

Lewerenz, J., et al, "Basal Levels of elF2α Phosphorylation Determine Cellular Antioxidant Status by Regulating ATF4 and xCT Expression," The Journal of Biological Chemistry, Jan. 9, 2009, pp. 1106-1115, vol. 284 No. 2.

(56) References Cited

OTHER PUBLICATIONS

Li, P., et al, "Germline Competent Embryonic Stem Cells Derived from Rat Blastocysts," Cell, Dec. 2008, pp. 1299-1310, vol. 135, Issue 7.
Liang, H.C.L. et al., "Cypla2(−/−) null mutant mice develop normally but show deficient drug metabolism," PNAS, Feb. 1996, pp. 1671-1676, vol. 93.
Li-Hawkins, J. et al., "Disruption of the oxysterol 7alpha-hydroxylase gene in mice," Journal of Biological Chemistry, Jun. 2, 2000, pp. 16536-16542, vol. 275(22).
Liu, R. et al, "Cystine-Glutamate Transporter SLC7A11 Mediates Resistance to Geldanamycin but Not to 17-(Allylamino)-17-demethoxygeldanamycin," Molecular Pharmacology, 2007, pp. 1637-1646, vol. 72, No. 6.
Lorico, A. et al., "Disruption of the Murine MRP (Multidrug Resistance Protein) Gene Leads to Increased Sensitivity to Etoposide (VP-16) and Increased Levels of Glutathione," Cancer Research, 1997, pp. 5238-5242, vol. 57.
Martin, C. et al., "CYP7B Generates a Selective Estrogen Receptor β Agonist in Human Prostrate," The Journal of Clinical Endocrinology & Metabolism, 2004, pp. 2928-2935, vol. 89(6).
Masui, Norio, et al. "Establishment of a Set of Combined Immunodeficient DA/S1c-Foxn1rnu Lystbg Congenic Rat Strains," Experimental Animals (Tokyo), 2004, pp. 399-407, vol. 53, No. 5.
McDorman, K.S. et al. "Use of the Spontaneous Tsc2 Knockout (Eker) Rat Model of hereditary Renal Cell Carcinoma for the Study of Renal Carcinogens," Toxicologic Pathology, 2002, pp. 675-680, vol. 30, No. 6.
Mizuno, N. et al., "Impact of drug transporter studies on drug discovery and development," Pharmacological Reviews, Sep. 2003, pp. 425-461, vol. 55(3) (Abstract only).
Nagata, S. "Human autoimmune lymphoproliferative syndrome, a defect in the apoptosis-inducing Fas receptor: A lesson from the mouse model," J. Hum. Genet., 1998, pp. 2-8, vol. 43.
Omoto, Y., et al., "Early onset of puberty and early ovarian failure in CYP7B1 knockout mice," PNAS, Feb. 22, 2005, pp. 2814-2819, vol. 102, No. 8.
O'Sullivan, G.J., et al, "Potential and limitations of genetic manipulation in animals," Durg Discovery Today: Technologies, 2006, vol. 3, No. 2, pp. 173-180.
Phillips, M.S., et al, "Leptin receptor missense mutation in the *fatty* Zucker rat," Nature Genetics, May 1996, pp. 18-19, vol. 13.
Phys Gen Knockout: "Strain Report for F344-Faslg Tn sb-T2/Bart 3) 2.325MCwi" (May 11, 2009) http://rgd.mcw.edu/tools/strains/strains_view.cgi?Submit=View+Strain&id=2306875.
Rinehart, E.K., et al, "Neuropeptidergic characterization of the leptin receptor mutated obese Koletsky rat," Regulatory Peptides, 2004, pp. 3-10, vol. 119.
Robertson, E. J., Teratocarcinomas and Embryonic Stem Cells, A Practical Approach, ed., IRL Press (1987).
Rohacs, T., et al,. "Phospholipase C mediated modulation of TRPV1 Channels," Mol Neurobiol, 2008, pp. 153-163, vol. 37.
Rose, K. et al., "Neurosteroid Hydroxylase CYP7B," The Journal of Biological Chemistry, Jun. 29, 2001, pp. 23937-23944, vol. 276(26).
Ryding, A.D.S., et al. "Conditional transgenic technologies," Journal of Endocrinology, 2001, pp. 1-14, vol. 171.
Sato,H. et al., "Redox Imbalance in Cystine/Glutamate Transporter-deficient Mice," The Journal of Biological Chemistry, Nov. 11, 2005, pp. 37423-37429, vol. 280, No. 45.
Schneider, E. et al., "Organic cation transporter 3 modulates murine basophil functions by controlling intracellular histamine levels," J. Exp. Med., Aug. 1, 2005, pp. 387-393, vol. 202, No. 3.
Schwarz, M., "Pathways and defects of bile acid synthesis: insights from in vitro and in vivo experimental models," Drug Discovery Today: Disease Models, Dec. 17, 2004, pp. 205-212, vol. 1(3).
Sen, B., et al. "The transcriptional profile of the kidney in *Tsc2* heterozygous mutant Long Evans (Eker) rats compared to wild-type," Mutation Research/Fundamental and Molecular Mechanisms of Mutagenesis, May 2004, pp. 213-224, vol. 549, Issues1-2 (Abstract only).
Setchell, K.D.R. et al., "Identification of a New Inborn Error in Bile Acid Synthesis: Mutation of the Oxysterol 7α-Hydroxylase Gene Causes Severe Neonatal Liver Disease," J. Clin. Invest., Nov. 1998, pp. 1690-1703, vol. 102, No. 9.
Simons, J.P. et al., "Gene Transfer into Sheep," Nature Biotechnology, Feb. 1988, pp. 179-183, vol. 6.
Smits, B.M.G. et al., "Rat genetics: the next episode," Trends in Genetics, Apr. 2006, pp. 232-240, vol 22(4).
Sparreboom, A. et al., "Limited oral bioavailability and active epithelial excretion of paclitaxel (Taxol) caused by P-glycoprotein in the intestine," PNAS, Mar. 1997, pp. 2031-2035, vol. 94.
Stemmer, K. et al. "Carcinogen-Specific Gene Expression Profiles in Short-term Treated Eker and Wild-type Rats Indicative of Pathways Involved in Renal Tumorigenesis," Cancer Cancer Research, 2007, pp. 4052-4068, vol. 67.
Szakacs, G. et al., "The role of ABC transporters in drug absorption, distribution, metabolism, excretion and toxicity (ADME-Tox)," Drug Discovery Today, May 1, 2008, pp. 279-393, vol. 13(9-10) (Abstract only).
Van Boxtel, R. et al, "Rat Reverse Genetics: Generation and Characterization of Chmically Induced Rat Mutants," Copyright 2010, pp. 1-82 (XP-002681613).
Van Boxtel, R., et al, "Systematic generation of in vivo G protein-coupled receptor mutants in the rat," The Pharmacogenomics Journal, 2011 pp. 326-336, vol. 11.
Van Herwaarden, A.E. et al., "Knockout of cytochrome P450 3A yields new mouse models for understanding xenobiotic metabolism," The Journal of Clinical Investigation, Nov. 2007, pp. 3583-3592, vol. 117(11).
Watanabe, H., et al., "The Pathological Role of Transient Receptor Potential Channels in Heart Disease," Circulation Journal, Mar. 2009, pp. 419-427, vol. 73.
Wissenbach, U., et al., "TRP channels as potential drug targets," Science Direct, Biology of the Cell, Dec. 2003, pp. 47-54, vol. 96.
Wolff, J. A., et al. "Human dystrophin expression in mdx mice after intramuscular injection of DNA constructs," Nature, Aug. 29, 1991, pp. 815-818, vol. 352.
Written Opinion dated Nov. 11, 2010 for Application No. PCT/US2010/040768.
Written Opinion dated Oct. 23, 2011 for Application No. PCT/US2010/032222.
Written Opinion dated Jan. 24, 2012 for Application No. PCT/US2010/043043.
Written Opinion dated Jan. 30, 2012 for Application No. PCT/US2010/043817.
Written Opinion dated Feb. 5, 2012 for Application No. PCT/US2010/044545.
Written Opinion dated Feb. 20, 2012 for Application No. PCT/US2010/046144.
Written Opinion dated Aug. 29, 2012 for Application No. PCT/US2012/029736.
Yant, S., et al. "Somatic integration and long-term transgene expression in normal and haemophilic mice using a DNA transposon system," Nature Genetics, May 2000, pp. 35-41, vol. 25.
Zhang, Y. et al., "In vitro and in vivo models for assessing drug efflux transporter activity," Advanced Drug Delivery reviews, Jan. 21, 2003, pp. 31-51, vol. 55(1) (Abstract only).

* cited by examiner

Breeding and Screening

FIG 3

Sequences encoding the transposases for the DNA transposons *Sleeping Beauty* and *PiggyBac*:

SB Transposase:
ATGGGAAAATCAAAAGAAATCAGCCAAGACCTCAGAAAAAAAATTGTAGACCTCCACAAGTCTGGTTCATCCTTGGGAGCAATTT
CCAAACGCCTGAAAGTACCACGTTCATCTGTACAAACAATAGTACGCAAGTATAAACACCATGGGACCACGCAGCCGTCATACCG
CTCAGGAAGGAGACGCGTTCTGTCTCCTAGAGATGAACGTACTTTGGTGCGAAAAGTGCAAATCAATCCCAGAACAACAGCAAA
GGACCTTGTGAAGATGCTGGAGGAAACAGGTACAAAAGTATCTATATCCACAGTAAAACGAGTCCTATATCGACATAACCTGAAA
GGCCGCTCAGCAAGGAAGAAGCCACTGCTCCAAAACCGACATAAGAAAGCCAGACTACGGTTTGCAACTGCACATGGGGACAAA
GATCGTACTTTTTGGAGAAATGTCCTCTGGTCTGATGAAACAAAAATAGAACTGTTTGGCCATAATGACCATCGTTATGTTTGGAG
GAAGAAGGGGGAGGCTTGCAAGCCGAAGAACACCATCCCAACCGTGAAGCACGGGGGTGGCAGCATCATGTTGTGGGGGTGCTT
TGCTGCAGGAGGGACTGGTGCACTTCACAAAATAGATGGCATCATGAGGAAGGAAAATTATGTGGATATATTGAAGCAACATCTC
AAGACATCAGTCAGGAAGTTAAAGCTTGGTCGCAAATGGGTCTTCCAAATGGACAATGACCCCAAGCATACTTCCAAAGTTGTGG
CAAAATGGCTTAAGGACAACAAAGTCAAGGTATTGGAGTGGCCATCACAAAGCCCTGACCTCAATCCTATAGAAAATTTGTGGGC
AGAACTGAAAAAGCGTGTGCGAGCAAGGAGGCCTACAAACCTGACTCAGTTACACCAGCTCTGTCAGGAGGAATGGGCCAAAAT
TCACCCAACTTATTGTGGGAAGCTTGTGGAAGGCTACCCGAAACGTTTGACCCAAGTTAAACAATTTAAAGGCAATGCTACCAAA
TACTAG SB 5' ITR:
CAGTTGAAGTCGGAAGTTTACATACACTTAAGTTGGAGTCATTAAAACTCGTTTTTCAACTACTCCACAAATTTCTTGTTAACAAA
CAATAGTTTTGGCAAGTCAGTTAGGACATCTACTTTGTGCATGACACAAGTCATTTTTCCAACAATTGTTTACAGACAGATTATTTC
ACTTATAATTCACTGTATCACAATTCCAGTGGGTCAGAAGTTTACATACACTAAGT SB 3' ITR:
ATTGAGTGTATGTAAACTTCTGACCCACTGGGAATGTGATGAAAGAAATAAAAGCTGAAATGAATCATTCTCTCTACTATTATTCT
GATATTTCACATTCTTAAAATAAAGTGGTGATCCTAACTGACCTAAGACAGGGAATTTTTACTAGGATTAAATGTCAGGAATTGTG
AAAAAGTGAGTTTAAATGTATTTGGCTAAGGTGTATGTAAACTTCCGACTTCAACTG PB Transposase:
ATGGGTAGTTCTTTAGACGATGAGCATATCCTCTCTGCTCTTCTGCAAAGCGATGACGAGCTTGTTGGTGAGGATTCTGACAGTGA
AATATCAGATCACGTAAGTGAAGATGACGTCCAGAGCGATACAGAAGAAGCGTTTATAGATGAGGTACATGAAGTGCAGCCAAC
GTCAAGCGGTAGTGAAATATTAGACGAACAAAATGTTATTGAACAACCAGGTTCTTCATTGGCTTCTAACAGAATCTTGACCTTGC
CACAGAGGACTATTAGAGGTAAGAATAAACATTGTTGGTCAACTTCAAAGTCCACGAGGCGTAGCCGAGTCTCTGCACTGAACAT
TGTCAGATCTCAAAGAGGTCCGACGCGTATGTGCCGCAATATATATGACCCACTTTTATGCTTCAAACTATTTTTTACTGATGAGA
TAATTTCGGAAATTGTAAAATGGACAAATGCTGAGATATCATTGAAACGTCGGGAATCTATGACAGGTGCTACATTTCGTGACAC
GAATGAAGATGAAATCTATGCTTTCTTTGGTATTCTGGTAATGACAGCAGTGAGAAAAGATAACCACATGTCCACAGATGACCTC
TTTGATCGATCTTTGTCAATGGTGTACGTCTCTGTAATGAGTCGTGATCGTTTTGATTTTTTGATACGATGTCTTAGAATGGATGAC
AAAAGTATACGGCCCACACTTCGAGAAAACGATGTATTTACTCCTGTTAGAAAAATATGGGATCTCTTTATCCATCAGTGCATACA
AAATTACACTCCAGGGGCTCATTTGACCATAGATGAACAGTTACTTGGTTTTAGAGGACGGTGTCCGTTTAGGATGTATATCCCAA
ACAAGCCAAGTAAGTATGGAATAAAAATCCTCATGATGTGTGACAGTGGTACGAAGTATATGATAAATGGAATGCCTTATTTGGG
AAGAGGAACACAGACCAACGGAGTACCACTCGGTGAATACTACGTGAAGGAGTTATCAAAGCCTGTGCACGGTAGTTGTCGTAA
TATTACGTGTGACAATTGGTTCACCTCAATCCCTTTGGCAAAAAACTTACTACAAGAACCGTATAAGTTAACCATTGTGGGAACCG
TGCGATCAAACAAACGCGAGATACCGGAAGTACTGAAAAACAGTCGCTCCAGGCCAGTGGGAACATCGATGTTTGTTTTGACGG
ACCCCTTACTCTCGTCTCATATAAACCGAAGCCAGCTAAGATGGTATACTTATTATCATCTTGTGATGAGGATGCTTCTATCAACG
AAAGTACCGGTAAACCGCAAATGGTTATGTATTATAATCAAACTAAAGGCGGAGTGGACACGCTAGACCAAATGTGTTCTGTGAT
GACCTGCAGTAGGAAGACGAATAGGTGGCCTATGGCATTATTGTACGGAATGATAAACATTGCCTGCATAAATTCTTTTATTATAT
ACAGCCATAATGTCAGTAGCAAGGGAGAAAAGGTTCAAAGTCGCAAAAAATTTATGAGAAACCTTTACATGAGCCTGACGTCATC
GTTTATGCGTAAGCGTTTAGAAGCTCCTACTTTGAAGAGATATTTGCGCGATAATATCTCTAATATTTTGCCAAATGAAGTGCCTG
GTACATCAGATGACAGTACTGAAGAGCCAGTAATGAAAAAACGTACTTACTGTACTTACTGCCCCTCTAAAATAAGGCGAAAGGC
AAATGCATCGTGCAAAAAATGCAAAAAAGTTATTTGTCGAGAGCATAATATTGATATGTGCCAAAGTTGTTTCTGA PB 5' ITR:
<u>CCCTAGAAAGATAGTCTGCGTAAAATTGACGCATG</u>CATTCTTGAAATATTGCTCTCTCTTTCTAAATAGCGCGAATCCGTCGCT
GTGCATTTAGGACATCTCAGTCGCCGCTTGGAGCTCCCGTGAGGCGTGCTTGTCAATGCGGTAAGTGTCACTGATTTTGAACTATA
ACGACCGCGTGAGTCAAAATGACGCATGATTATCTTTTACGTGACTTTTAAGATTTAACTCATACGATAATTATATTGTTATTTCAT
GTTCTACTTACGTGATAACTTATTATATATATATTTTCTTGTTATAGATATC (minimal sequence is underlined and bold, i.e., first 35 bp)

PB 3' ITR:
TAAAAGTTTTGTTACTTTATAGAAGAAATTTTGAGTTTTTGTTTTTTTTTAATAAATAAATAAACATAAATAAATTGTTTGTTGAAT
TTATTATTAGTATGTAAGTGTAAATATAATAAAACTTAATATCTATTCAAATTAATAAATAAACCTCGATATACAGACCGATAAA
CA<u>CATGCGTCAATTTTACGCATGATTATCTTTAACGTACGTCACAATATGATTATCTTTCTAGGG</u> (minimal sequence is underlined and bold, i.e., first 35 bp)

SEQUENCE LISTING

<160> NUMBER OF SEQ ID NOS: 11

<210> SEQ ID NO 1
<211> LENGTH: 9
<212> TYPE: DNA
<213> ORGANISM: Rattus norvegicus
<220> FEATURE:
<223> OTHER INFORMATION: P53 Amino Acid Sequence

<400> SEQUENCE: 1 rrcwwgyyy                                                                9

<210> SEQ ID NO 2
<211> LENGTH: 391
<212> TYPE: PRT
<213> ORGANISM: Rattus norvegicus
<220> FEATURE:
<223> OTHER INFORMATION: P53 Amino Acid Sequence

<400> SEQUENCE: 2

Met Glu Asp Ser Gln Ser Asp Met Ser Ile Glu Leu Pro Leu Ser Gln
 1               5                  10                  15

Glu Thr Phe Ser Cys Leu Trp Lys Leu Leu Pro Pro Asp Asp Ile Leu
             20                  25                  30

Pro Thr Thr Ala Thr Gly Ser Pro Asn Ser Met Glu Asp Leu Phe Leu
         35                  40                  45

Pro Gln Asp Val Ala Glu Leu Leu Glu Gly Pro Glu Glu Ala Leu Gln
     50                  55                  60

Val Ser Ala Pro Ala Ala Gln Glu Pro Gly Thr Glu Ala Pro Ala Pro
 65                  70                  75                  80

Val Ala Pro Ala Ser Ala Thr Pro Trp Pro Leu Ser Ser Ser Val Pro
                 85                  90                  95

Ser Gln Lys Thr Tyr Gln Gly Asn Tyr Gly Phe His Leu Gly Phe Leu
            100                 105                 110

Gln Ser Gly Thr Ala Lys Ser Val Met Cys Thr Tyr Ser Ile Ser Leu
        115                 120                 125

Asn Lys Leu Phe Cys Gln Leu Ala Lys Thr Cys Pro Val Gln Leu Trp
130                 135                 140

Val Thr Ser Thr Pro Pro Pro Gly Thr Arg Val Arg Ala Met Ala Ile
145                 150                 155                 160

Tyr Lys Lys Ser Gln His Met Thr Glu Val Val Arg Arg Cys Pro His
                165                 170                 175

His Glu Arg Cys Ser Asp Gly Asp Gly Leu Ala Pro Pro Gln His Leu
            180                 185                 190

Ile Arg Val Glu Gly Asn Pro Tyr Ala Glu Tyr Leu Asp Asp Arg Gln
        195                 200                 205

Thr Phe Arg His Ser Val Val Val Pro Tyr Glu Pro Pro Glu Val Gly
    210                 215                 220

Ser Asp Tyr Thr Thr Ile His Tyr Lys Tyr Met Cys Asn Ser Ser Cys
225                 230                 235                 240

Met Gly Gly Met Asn Arg Arg Pro Ile Leu Thr Ile Ile Thr Leu Glu
                245                 250                 255

Asp Ser Ser Gly Asn Leu Leu Gly Arg Asp Ser Phe Glu Val Arg Val
            260                 265                 270

Cys Ala Cys Pro Gly Arg Asp Arg Arg Thr Glu Glu Glu Asn Phe Arg
        275                 280                 285

-continued

```
Lys Lys Glu Glu His Cys Pro Glu Leu Pro Pro Gly Ser Ala Lys Arg
    290                 295                 300

Ala Leu Pro Thr Ser Thr Ser Ser Ser Pro Gln Gln Lys Lys Lys Pro
305                 310                 315                 320

Leu Asp Gly Glu Tyr Phe Thr Leu Lys Ile Arg Gly Arg Glu Arg Phe
                325                 330                 335

Glu Met Phe Arg Glu Leu Asn Glu Ala Leu Glu Leu Lys Asp Ala Arg
                340                 345                 350

Ala Ala Glu Glu Ser Gly Asp Ser Arg Ala His Ser Ser Tyr Pro Lys
                355                 360                 365

Thr Lys Lys Gly Gln Ser Thr Ser Arg His Lys Lys Pro Met Ile Lys
                370                 375                 380

Lys Val Gly Pro Asp Ser Asp
385                 390

<210> SEQ ID NO 3
<211> LENGTH: 36
<212> TYPE: PRT
<213> ORGANISM: Mus musculus
<220> FEATURE:
<223> OTHER INFORMATION: P53 Amino Acid Sequence

<400> SEQUENCE: 3

Met Thr Ala Met Glu Glu Ser Gln Ser Asp Ile Ser Leu Glu Leu Pro
1               5                   10                  15

Leu Ser Gln Glu Thr Phe Ser Gly Leu Trp Lys Leu Leu Pro Pro Glu
                20                  25                  30

Asp Ile Leu Pro
            35

<210> SEQ ID NO 4
<211> LENGTH: 354
<212> TYPE: PRT
<213> ORGANISM: Mus musculus
<220> FEATURE:
<223> OTHER INFORMATION: P53 Amino Acid Sequence

<400> SEQUENCE: 4

Ser Pro His Cys Met Asp Asp Leu Leu Leu Pro Gln Asp Val Glu Glu
1               5                   10                  15

Phe Phe Glu Gly Pro Ser Glu Ala Leu Arg Val Ser Gly Ala Pro Ala
                20                  25                  30

Ala Gln Asp Pro Val Thr Glu Thr Pro Gly Pro Val Ala Pro Ala Pro
                35                  40                  45

Ala Thr Pro Trp Pro Leu Ser Ser Phe Val Pro Ser Gln Lys Thr Tyr
    50                  55                  60

Gln Gly Asn Tyr Gly Phe His Leu Gly Phe Leu Gln Ser Gly Thr Ala
65                  70                  75                  80

Lys Ser Val Met Cys Thr Tyr Ser Pro Pro Leu Asn Lys Leu Phe Cys
                85                  90                  95

Gln Leu Ala Lys Thr Cys Pro Val Gln Leu Trp Val Ser Ala Thr Pro
                100                 105                 110

Pro Ala Gly Ser Arg Val Arg Ala Met Ala Ile Tyr Lys Lys Ser Gln
                115                 120                 125

His Met Thr Glu Val Val Arg Arg Cys Pro His His Glu Arg Cys Ser
            130                 135                 140

Asp Gly Asp Gly Leu Ala Pro Pro Gln His Leu Ile Arg Val Glu Gly
145                 150                 155                 160
```

```
Asn Leu Tyr Pro Glu Tyr Leu Glu Asp Arg Gln Thr Phe Arg His Ser
            165                 170                 175
Val Val Val Pro Tyr Glu Pro Pro Glu Ala Gly Ser Glu Tyr Thr Thr
            180                 185                 190
Ile His Tyr Lys Tyr Met Cys Asn Ser Ser Cys Met Gly Gly Met Asn
            195                 200                 205
Arg Arg Pro Ile Leu Thr Ile Ile Thr Leu Glu Asp Ser Ser Gly Asn
            210                 215                 220
Leu Leu Gly Arg Asp Ser Phe Glu Val Arg Val Cys Ala Cys Pro Gly
225                 230                 235                 240
Arg Asp Arg Arg Thr Glu Glu Glu Asn Phe Arg Lys Lys Glu Val Leu
            245                 250                 255
Cys Pro Glu Leu Pro Pro Gly Ser Ala Lys Arg Ala Leu Pro Thr Cys
            260                 265                 270
Thr Ser Ala Ser Pro Pro Gln Lys Lys Lys Pro Leu Asp Gly Glu Tyr
            275                 280                 285
Phe Thr Leu Lys Ile Arg Gly Arg Lys Arg Phe Glu Met Phe Arg Glu
            290                 295                 300
Leu Asn Glu Ala Leu Glu Leu Lys Asp Ala His Ala Thr Glu Glu Ser
305                 310                 315                 320
Gly Asp Ser Arg Ala His Ser Ser Tyr Leu Lys Thr Lys Gly Gln
            325                 330                 335
Ser Thr Ser Arg His Lys Lys Thr Met Val Lys Lys Val Gly Pro Asp
            340                 345                 350
Ser Asp

<210> SEQ ID NO 5
<211> LENGTH: 32
<212> TYPE: DNA
<213> ORGANISM: Rattus norvegicus

<400> SEQUENCE: 5
tacatacact gggcactggg tttgacaact ag                                32

<210> SEQ ID NO 6
<211> LENGTH: 1023
<212> TYPE: DNA
<213> ORGANISM: Artificial Sequence
<220> FEATURE:
<223> OTHER INFORMATION: SB Transposase

<400> SEQUENCE: 6
atgggaaaat caaaagaaat cagccaagac ctcagaaaaa aaattgtaga cctccacaag      60
tctggttcat ccttgggagc aatttccaaa cgcctgaaag taccacgttc atctgtacaa     120
acaatagtac gcaagtataa acaccatggg accacgcagc cgtcataccg ctcaggaagg     180
agacgcgttc tgtctcctag atgaacgt actttggtgc gaaaagtgca atcaatccc       240 agaacaacag caaaggacct tgtgaagatg ctggagaaaa caggtacaaa agtatctata     300
tccacagtaa aacgagtcct atatcgacat aacctgaaag gccgctcagc aaggaagaag     360
ccactgctcc aaaaccgaca taagaaagcc agactacggt ttgcaactgc acatggggac     420
aaagatcgta cttttggag aaatgtcctc tggtctgatg aaacaaaaat agaactgttt     480
ggccataatg accatcgtta tgtttggagg aagaagggg aggcttgcaa gccgaagaac      540
accatcccaa ccgtgaagca cggggggtggc agcatcatgt tgtggggtgtg ctttgctgca    600 ggagggactg gtgcacttca caaaatagat ggcatcatga ggaaggaaaa ttatgtggat    660
```

| | |
|---|---|
| atattgaagc aacatctcaa gacatcagtc aggaagttaa agcttggtcg caaatgggtc | 720 |
| ttccaaatgg acaatgaccc caagcatact tccaaagttg tggcaaaatg gcttaaggac | 780 |
| aacaaagtca aggtattgga gtggccatca caaagccctg acctcaatcc tatagaaaat | 840 |
| ttgtgggcag aactgaaaaa gcgtgtgcga gcaggaggc ctacaaacct gactcagtta | 900 |
| caccagctct gtcaggagga atgggccaaa attcacccaa cttattgtgg gaagcttgtg | 960 |
| gaaggctacc cgaaacgttt gacccaagtt aaacaattta aggcaatgc taccaaatac | 1020 |
| tag | 1023 |

```
<210> SEQ ID NO 7
<211> LENGTH: 229
<212> TYPE: DNA
<213> ORGANISM: Artificial Sequence
<220> FEATURE:
<223> OTHER INFORMATION: SB 5' ITR

<400> SEQUENCE: 7
```

| | |
|---|---|
| cagttgaagt cggaagttta catacactta agttggagtc attaaaactc gttttcaac | 60 |
| tactccacaa atttcttgtt aacaaacaat agttttggca agtcagttag gacatctact | 120 |
| ttgtgcatga cacaagtcat ttttccaaca attgtttaca gacagattat ttcacttata | 180 |
| attcactgta tcacaattcc agtgggtcag aagtttacat acactaagt | 229 |

```
<210> SEQ ID NO 8
<211> LENGTH: 229
<212> TYPE: DNA
<213> ORGANISM: Artificial Sequence
<220> FEATURE:
<223> OTHER INFORMATION: SB 3' ITR

<400> SEQUENCE: 8
```

| | |
|---|---|
| attgagtgta tgtaaacttc tgacccactg gaatgtgat gaaagaaata aaagctgaaa | 60 |
| tgaatcattc tctctactat tattctgata tttcacattc ttaaaataaa gtggtgatcc | 120 |
| taactgacct aagacaggga attttttacta ggattaaatg tcaggaattg tgaaaaagtg | 180 |
| agtttaaatg tatttggcta aggtgtatgt aaacttccga cttcaactg | 229 |

```
<210> SEQ ID NO 9
<211> LENGTH: 1785
<212> TYPE: DNA
<213> ORGANISM: Artificial Sequence
<220> FEATURE:
<223> OTHER INFORMATION: PB Transposase

<400> SEQUENCE: 9
```

| | |
|---|---|
| atgggtagtt ctttagacga tgagcatatc ctctctgctc ttctgcaaag cgatgacgag | 60 |
| cttgttggtg aggattctga cagtgaaata tcagatcacg taagtgaaga tgacgtccag | 120 |
| agcgatacag aagaagcgtt tatagatgag gtacatgaag tgcagccaac gtcaagcggt | 180 |
| agtgaaatat tagacgaaca aaatgttatt gaacaaccag gttcttcatt ggcttctaac | 240 |
| agaatcttga ccttgccaca gaggactatt agaggtaaga ataaacattg ttggtcaact | 300 |
| tcaaagtcca cgaggcgtag ccgagtctct gcactgaaca ttgtcagatc tcaaagaggt | 360 |
| ccgacgcgta tgtgccgcaa tatatatgac ccacttttat gcttcaaact atttttact | 420 |
| gatgagataa tttcggaaat tgtaaaatgg acaaatgctg agatatcatt gaaacgtcgg | 480 |
| gaatctatga caggtgctac atttcgtgac acgaatgaag atgaaatcta tgctttcttt | 540 |
| ggtattctgg taatgacagc agtgagaaaa gataaccaca tgtccacaga tgacctcttt | 600 |

```
gatcgatctt tgtcaatggt gtacgtctct gtaatgagtc gtgatcgttt tgattttttg      660
atacgatgtc ttagaatgga tgacaaaagt atacggccca cacttcgaga aaacgatgta      720
tttactcctg ttagaaaaat atgggatctc tttatccatc agtgcataca aaattacact      780 ccagggctc atttgaccat agatgaacag ttacttggtt ttagaggacg tgtccgttt      840 aggatgtata tcccaaacaa gccaagtaag tatggaataa aaatcctcat gatgtgtgac      900
agtggtacga agtatatgat aaatggaatg ccttatttgg gaagaggaac acagaccaac      960
ggagtaccac tcggtgaata ctacgtgaag gagttatcaa agcctgtgca cggtagttgt     1020
cgtaatatta cgtgtgacaa ttggttcacc tcaatccctt tggcaaaaaa cttactacaa     1080
gaaccgtata agttaaccat tgtgggaacc gtgcgatcaa acaaacgcga gataccggaa     1140
gtactgaaaa acagtcgctc caggccagtg ggaacatcga tgttttgttt tgacggaccc     1200
cttactctcg tctcatataa accgaagcca gctaagatgg tatacttatt atcatcttgt     1260
gatgaggatg cttctatcaa cgaaagtacc ggtaaaccgc aaatggttat gtattataat     1320
caaactaaag gcggagtgga cacgctagac caaatgtgtt ctgtgatgac ctgcagtagg     1380
aagacgaata ggtggcctat ggcattattg tacggaatga taaacattgc ctgcataaat     1440
tctttattta tatacagcca taatgtcagt agcaagggag aaaaggttca aagtcgcaaa     1500
aaatttatga gaacccttta catgagcctg acgtcatcgt ttatgcgtaa gcgtttagaa     1560
gctcctactt tgaagagata tttgcgcgat aatatctcta atattttgcc aaatgaagtg     1620
cctggtacat cagatgacag tactgaagag ccagtaatga aaaaacgtac ttactgtact     1680
tactgcccct ctaaaataag gcgaaaggca aatgcatcgt gcaaaaaatg caaaaaagtt     1740
atttgtcgag agcataatat tgatatgtgc caaagttgtt tctga                     1785

<210> SEQ ID NO 10
<211> LENGTH: 309
<212> TYPE: DNA
<213> ORGANISM: Artificial Sequence
<220> FEATURE:
<223> OTHER INFORMATION: PB 5' ITR

<400> SEQUENCE: 10
ccctagaaag atagtctgcg taaaattgac gcatgcattc ttgaaatatt gctctctctt       60
tctaaatagc gcgaatccgt cgctgtgcat ttaggacatc tcagtcgccg cttggagctc      120
ccgtgaggcg tgcttgtcaa tgcggtaagt gtcactgatt ttgaactata acgaccgcgt      180
gagtcaaaat gacgcatgat tatctttttac gtgactttta agatttaact catacgataa      240
ttatattgtt atttcatgtt ctacttacgt gataacttat tatatatata ttttcttgtt      300
atagatatc                                                               309

<210> SEQ ID NO 11
<211> LENGTH: 238
<212> TYPE: DNA
<213> ORGANISM: Artificial Sequence
<220> FEATURE:
<223> OTHER INFORMATION: PB 3' ITR

<400> SEQUENCE: 11
taaaagtttt gttactttat agaagaaatt ttgagttttt gtttttttt aataaataaa        60 taaacataaa taaattgttt gttgaattta ttattagtat gtaagtgtaa atataataaa      120
acttaatatc tattcaaatt aataaataaa cctcgatata cagaccgata aaacacatgc      180 gtcaattta cgcatgatta tctttaacgt acgtcacaat atgattatct ttctaggg          238
```

GENETICALLY ENGINEERED OR TRANSGENIC RATS EXHIBITING A CANCER PHENOTYPE DUE TO A DISRUPTION OF GERMLINE TUMOR SUPPRESSOR GENES

CROSS-REFERENCE TO RELATED APPLICATIONS

This application claims the benefit of U.S. Provisional Patent Application Ser. No. 61/172,016 filed Apr. 23, 2009, which application is hereby incorporated by reference in its entirety.

BACKGROUND OF THE INVENTION

Gene modification is a process whereby a specific gene, or a fragment of that gene, is altered. This alteration of the targeted gene may result in a change in the level of RNA and/or protein that is encoded by that gene, or the alteration may result in the targeted gene encoding a different RNA or protein than the untargeted gene. The modified gene may be studied in the context of a cell, or, more preferably, in the context of a genetically modified animal.

Genetically modified animals are among the most useful research tools in the biological sciences. An example of a genetically modified animal is a transgenic animal, which has a heterologous (i.e., foreign) gene, or gene fragment, incorporated into their genome that is passed on to their offspring. Although there are several methods of producing genetically modified animals, the most widely used is microinjection of DNA into single cell embryos. These embryos are then transferred into pseudopregnant recipient foster mothers. The offspring are then screened for the presence of the new gene, or gene fragment. Potential applications for genetically modified animals include discovering the genetic basis of human and animal diseases, generating disease resistance in humans and animals, gene therapy, drug testing, and production of improved agricultural livestock.

Identification of novel genes and characterization of their function using mutagenesis has also been shown to be productive in identifying new drugs and drug targets. Creating in vitro cellular models that exhibit phenotypes that are clinically relevant provides a valuable substrate for drug target identification and screening for compounds that modulate not only the phenotype but also the target(s) that controls the phenotype. Modulation of such a target can provide information that validates the target as important for therapeutic intervention in a clinical disorder when such modulation of the target serves to modulate a clinically relevant phenotype.

Animal models exhibiting clinically relevant phenotypes are also valuable for drug discovery and development and for drug target identification. For example, mutation of somatic or germ cells facilitates the production of genetically modified offspring or cloned animals having a phenotype of interest. Such animals have a number of uses, for example as models of physiological disorders (e.g., of human genetic diseases) that are useful for screening the efficacy of candidate therapeutic compounds or compositions for treating or preventing such physiological disorders. Furthermore, identifying the gene(s) responsible for the phenotype provides potential drug targets for modulating the phenotype and, when the phenotype is clinically relevant, for therapeutic intervention. In addition, the manipulation of the genetic makeup of organisms and the identification of new genes have important uses in agriculture, for example in the development of new strains of animals and plants having higher nutritional value or increased resistance to environmental stresses (such as heat, drought, or pests) relative to their wild-type or non-mutant counterparts.

Since most eukaryotic cells are diploid, two copies of most genes are present in each cell. As a consequence, mutating both alleles to create a homozygous mutant animal is often required to produce a desired phenotype, since mutating one copy of a gene may not produce a sufficient change in the level of gene expression or activity of the gene product from that in the non-mutated or wild-type cell or multicellular organism, and since the remaining wild-type copy would still be expressed to produce functional gene product at sufficient levels. Thus, to create a desired change in the level of gene expression and/or function in a cell or multicellular organism, at least two mutations, one in each copy of the gene, are often required in the same cell.

In other instances, mutation in multiple different genes may be required to produce a desired phenotype. In some instances, a mutation in both copies of a single gene will not be sufficient to create the desired physiological effects on the cell or multi-cellular organism. However, a mutation in a second gene, even in only one copy of that second gene, can reduce gene expression levels of the second gene to produce a cumulative phenotypic effect in combination with the first mutation, especially if the second gene is in the same general biological pathway as the first gene. This effect can alter the function of a cell or multi-cellular organism. A hypomorphic mutation in either gene alone could result in protein levels that are severely reduced but with no overt effect on physiology. Severe reductions in the level of expression of both genes, however, can have a major impact. This principle can be extended to other instances where mutations in multiple (two, three, four, or more, for example) genes are required cumulatively to produce an effect on activity of a gene product or on another phenotype in a cell or multi-cellular organism. It should be noted that, in this instance, such genes may all be expressed in the same cell type and therefore, all of the required mutations occur in the same cell. However, the genes may normally be expressed in different cell types (for example, secreting the different gene products from the different cells). In this case, the gene products are expressed in different cells but still have a biochemical relationship such that one or more mutations in each gene is required to produce the desired phenotype.

BRIEF SUMMARY OF THE INVENTION

In accordance with the purposes of this invention, as embodied and broadly described herein, this invention relates to the engineering of animal cells, preferably mammalian, more preferably rat, that are deficient due to the disruption of tumor suppressor gene(s) or gene product(s).

In another aspect, the invention relates to genetically modified rats, as well as the descendants and ancestors of such animals, which are animal models of human cancer and methods of their use.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWING

This invention, as defined in the claims, can be better understood with reference to the following drawings:

FIGS. 1-4 show the process for creating a genetically modified tumor suppressor rat model using DNA transposons to create an insertion mutation directly in the germ line.

FIG. 1: Gene modification by DNA transposons.

FIG. 2: Breeding strategy for creating rat knockouts directly in the germ cells with DNA transposons.

FIG. 3: DNA sequences

DETAILED DESCRIPTION OF THE INVENTION

Definitions

Figure 1:
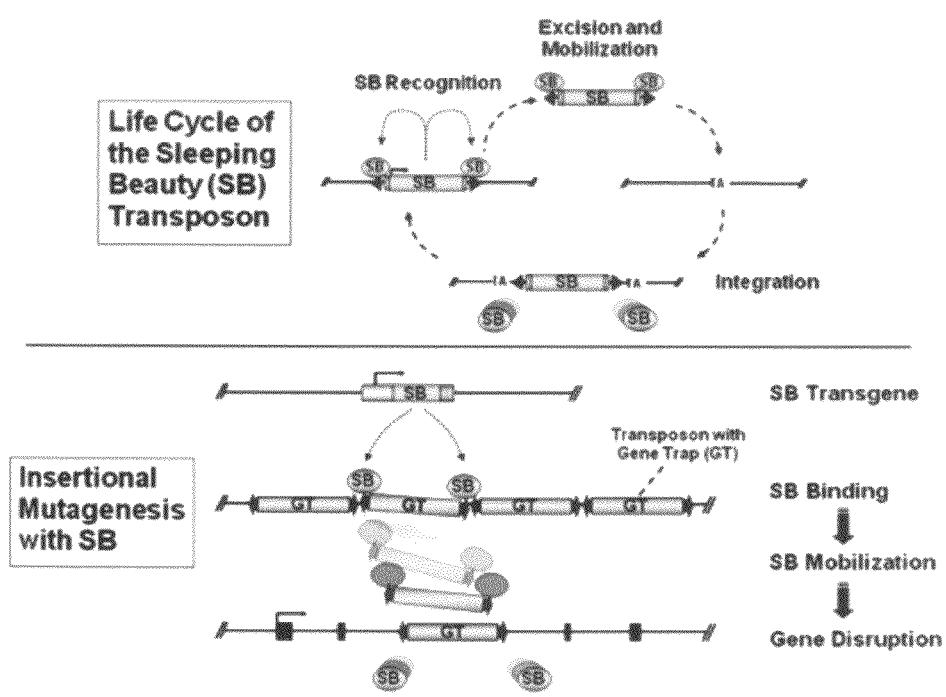

The present invention may be understood more readily by reference to the following detailed description of preferred embodiments of the invention and the Examples included therein and to the Figures and their previous and following description. Although any methods and materials similar or equivalent to those described herein can be used in the practice or testing of the present invention, the preferred methods, devices, and materials are now described. All references, publications, patents, patent applications, and commercial materials mentioned herein are incorporated herein by reference for the purpose of describing and disclosing the materials and/or methodologies which are reported in the publications which might be used in connection with the invention. Nothing herein is to be construed as an admission that the invention is not entitled to antedate such disclosure by virtue of prior invention.

Before the present compounds, compositions, articles, devices, and/or methods are disclosed and described, it is to be understood that this invention is not limited to specific synthetic methods, specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

Throughout this application, reference is made to various proteins and nucleic acids. It is understood that any names used for proteins or nucleic acids are art-recognized names, such that the reference to the name constitutes a disclosure of the molecule itself.

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

"Complementary," as used herein, refers to the subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs).

A "deletion mutation" means a type of mutation that involves the loss of genetic material, which may be from a single base to an entire piece of chromosome. Deletion of one or more nucleotides in the DNA could alter the reading frame of the gene; hence, it could result in a synthesis of a nonfunctional protein due to the incorrect sequence of amino acids during translation.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed". An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "gene", also called a "structural gene" means a DNA sequence that codes for or corresponds to a particular sequence of amino acids which comprise all or part of one or more proteins or enzymes, and may or may not include introns and regulatory DNA sequences, such as promoter sequences, 5'-untranslated region, or 3'-untranslated region which affect for example the conditions under which the gene is expressed. Some genes, which are not structural genes, may be transcribed from DNA to RNA, but are not translated into an amino acid sequence. Other genes may function as regulators of structural genes or as regulators of DNA transcription.

By "genetically modified" is meant a gene that is altered from its native state (e.g. by insertion mutation, deletion mutation, nucleic acid sequence mutation, or other mutation), or that a gene product is altered from its natural state (e.g. by delivery of a transgene that works in trans on a gene's encoded mRNA or protein, such as delivery of inhibitory RNA or delivery of a dominant negative transgene).

By "exon" is meant a region of a gene which includes sequences which are used to encode the amino acid sequence of the gene product.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is such an element operatively associated with a different gene than the one it is operatively associated with in nature.

As used herein, the term "homology" refers to the subunit sequence identity or similarity between two polymeric molecules e.g., between two nucleic acid molecules, e.g., between two DNA molecules, or two polypeptide molecules. When a subunit position in both of the two molecules is occupied by the same monomeric subunit, e.g., if a position in each of two polypeptide molecules is occupied by phenylalanine, then they are identical at that position. The homology between two sequences, most clearly defined as the % identity, is a direct function of the number of identical positions, e.g., if half (e.g., 5 positions in a polymer 10 subunits in length) of the positions in two polypeptide sequences are identical then the two sequences are 50% identical; if 70% of the positions, e.g., 7 out of 10, are matched or homologous, the two sequences share 70% identity. By way of example, the polypeptide sequences ACDEFG and ACDHIK share 50% identity and the nucleotide sequences CAATCG and CAAGAC share 50% identity.

"Homologous recombination" is the physical exchange of DNA expedited by the breakage and reunion of two non-sister chromatids. In order to undergo recombination the DNA duplexes must have complimentarity. The molecular mechanism is as follows: DNA duplexes pair, homologous strands are nicked, and broken strands exchange DNA between duplexes. The region at the site of recombination is called the hybrid DNA or heteroduplex DNA. Second nicks are made in the other strand, and the second strand crosses over between duplexes. After this second crossover event the reciprocal recombinant or splice recombinant is created. The duplex of one DNA parent is covalently linked to the duplex of another DNA parent. Homologous recombination creates a stretch of heteroduplex DNA.

A "hypomorphic mutation" is a change to the genetic material (usually DNA or RNA), which can be caused by any form of genetic mutation, and causes an decrease in normal gene function without causing a complete absence of normal gene function.

The term "inbred animal" is used herein to refer to an animal that has been interbred with other similar animals of the same species in order to preserve and fix certain characteristics, or to prevent other characteristics from being introduced into the breeding population.

The term "insertional mutation" is used herein to refer the translocation of nucleic acid from one location to another location which is in the genome of an animal so that it is integrated into the genome, thereby creating a mutation in the genome. Insertional mutations can also include knocking out or knocking in of endogenous or exogenous DNA via gene trap or cassette insertion. Exogenous DNA can access the cell via electroporation or chemical transformation. If the exogenous DNA has homology with chromosomal DNA it will align itself with endogenous DNA. The exogenous DNA is then inserted or disrupts the endogenous DNA via two adjacent crossing over events, known as homologous recombination. A targeting vector can use homologous recombination for insertional mutagenesis. Insertional mutagenesis of endogenous or exogenous DNA can also be carried out via DNA transposon. The DNA transposon is a mobile element that can insert itself along with additional exogenous DNA into the genome. Insertional mutagenesis of endogenous or exogenous DNA can be carried out by retroviruses. Retroviruses have a RNA viral genome that is converted into DNA by reverse transcriptase in the cytoplasm of the infected cell. Linear retroviral DNA is transported into the nucleus, and become integrated by an enzyme called integrase. Insertional mutagenesis of endogenous or exogenous DNA can also be done by retrotransposons in which an RNA intermediate is translated into double stranded DNA by reverse transcriptase, and inserting itself into the genome.

The term "gene knockdown" refers to techniques by which the expression of one or more genes is reduced, either through genetic modification (a change in the DNA of one of the organism's chromosomes) or by treatment with a reagent such as a short DNA or RNA oligonucleotide with a sequence complementary to either an mRNA transcript or a gene. If genetic modification of DNA is done, the result is a "knockdown organism" or "knockdowns".

By "knock-out" is meant an alteration in the nucleic acid sequence that reduces the biological activity of the polypeptide normally encoded therefrom by at least 80% compared to the unaltered gene. The alteration may be an insertion, deletion, frameshift mutation, or missense mutation. Preferably, the alteration is an insertion or deletion, or is a frameshift mutation that creates a stop codon.

An "L1 sequence" or "L1 insertion sequence" as used herein, refers to a sequence of DNA comprising an L1 element comprising a 5' UTR, ORF1 and ORF2, a 3' UTR and a poly A signal, wherein the 3' UTR has DNA (e.g. a gene trap or other cassette) positioned either therein or positioned between the 3' UTR and the poly A signal, which DNA is to be inserted into the genome of a cell.

A "mutation" is a detectable change in the genetic material in the animal, which is transmitted to the animal's progeny. A mutation is usually a change in one or more deoxyribonucleotides, the modification being obtained by, for example, adding, deleting, inverting, or substituting nucleotides. Exemplary mutations include but are not limited to a deletion mutation, an insertion mutation, a non-sense mutation or a missense mutation. Thus, the terms "mutation" or "mutated" as used herein are intended to denote an alteration in the "normal" or "wild-type" nucleotide sequence of any nucleotide sequence or region of the allele. As used herein, the terms "normal" and "wild-type" are intended to be synonymous, and to denote any nucleotide sequence typically found in nature. The terms "mutated" and "normal" are thus defined relative to one another; where a cell has two chromosomal alleles of a gene that differ in nucleotide sequence, at least one of these alleles is a "mutant" allele as that term is used herein. Based on these definitions, an "endogenous tumor suppressing gene" is the "wild-type" tumor suppressing gene that exists normally in a cell, and a "mutated tumor suppressor gene" defines a gene that differs in nucleotide sequence from the wild-type gene.

"Non-homologous end joining (NHEJ)" is a cellular repair mechanism. The NHEF pathway is defined by the ligation of blunt ended double stand DNA breaks. The pathway is initiated by double strand breaks in the DNA, and works through the ligation of DNA duplex blunt ends. The first step is recognition of double strand breaks and formation of scaffold. The trimming, filling in of single stranded overhangs to create blunt ends and joining is executed by the NHEF pathway. An example of NHEJ is repair of a DNA cleavage site created by a zinc finger nuclease (ZFN). This would normally be expected to create a small deletion mutation.

"Nucleic Acid sequence mutation" is a mutation to the DNA of a gene that involves change of one or multiple nucleotides. A point mutation which affects a single nucleotide can result in a transition (purine to purine or pyrimidine to pyrimidine) or a transversion (purine to pyrimidine or pyrimidine to purine). A point mutation that changes a codon to represent a different amino acid is a missense mutation. Some point mutations can cause a change in amino acid so that there is a premature stop codon; these mutations are called nonsense mutations. A mutation that inserts or deletes a single base will change the entire downstream sequence and are known as frameshift mutations. Some mutations change a base pair but have no effect on amino acid representation; these are called silent mutations. Mutations to the nucleic acid of a gene can have different consequences based on their location (intron, exon, regulatory sequence, and splice joint).

"Optional" or "optionally" means that the subsequently described event or circumstance may or may not occur, and that the description includes instances where said event or circumstance occurs and instances where it does not.

The term "outbred animal" is used herein to refer to an animal that breeds with any other animal of the same species without regard to the preservation of certain characteristics.

As used herein, the term "phenotype" means any property of a cell or organism. A phenotype can simply be a change in expression of an mRNA or protein. Examples of phenotypes also include, but are in no way limited to, cellular, biochemical, histological, behavioral, or whole organismal properties that can be detected by the artisan. Phenotypes include, but are not limited to, cellular transformation, cell migration, cell morphology, cell activation, resistance or sensitivity to drugs or chemicals, resistance or sensitivity to pathogenic protein localization within the cell (e.g. translocation of a protein from the cytoplasm to the nucleus), profile of secreted or cell surface proteins, (e.g., bacterial or viral) infection, post-translational modifications, protein localization within the cell (e.g. translocation of a protein from the cytoplasm to the nucleus), profile of secreted or cell surface proteins, cell proliferation, signal transduction, metabolic defects or enhancements, transcriptional activity, cell or organ transcript profiles (e.g., as detected using gene chips), apoptosis resistance or sensitivity, animal behavior, organ histology, blood chemistry, biochemical activities, gross morphological properties, life span, tumor susceptibility, weight, height/length, immune function, organ function, any disease state, and other properties known in the art. In certain situations and therefore in certain embodiments of the invention, the effects of mutation of one or more genes in a cell or organism can be determined by observing a change in one or more given phenotypes (e.g., in one or more given structural or functional features such as one or more of the phenotypes indicated above) of the mutated cell or organism compared to the same structural or functional feature(s) in a corresponding wild-type or (non-mutated) cell or organism (e.g., a cell or organism that in which the gene(s) have not been mutated).

By "plasmid" is meant a circular strand of nucleic acid capable of autosomal replication in plasmid-carrying bacteria. The term includes nucleic acid which may be either DNA or RNA and may be single- or double-stranded. The plasmid of the definition may also include the sequences which correspond to a bacterial origin of replication.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. The promoter may be operatively associated with other expression control sequences, including enhancer and repressor sequences.

A "random site" is used herein to refer to a location in the genome where a retrotransposition or transposition or other DNA mutation event takes places, without prior intention of insertion at that particular location. It is also used herein to refer to a location in the genome that is randomly modified by any insertion mutation or deletion mutation or nucleic acid sequence mutation.

The term "regulatory sequence" is defined herein as including promoters, enhancers and other expression control elements such as polyadenylation sequences, matrix attachment sites, insulator regions for expression of multiple genes on a single construct, ribosome entry/attachment sites, introns that are able to enhance expression, and silencers.

By "reporter gene" is meant any gene which encodes a product whose expression is detectable. A reporter gene product may have one of the following attributes, without restriction: fluorescence (e.g., green fluorescent protein), enzymatic activity (e.g., lacZ or luciferase), or an ability to be specifically bound by a second molecule (e.g., biotin or an antibody-recognizable epitope).

By "retrotransposition" as used herein, is meant the process of integration of a sequence into a genome, expression of that sequence in the genome, reverse transcription of the integrated sequence to generate an extrachromosomal copy of the sequence and reintegration of the sequence into the genome.

A "retrotransposition event" is used herein to refer to the translocation of a retrotransposon from a first location to a second location with the preferable outcome being integration of a retrotransposon into the genome at the second location. The process involves a RNA intermediate, and can retrotranspose from one chromosomal location to another or from introduced exogenous DNA to endogenous chromosomal DNA.

By "selectable marker" is meant a gene product which may be selected for or against using chemical compounds, especially drugs. Selectable markers often are enzymes with an ability to metabolize the toxic drugs into non-lethal products. For example, the pac (puromycin acetyl transferase) gene product can metabolize puromycin, the dhfr gene product can metabolize trimethoprim (tmp) and the bla gene product can metabolize ampicillin (amp). Selectable markers may convert a benign drug into a toxin. For example, the HSV tk gene product can change its substrate, FIAU, into a lethal substance. Another selectable marker is one which may be utilized in both prokaryotic and eukaryotic cells. The neo gene, for example, metabolizes and neutralizes the toxic effects of the prokaryotic drug, kanamycin, as well as the eukaryotic drug, G418.

By "selectable marker gene" as used herein is meant a gene or other expression cassette which encodes a protein which facilitates identification of cells into which the selectable marker gene is inserted.

A "specific site" is used herein to refer to a location in the genome that is predetermined as the position where a retrotransposition or transposition event or other DNA mutation will take place. It is also used herein to refer to a specific location in the genome that is modified by any insertion mutation or deletion mutation or nucleic acid sequence mutation.

As used herein, the term "targeted genetic recombination" refers to a process wherein recombination occurs within a DNA target locus present in a host cell or host organism. Recombination can involve either homologous or non-homologous DNA.

The term "transfection" means the introduction of a foreign nucleic acid into a cell. The term "transformation"

means the introduction of a "foreign" (i.e. extrinsic or extracellular) gene, DNA or RNA sequence to an ES cell or pronucleus, so that the cell will express the introduced gene or sequence to produce a desired substance in a genetically modified animal.

By "transgenic" is meant any animal which includes a nucleic acid sequence which is inserted by artifice into a cell and becomes a part of the genome of the animal that develops from that cell. Such a transgene may be partly or entirely heterologous to the transgenic animal. Although transgenic mice represent another embodiment of the invention, other transgenic mammals including, without limitation, transgenic rodents (for example, hamsters, guinea pigs, rabbits, and rats), and transgenic pigs, cattle, sheep, and goats are included in the definition.

By "transposition" as used herein, is meant the process of one DNA sequence insertion into another (location) without relying on sequence homology. The DNA element can be transposed from one chromosomal location to another or from introduction of exogenous DNA and inserted into the genome.

A "transposition event" is used herein to refer to the translocation of a DNA transposon either from one location on the chromosomal DNA to another or from one location on introduced exogenous DNA to another on the chromosomal DNA.

By "transposon" or "transposon insertion sequence" or "transposable element" is meant a linear strand of DNA capable of integrating into a second strand of DNA which may be linear or may be a circularized plasmid. Transposons often have insertion sequences, or remnants thereof, at their extremities, and are able to integrate into sites within the second strand of DNA selected at random, or nearly random. Preferred transposons have a short (e.g., less than 200) base pair repeat at either end of the linear DNA. By "transposable elements" is meant any genetic construct including but not limited to any gene, gene fragment, or nucleic acid that can be integrated into a target DNA sequence under control of an integrating enzyme, often called a transposase.

A coding sequence is "under the control of" or "operatively associated with" transcriptional and translational control sequences in a cell when RNA polymerase transcribes the coding sequence into mRNA, which is then trans-RNA spliced (if it contains introns) and translated, in the case of mRNA, into the protein encoded by the coding sequence.

The term "variant" may also be used to indicate a modified or altered gene, DNA sequence, enzyme, cell, etc., i.e., any kind of mutant.

The term "vector" is used interchangeably with the terms "construct", "cloning vector" and "expression vector" and means the vehicle by which a DNA or RNA sequence (e.g. a foreign gene) can be introduced into a host cell, (e.g. ES cell or pronucleus) so as to transform the host and promote expression (e.g. transcription and translation) of the introduced sequence including but not limited to plasmid, phage, transposons, retrotransposons, viral vector, and retroviral vector. By "non-viral vector" is meant any vector that does not comprise a virus or retrovirus.

A "vector sequence" as used herein, refers to a sequence of DNA comprising at least one origin of DNA replication and at least one selectable marker gene.

For the purposes of the present invention, the term "zinc finger nuclease" or "ZFN" refers to a chimeric protein molecule comprising at least one zinc finger DNA binding domain effectively linked to at least one nuclease or part of a nuclease capable of cleaving DNA when fully assembled. Ordinarily, cleavage by a ZFN at a target locus results in a double stranded break (DSB) at that locus.

The present invention provides a desired rat or a rat cell which contains a predefined, specific and desired alteration rendering the rat or rat cell predisposed to cancer. Specifically, the invention pertains to a genetically altered rat, or a rat cell in culture, that is defective in at least one of two alleles of a tumor-suppressor gene such as the p53 gene, the Rb gene, etc. In one embodiment, the tumor-suppressor gene is Robo1 gene. In another embodiment, the tumor-suppressor gene is the p53 gene. In another embodiment, the tumor-suppressor gene is one of several known tumor-suppressor genes, such as (Abcb4, Abcc1, Abcg2, Actb, Ahr, Akt, Akt1, Akt2, Akt3, Amhr2, Anxa7, Apc, Ar, Atm, Axin2, B2m, Bard1, Bcl2l1, Becn1, Bhlha15, Bin1, Blm, Braf, Brca1, Brca2, Brca3, Braf, Brcata, Brinp3, Brip1, Bub1b, Bwscr1a, Cadm3, Casc1, Casp3, Casp7, Casp8, Cav1, Ccnd1, Ccr4, Ccs1, Cd28, Cdc25a, Cd95, Cdh1, Cdkn1a, Cdkn1b, Cdkn2a, Cdkn2b, Cdkn2c, Chek1, Chek2, Crcs1, Crcs10, Crcs11, Crcs2, Crcs3, Crcs4, Crcs5, Crcs6, Crcs7, Crcs8, Crcs9, Ctnnb1, Cyp1a1, Cyp2a6, Cyp2b2, Dcc, Dkc1, Dicer1, Dmtf1, Dnmt1, E2f1, Eaf2, Eef1a1, Egfr, Egfr4, Erbb2, Erbb4, Ercc2, Ercc6, Ercc8, Errfi1, Esr1, Etv4, Faslg, Fbxo10, Fgfr3, Fntb, Foxm1, Foxn1, Fzd6, Fzd7, Fzr1, Gadd45a, Gast, Gnai2, Gpc1, Gpr124, Gpr87, Gprc5a, Gprc5d, Grb2, Gstm1, Gstm5, Gstp1, Gstt1, H19, H2afx, Hck, Lims1, Hdac, Hic1, Hmmr, Hnpcc8, Hprt, Hras, Htatip2, Il1b, Il10, Il2, Il6, Il8rb Inha, Itgav, Jun, Jak3, Kit, Klf4, Kras, Kras2, Lig1, Lig4, Lkb1, Lmo7, Lncr1, Lncr2, Lncr3, Lncr4, Ltbp4, Lyz2, Lzts1, Mad1l1, Mad2l1, Mapk14, Mcc, Mcm4, Men1, Met, Mgat5, Mif, Mlh1, Mlh3, Mmp8, Mnt, Mpo, Msh2, Msh3, Msh6, Msmb, Mthfr, Mutyh, Myh11, Nat2, Nbn, Ncoa3, Neil1, Nf1, Nf2, Nfe2l1, Nhej1, Nkx2-1, Nkx2-9, Nkx3-1, Nqo1, Nras, Nudt1, Ogg1, Oxgr1, Palb2, Park2, Pggt1b, Pgr, Pi3k, Pik3ca, Piwil2, Pla2g2a, Plg, Plk3, Pms1, Pms2, Pold1, Pole, Ppard, Pparg, Ppfia2, Ppm1d, Prdm2, Prdx1, Prkar1a, Ptch, Pten, Prom1, Psca, Ptch1, Ptf1a, Ptger2, Ptpn13, Ptprj, Rara, Rad51, Rassf1, Rb, Rb1, Rb1cc1, Rb12, Recgl4, Ret, Rgs5, Rhoc, Rint1, Robo1, Rpl38, S100a4, Smad4, Smarcb1, Smo, Snx25, Spata13, Srpx, Ssic1, Sstr2, Sstr5, Stat3, St5, St7, St14, Stk11, Suds3, Tap1, Tbx21, Terc, Tnf, Tp53, Trpm5, Tsc2, Tsc1, Vhl, Wt1, Wt2, Xrcc1, Xrcc5, and Xrcc6). The inactivation of at least one of these tumor suppressor alleles results in an animal with a higher susceptibility to tumor induction. In one embodiment, the genetically altered animal is a rat of this type and is able to serve as a useful model for hereditary cancers and as a test animal for carcinogen studies. The invention additionally pertains to the use of such rats or rat cells, and their progeny in research and medicine.

In one embodiment, the invention provides a genetically modified or chimeric rat cell whose genome comprises two chromosomal alleles of a tumor-suppressing gene (especially, the Robo1 gene or p53 gene), wherein at least one of the two alleles contains a mutation, or the progeny of this cell. The invention includes the embodiment of the above animal cell, wherein one of the alleles expresses a normal tumor-suppressing gene product. The invention includes the embodiment wherein the rat cell is a pluripotent cell such as an embryonic cell, embryonic stem (ES) cell, induced pluripotent stem cell (iPS), or spermatagonial stem (SS) cell, and in particular, wherein the tumor-suppressing gene is a Robo1 or p53 gene. In another embodiment, the tumor-suppressor gene is one of several known tumor-suppressor genes, such as (Abcb4, Abcc1, Abcg2, Actb, Ahr, Akt, Akt1, Akt2, Akt3, Amhr2, Anxa7, Apc, Ar, Atm, Axin2, B2m, Bard1, Bcl2l1, Becn1, Bhlha15, Bin1, Blm, Braf, Brca1, Brca2, Brca3, Braf, Brcata, Brinp3, Brip1, Bub1b, Bwscr1a, Cadm3, Casc1, Casp3, Casp7, Casp8, Cav1, Ccnd1, Ccr4, Ccs1, Cd28, Cdc25a, Cd95, Cdh1, Cdkn1a, Cdkn1b, Cdkn2a, Cdkn2b, Cdkn2c, Chek1, Chek2, Crcs1, Crcs10, Crcs11, Crcs2, Crcs3, Crcs4, Crcs5, Crcs6, Crcs7, Crcs8, Crcs9, Ctnnb1, Cyp1a1, Cyp2a6, Cyp2b2, Dcc, Dkc1, Dicer1, Dmtf1, Dnmt1, E2f1, Eaf2, Eef1a1, Egfr, Egfr4, Erbb2, Erbb4, Ercc2, Ercc6, Ercc8, Errfi1, Esr1, Etv4, Faslg, Fbxo10, Fgfr3, Fntb, Foxm1, Foxn1, Fzd6, Fzd7, Fzr1, Gadd45a, Gast, Gnai2, Gpc1, Gpr124, Gpr87, Gprc5a, Gprc5d, Grb2, Gstm1, Gstm5, Gstp1, Gstt1, H19, H2afx, Hck, Lims1, Hdac, Hic1, Hmmr, Hnpcc8, Hprt, Hras, Htatip2, Il1b, Il10, Il2, Il6, Il8rb Inha, Itgav, Jun, Jak3, Kit, Klf4, Kras, Kras2, Lig1, Lig4, Lkb1, Lmo7, Lncr1, Lncr2, Lncr3, Lncr4, Ltbp4, Lyz2, Lzts1, Mad1l1, Mad2l1, Mapk14, Mcc, Mcm4, Men1, Met, Mgat5, Mif, Mlh1, Mlh3, Mmp8, Mnt, Mpo, Msh2, Msh3, Msh6, Msmb, Mthfr, Mutyh, Myh11, Nat2, Nbn, Ncoa3, Neil1, Nf1, Nf2, Nfe2l1, Nhej1, Nkx2-1, Nkx2-9, Nkx3-1, Nqo1, Nras, Nudt1, Ogg1, Oxgr1, Palb2, Park2, Pggt1b, Pgr, Pi3k, Pik3ca, Piwil2, Pla2g2a, Plg, Plk3, Pms1, Pms2, Pold1, Pole, Ppard, Pparg, Ppfia2, Ppm1d, Prdm2, Prdx1, Prkar1a, Ptch, Pten, Prom1, Psca, Ptch1, Ptf1a, Ptger2, Ptpn13, Ptprj, Rara, Rad51, Rassf1, Rb, Rb1, Rb1cc1, Rb12, Recgl4, Ret, Rgs5, Rhoc, Rint1, Robo1, Rpl38, S100a4, Smad4, Smarcb1, Smo, Snx25, Spata13, Srpx, Ssic1, Sstr2, Sstr5, Stat3, St5, St7, St14, Stk11, Suds3, Tap1, Tbx21, Terc, Tnf, Tp53, Trpm5, Tsc2, Tsc1, Vhl, Wt1, Wt2, Xrcc1, Xrcc5, and Xrcc6). In another embodiment, the rat cell is a somatic cell.

The methods of the present invention can be used to mutate any eukaryotic cell, including, but not limited to, haploid (in the case of multiple gene mutations), diploid, triploid, tetraploid, or aneuploid. In one embodiment, the cell is diploid. Cells in which the methods of the present invention can be advantageously used include, but are not limited to, primary cells (e.g., cells that have been explanted directly from a donor organism) or secondary cells (e.g., primary cells that have been grown and that have divided for some period of time in vitro, e.g., for 10-100 generations). Such primary or secondary cells can be derived from multi-cellular organisms, or single-celled organisms. The cells used in accordance with the invention include normal cells, terminally differentiated cells, or immortalized cells (including cell lines, which can be normal, established or transformed), and can be differentiated (e.g., somatic cells or germ cells) or undifferentiated (e.g., multipotent, pluripotent or totipotent stem cells).

A variety of cells isolated from the above-referenced tissues, or obtained from other sources (e.g., commercial sources or cell banks), can be used in accordance with the invention. Non-limiting examples of such cells include somatic cells such as blood cells (erythrocytes and leukocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other stromal cells (e.g., macrophages, dendritic cells, thymic nurse cells, Schwann cells, etc.). Eukaryotic germ cells (spermatocytes and oocytes) can also be used in accordance with the invention, as can the progenitors, precursors and stem cells that give rise to the above-described somatic and germ cells. These cells, tissues and organs can be normal, or they can be pathological such as those involved in diseases or physical disorders, including but not limited to infectious diseases (caused by bacteria, fungi or yeast, viruses (including HIV) or parasites), in genetic or biochemical pathologies (e.g., cystic fibrosis, hemophilia, Alzheimer's disease, schizophrenia, muscular dystrophy, multiple sclerosis, etc.), or in carcinogenesis and other cancer-related processes. Rat cells include embryonic cells, spermatogonial stem cells, embryonic stem cells, and iPS cells are envisioned.

In certain embodiments of the invention, cells can be mutated within the organism or within the native environment as in tissue explants (e.g., in vivo or in situ). Alternatively, tissues or cells isolated from the organism using art-known methods and genes can be mutated according to the present methods. The tissues or cells are either maintained in culture (e.g., in vitro), or re-implanted into a tissue or organism (e.g., ex vivo).

The invention also includes a non-human genetically modified or chimeric rat whose genome comprises two chromosomal alleles of a tumor-suppressing gene, wherein at least one of the two alleles contains a mutation, or the progeny of the animal, or an ancestor of the animal, at an embryonic stage (preferably the one-cell, or fertilized oocyte stage, and generally, not later than about the 8-cell stage) contains a mutation. The invention also includes the embodiment wherein the tumor suppressing gene of the rat is a Robo1 or p53 gene. In another embodiment, the tumor-suppressor gene is one of several known tumor-suppressor genes, such as (Abcb4, Abcc1, Abcg2, Actb, Ahr, Akt, Akt1, Akt2, Akt3, Amhr2, Anxa7, Apc, Ar, Atm, Axin2, B2m, Bard1, Bcl2l1, Becn1, Bhlha15, Bin1, Blm, Braf, Brca1, Brca2, Brca3, Braf, Brcata, Brinp3, Brip1, Bub1b, Bwscr1a, Cadm3, Casc1, Casp3, Casp7, Casp8, Cav1, Ccnd1, Ccr4, Ccs1, Cd28, Cdc25a, Cd95, Cdh1, Cdkn1a, Cdkn1b, Cdkn2a, Cdkn2b, Cdkn2c, Chek1, Chek2, Crcs1, Crcs10, Crcs11, Crcs2, Crcs3, Crcs4, Crcs5, Crcs6, Crcs7, Crcs8, Crcs9, Ctnnb1, Cyp1a1, Cyp2a6, Cyp2b2, Dcc, Dkc1, Dicer1, Dmtf1, Dnmt1, E2f1, Eaf2, Eef1a1, Egfr, Egfr4, Erbb2, Erbb4, Ercc2, Ercc6, Ercc8, Errfi1, Esr1, Etv4, Faslg, Fbxo10, Fgfr3, Fntb, Foxm1, Foxn1, Fzd6, Fzd7, Fzr1, Gadd45a, Gast, Gnai2, Gpc1, Gpr124, Gpr87, Gprc5a, Gprc5d, Grb2, Gstm1, Gstm5, Gstp1, Gstt1, H19, H2afx, Hck, Lims1, Hdac, Hic1, Hmmr, Hnpcc8, Hprt, Hras, Htatip2, Il1b, Il10, Il2, Il6, Il8rb Inha, Itgav, Jun, Jak3, Kit, Klf4, Kras, Kras2, Lig1, Lig4, Lkb1, Lmo7, Lncr1, Lncr2, Lncr3, Lncr4, Ltbp4, Lyz2, Lzts1, Mad1l1, Mad2l1, Mapk14, Mcc, Mcm4, Men1, Met, Mgat5, Mif, Mlh1, Mlh3, Mmp8, Mnt, Mpo, Msh2, Msh3, Msh6, Msmb, Mthfr, Mutyh, Myh11, Nat2, Nbn, Ncoa3, Neil1, Nf1, Nf2, Nfe2l1, Nhej1, Nkx2-1, Nkx2-9, Nkx3-1, Nqo1, Nras, Nudt1, Ogg1, Oxgr1, Palb2, Park2, Pggt1b, Pgr, Pi3k, Pik3ca, Piwil2, Pla2g2a, Plg, Plk3, Pms1, Pms2, Pold1, Pole, Ppard, Pparg, Ppfia2, Ppm1d, Prdm2, Prdx1, Prkar1a, Ptch, Pten, Prom1, Psca, Ptch1, Ptf1a, Ptger2, Ptpn13, Ptprj, Rara, Rad51, Rassf1, Rb, Rb1, Rb1cc1, Rb12, Recgl4, Ret, Rgs5, Rhoc, Rint1, Robo1, Rpl38, S100a4, Smad4, Smarcb1, Smo, Snx25, Spata13, Srpx, Ssic1, Sstr2, Sstr5, Stat3, St5, St7, St14, Stk11, Suds3, Tap1, Tbx21, Terc, Tnf, Tp53, Trpm5, Tsc2, Tsc1, Vhl, Wt1, Wt2, Xrcc1, Xrcc5, and Xrcc6). The invention is also directed to the embodiment wherein the animal cell is a rat pluripotent cell. The invention is also directed to the embodiment wherein the animal cell is a rat somatic cell.

Figure 2:
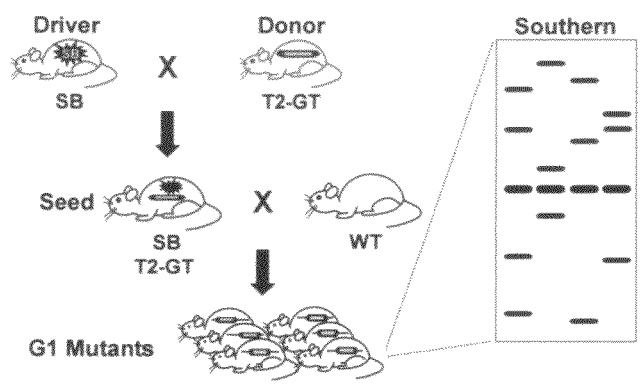

In one embodiment, the tumor suppressor gene is mutated directly in the germ cells of a living organism. The separate transgenes for DNA transposon flanking ends and transposase are facilitated to create an active DNA transposon which integrates into the rat's genome. A plasmid containing tranposon inverted repeats is used to create the transgenic "donor" rat. A plasmid containing transposase is used to create a separate transgenic "driver" rat. The donor rat is then bred with the driver rat to produce a rat which contains both donor transposon with flanking repeats and driver transposase (FIG. 2). This rat known as the "seed" rat has an activated DNA transposase which drives transposition events. The seed rat is bred to wild type rats to create heterozygote progeny with new transposon insertions. The heterozygotes can be interbred to create homozygous rats. Transposon insertional mutations are identified and recovered via sequencing and cloning strategy at the transposon-cellular DNA junction fragments. The rats that are identified to have a new DNA transposon insertion in a known gene or EST or DNA sequence of interest are called knockout rats.

In one embodiment, the tumor suppressor gene is mutated in the oocyte before fusion of the pronuclei. This method for genetic modification of rats uses microinjected DNA into the male pronucleus before nuclear fusion. The microinjected DNA creates a genetically modified founder rat. A female rat is mated and the fertilized eggs are flushed from their oviducts. After entry of the sperm into the egg, the male and female pronuclei are separate entities until nuclear fusion occurs. The male pronucleus is larger are can be identified via dissecting microscope. The egg can be held in place by micromanipulation using a holding pipette. The male pronucleus is then microinjected with DNA that can be genetically modified. The microinjected eggs are then implanted into a surrogate pseudopregnant female which was mated with a vasectomized male for uterus preparation. The foster mother gives birth to genetically modified animal. The microinjection method can introduce genetic modifications directly to the germline of a living animal.

In another embodiment, the tumor-suppressor gene is mutated in a pluripotent cell. These pluripotent cells can proliferate in cell culture and be genetically modified without affecting their ability to differentiate into other cell types including germline cells. Genetically modifying the pluripotent cells from a donor are microinjected into a recipient blastocyst, or in the case of spermatogonial stem cells can be injected into the rete testis of a recipient animal. Recipient genetically modified blastocysts are implanted into pseudopregnant surrogate females. The progeny which have a genetic modification to the germline can then be established, and lines homozygous for the genetic modification can be produced by interbreeding.

In another embodiment, the tumor-suppressor gene is mutated in a somatic cell and then used to create a genetically modified animal by somatic cell nuclear transfer. Somatic cell nuclear transfer uses embryonic, fetal, or adult donor cells which are isolated, cultured, and/or modified to establish a cell line. Individual donor cells are fused to an enucleated oocyte. The fused cells are cultured to blastocyst stage, and then transplanted into the uterus of a pseudopregnant female.

In one embodiment, the present invention is directed to methods for mutating a single gene or multiple genes (e.g., two or more) in eukaryotic cells and multicellular organisms. The present invention contemplates several methods for creating mutations in the tumor suppressor gene(s). In one embodiment the mutation is an insertion mutation. In another embodiment the mutation is a deletion mutation. In another embodiment the method of mutation is the introduction of a cassette or gene trap by recombination. In another embodiment a small nucleic acid sequence change is created by mutagenesis (through the creation of frame shifts, stop mutations, substitution mutations, small insertions mutations, small deletion mutations, and the like). In yet another embodiment, a transgene is delivered to knockout or knockdown the products of the tumor-suppressor gene (mRNA or protein) in trans.

The invention also is directed to insertional mutagens for making the mutant cells and organisms, and which also can be used to analyze the mutations that are made in the cells and organisms. The invention also is directed to methods in which one or more mutated genes is tagged by a tag provided by the insertional mutagen to allow the detection, selection, isolation, and manipulation of a cell with a genome tagged by the insertional mutagen and allows the identification and isolation of the mutated gene(s). The invention provides methods for making multiple mutations (i.e., mutations in two or more genes that produce a phenotype cumulatively) in cells and organisms and tagging at least one of the mutated genes such that the mutation can be rapidly identified.

The term gene disruption as used herein refers to a gene knock-out or knock-down in which an insertional mutagen is integrated into an endogenous gene thereby resulting expression of a fusion transcript between endogenous exons and sequences in the insertional mutagen.

In one embodiment, the invention provides for insertional mutagenesis involving the integration of one or more polynucleotide sequences into the genome of a cell or organism to mutate one or more endogenous genes in the cell or organism. Thus, the insertional mutagenic polynucleotides of the present invention are designed to mutate one or more endogenous genes when the polynucleotides integrate into the genome of the cell.

Accordingly, the insertional mutagens used in the present invention can comprise any nucleotide sequence capable of altering gene expression levels or activity of a gene product upon insertion into DNA that contains the gene. The insertional mutagens can be any polynucleotide, including DNA and RNA, or hybrids of DNA and RNA, and can be single-stranded or double-stranded, naturally occurring or non-naturally occurring (e.g., phosphorothioate, peptide-nucleic acids, etc.). The insertional mutagens can be of any geometry, including but not limited to linear, circular, coiled, supercoiled, branched, hairpin, and the like, and can be any length capable of facilitating mutation, and tagging of an endogenous gene. In certain embodiments, the insertional mutagens can comprise one or more nucleotide sequences that provide a desired function.

In another embodiment, the method further involves transforming a cell with a nucleic acid construct comprising donor DNA. An example of donor DNA may include a DNA transposon. Transposable elements are discrete sequences in the genome which are mobile. They have the ability to translocate from one position in the genome to another. Unlike most genetic entities that can create modification to an organism's genome, transposons do not require homology with the recipient genome for insertion. Transposons contain inverted terminal repeats which are recognized by the protein transposase. Transposase facilitates the transposition event. Transposition can occur in replicative (the element is duplicated) or nonreplicative (element moves from one site to another and is conserved) mechanism. Transposons can either contain their own transposase or transposase can be added in trans to facilitate transposition. The transposon promotes genetic modifications in many ways. The insertion itself may cause genetic modification by disruption of a DNA sequence or introduction of DNA. The transposon may be used to deliver a gene trap.

In another embodiment, the method for mutagenesis involves transforming a cell with nucleic acid by use of a LTR retrotransposon with reverse transcriptase. The retrotransposon is initially composed of a single strand of RNA. This single stranded RNA is converted into a double stranded DNA by reverse transcriptase. This is a linear duplex of DNA is integrated into the host's genome by the enzyme integrase. This insertion event is much like a transposition event and can be engineered to genetically modify a host's genome.

In another embodiment, the method for mutageneis is a non-LTR retrotransposon. Long Interspersed Nucleotide Elements (LINEs) are retrotransposons that do not have long terminal repeats (LTR's). The LINES open reading frame 1 (ORF1) is a DNA binding protein, ORF2 provides both reverse transcriptase and endonuclease activity. The nick provides the 3'-OH end required for priming the synthesis of cDNA on the RNA template by reverse transcriptase. A second cleavage site opens the other strand of DNA. The RNA/DNA hybrid integrates into the host genome before or after converting into double stranded DNA.

In another embodiment a retrovirus may be used for insertional genetic modification. The retroviral vector (e.g. lentivirus) inserts itself into the genome. The vector can carry a transgene or can be used for insertional mutagenesis. The infected embryos are then injected into a receptive female. The female gives birth to founder animals which have genetic modifications in their germline. Genetically modified lines are established with these founder animals.

In another embodiment, mutagenesis by recombination of a cassette into the genome may be facilitated by targeting constructs or homologous recombination vectors. Homologous recombination vectors are composed of fragments of DNA which are homologous to target DNA. Recombination between identical sequences in the vector and chromosomal DNA will result in genetic modification. The vector may also contain a selection method (antibiotic resistance or GFP) and a unique restriction enzyme site used for further genetic modification. The targeting vector will insert into the genome at a position (exon, intro, regulatory element) and create genetic modification.

In another embodiment, mutagenesis through recombination of a cassette into the genome may be carried out by Serine and Tyrosine recombinase with the addition of an insertion cassette. Site-specific recombinastion occurs by recombinase protein recognition of DNA, cleavage and rejoining as a phosphodiesterase bond between the serine or tyrosine residues. A cassette of exogenous or endogenous DNA may be recombined into the serine or tyrosine site. The cassette can contain a transgene, gene trap, reporter gene or other exogenous or endogenous DNA.

In one embodiment, the present invention is directed to methods for both targeted (site-specific) DNA insertions and targeted DNA deletions. In one embodiment, the method involves transformation of a cell with a nucleic acid or mRNA construct minimally comprising DNA encoding a chimeric zinc finger nuclease (ZFN), which can be used to create a DNA deletion. In another embodiment, a second DNA construct can be provided that will serve as a template for repair of the cleavage site by homologous recombination. In this embodiment, a DNA insertion may be created. The DNA insertion may contain a gene trap cassette.

The invention also is directed to nucleic acid sequence mutation for making the mutant cells and organisms.

In one embodiment, the method mutagenesis with mutagens such as methane-sulfonic acid ethylester (EMS), N-ethyl-N-nitrosourea (ENU), diepoxyoctane and UV/trimethylpsorlalen to create nucleic acid sequence mutations.

In another embodiment, sequence editing gene therapies are used that involve the delivery of small DNA fragments, hybrid DNA/RNA molecules, and modified DNA polymers to create sequence mismatches and nucleic acid mutations. RNA/DNA hybrids are molecules composed of a central stretch of DNA flanked by short RNA sequences that form hairpin structures. The RNA/DNA hybrids can produce single base-pair substitutions and deletions resulting in nucleotide mutations. Some other sequence editing examples include triplex forming oligonucliotides, small fragment homologous replacement, single stranded DNA oligonucleotides, and adeno associated virus (AAV) vectors.

The invention also is directed to genetic expression modification or mutagenesis may be carried out by delivery of a transgene that works in trans.

In one embodiment, RNA interference (RNAi) may be used to alter the expression of a gene. Single stranded mRNA can be regulated by the presence of sections of double stranded RNA (dsRNA) or small interfering RNA (siRNA). Both anti-sense and sense RNAs can be effective in inhibiting gene expression. siRNA mediates RNA interference and is created by cleavage of long dsDNA by the enzyme Dicer. RNAi can create genetic modification by triggering the degradation of mRNA's that are complementary to either strand of short dsRNA. When siRNA is associated with complementary single stranded RNA it can signal for nuclease to degrade the mRNA. RNAi can also result in RNA silencing which occurs when the short dsRNA inhibits expression of a gene. Other forms of inhibitory RNA, such as small hairpin RNA (shRNA) are envisioned.

In another embodiment, the delivery of a transgene encoding a dominant negative protein may alter the expression of a target gene. Dominant negative proteins can inhibit the activity of an endogenous protein. One example is the expression a protein which contains the ligand binding site of an endogenous protein. The expressed dominant-negative protein "soaks up" all of the available ligand. The endogenous protein is therefore not activated, and the wild type function is knocked out or knocked down.

Other schemes based on these general concepts are within the scope and spirit of the invention, and are readily apparent to those skilled in the art.

The invention also provides methods for making homozygous mutations in rats by breeding a genetically modified rat which is heterozygous for a mutant allele with other genetically modified rat which is heterozygous for the same mutant allele. On average 25% of offspring of such matings are expected to produce animals that are homozygous for the mutant allele. Homozygous mutations are useful for discovering functions associated with the mutated gene.

The present invention is directed generally to reduction or inactivation of gene function or gene expression in cells in vitro and in multicellular organisms. The invention encompasses methods for mutating cells using a one or more mutagens, particularly wherein at least one mutagen is an insertion mutation, a deletion mutation, or a nucleic acid sequence mutation, to achieve homozygous gene mutation or mutation of multiple genes required cumulatively to achieve a phenotype to create knock-outs, knock-downs, and other modifications in the same cell or organism.

The mutation can result in a change in the expression level of a gene or level of activity of a gene product. Activity encompasses all functions of a gene product, e.g. structural, enzymatic, catalytic, allosteric, and signaling. In one embodiment, mutation results in a decrease or elimination of gene expression levels (RNA and/or protein) or a decrease or elimination of gene product activity (RNA and/or protein). Most mutations will decrease the activity of mutated genes. However, both the insertional and physicochemical mutagens can also act to increase or to qualitatively change (e.g. altered substrate on binding specificity, or regulation of protein activity) the activity of the product of the mutated gene. Although mutations will often generate phenotypes that may be difficult to detect, most phenotypically detectable mutations change the level or activity of mutated genes in ways that are deleterious to the cell or organism.

As used herein, decrease means that a given gene has been mutated such that the level of gene expression or level of activity of a gene product in a cell or organism is reduced from that observed in the wild-type or non-mutated cell or organism. This is often accomplished by reducing the amount of mRNA produced from transcription of a gene, or by mutating the mRNA or protein produced from the gene such that the expression product is less abundant or less active.

Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally disclosed nucleic acids.

Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a rat. Also disclosed are animals produced by the process of transfecting a cell within the animal any of the nucleic acid molecules disclosed herein, wherein the mammal is a rat.

Such methods are used to achieve mutation of a single gene to achieve a desired phenotype as well as mutation of multiple genes, required cumulatively to achieve a desired phenotype, in a rat cell or rat. The invention is also directed to methods of identifying one or more mutated genes, made by the methods of the invention, in rat cells and in rats, by means of a tagging property provided by the insertional mutagen(s). The insertional mutagen thus allows identification of one or more genes that are mutated by insertion of the insertional mutagen.

The invention is also directed to rat cells and rats created by the methods of the invention and uses of the rat cells and rats. The invention is also directed to libraries of rat cells created by the methods of the invention and uses of the libraries.

Tumor Suppressor Genes

The invention also features a novel genetically modified rat with a genetically engineered modification in a gene encoding a tumor suppressor protein. In another aspect, the invention features a genetically modified rat, wherein a gene encoding tumor suppressor protein is modified resulting in reduced tumor suppressor protein activity. In preferred embodiments of this aspect, the genetically modified rat is homozygous for the modified gene. In other preferred embodiments, the gene encoding tumor suppressor protein is modified by disruption, and the genetically modified rat has reduced tumor suppressor protein activity. In yet another embodiment, the transgenic rat is heterozygous for the gene modification.

In another embodiment of this aspect of the invention, the invention features a nucleic acid vector comprising nucleic acid capable of undergoing homologous recombination with an endogenous tumor suppressor gene in a cell, wherein the homologous recombination results in a modification of the tumor suppressor gene resulting in decreased tumor suppressor protein activity in the cell. In another aspect, the modification of the tumor suppressor gene is a disruption in the coding sequence of the endogenous tumor suppressor gene.

Another embodiment of this aspect of the invention features a rat cell, wherein the endogenous gene encoding tumor suppressor protein is modified, resulting in reduced tumor suppressor protein activity in the cell.

In certain embodiments, the reduced tumor suppressor protein activity is manifested. In a related aspect, the invention features a rat cell containing an endogenous tumor suppressor gene into which there is integrated a transposon comprising DNA encoding a gene trap and/or a selectable marker.

In another aspect, the invention features a rat cell containing an endogenous tumor suppressor gene into which there is integrated a retrotransposon comprising DNA encoding a gene trap and/or a selectable marker. In another aspect, the invention features a rat cell containing an endogenous tumor suppressor gene into which there is DNA comprising an insertion mutation in the tumor suppressor gene. In another aspect, the invention features a rat cell containing an endogenous tumor suppressor gene into which there is DNA comprising a deletion mutation in the tumor suppressor gene. In another aspect, the invention features a rat cell containing an endogenous tumor suppressor gene in which there has been nucleic acid sequence modification of the tumor suppressor gene.

In another embodiment of the invention, the invention features a method for determining whether a compound is potentially useful for treating or alleviating the symptoms of a tumor suppressor gene disorder, which includes (a) providing a cell that produces a tumor suppressor protein, (b) contacting the cell with the compound, and (c) monitoring the activity of the tumor suppressor protein, such that a change in activity in response to the compound indicates that the compound is potentially useful for treating or alleviating the symptoms of a tumor suppressor gene disorder.

It is understood that simultaneous targeting of more than one gene may be utilized for the development of "knock-out rats" (i.e., rats lacking the expression of a targeted gene product), "knock-in rats" (i.e., rats expressing a fusion protein or a protein encoded by a gene exogenous to the targeted locus), "knock down rats" (i.e., rats with a reduced expression of a targeted gene product), or rats with a targeted gene such that a truncated gene product is expressed.

Rat models that have been genetically modified to alter tumor suppressor expression may be used in in vivo assays to test for activity of a candidate tumor suppressor modulating agent, or to further assess the role of tumor suppressor in a tumor suppressor pathway process such as apoptosis or cell proliferation. Preferably, the altered tumor suppressor expression results in a detectable phenotype, such as decreased or increased levels of cell proliferation, angiogenesis, or apoptosis compared to control animals having normal tumor suppressor expression. The genetically modified rat may additionally have altered tumor suppressor expression (e.g. tumor suppressor knockout). In one embodiment, the genetically modified rats are genetically modified animals having a heterologous nucleic acid sequence present as an extrachromosomal element in a portion of its cells, i.e. mosaic animals (see, for example, techniques described by Jakobovits, 1994, Curr. Biol. 4:761-763) or stably integrated into its germ line DNA (i.e., in the genomic sequence of most or all of its cells). Heterologous nucleic acid is introduced into the germ line of such genetically modified animals by genetic manipulation of, for example, embryos or germ cells or germ cells precursors of the host animal.

Methods of making genetically modified rodents are well-known in the art (see Brinster et al., Proc. Nat. Acad. Sci. USA 82: 4438-4442 (1985), U.S. Pat. Nos. 4,736,866 and 4,870,009, both by Leder et al., U.S. Pat. No. 4,873,191 by Wagner et al., and Hogan, B., Manipulating the Mouse Embryo, Cold Spring Harbor Laboratory Press, Cold Spring Harbor, N.Y., (1986); for particle bombardment see U.S. Pat. No. 4,945,050, by Sandford et al.; for genetically modified *Drosophila* see Rubin and Spradling, Science (1982) 218:348-53 and U.S. Pat. No. 4,670,388; for genetically modified insects see Berghammer A. J. et al., A Universal Marker for Genetically modified Insects (1999) Nature 402:370-371; for genetically modified Zebrafish see Lin S., Genetically modified Zebrafish, Methods Mol Biol. (2000); 136:375-3830); for microinjection procedures for fish, amphibian eggs and birds see Houdebine and Chourrout, Experientia (1991) 47:897-905; Hammer et al., Cell (1990) 63:1099-1112; and for culturing of embryonic stem (ES) cells and the subsequent production of genetically modified animals by the introduction of DNA into ES cells using methods such as electroporation, calcium phosphate/DNA precipitation and direct injection see, e.g., *Teratocarcinomas* and Embryonic Stem Cells, A Practical Approach, E. J. Robertson, ed., IRL Press (1987)). Clones of the nonhuman genetically modified animals can be produced according to available methods (see Wilmut, I. et al. (1997) Nature 385:810-813; and PCT International Publication Nos. WO 97/07668 and WO 97/07669).

In one embodiment, the genetically modified rat is a "knock-out" animal having a heterozygous or homozygous alteration in the sequence of an endogenous tumor suppressor gene that results in a decrease of tumor suppressor function, preferably such that tumor suppressor expression is undetectable or insignificant. Knock-out animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the genetically modified host species. For example, a mouse tumor suppressor gene is used to construct a homologous recombination vector suitable for altering an endogenous tumor suppressor gene in the mouse genome. Detailed methodologies for homologous recombination in rodents are available (see Capecchi, Science (1989) 244: 1288-1292; Joyner et al., Nature (1989) 338:153-156). Procedures for the production of non-rodent genetically modified mammals and other animals are also available (Houdebine and Chourrout, supra; Pursel et al., Science (1989) 244:1281-1288; Simms et al., Bio/Technology (1988) 6:179-183). In a preferred embodiment, knock-out animals, such as rats harboring a knockout of a specific gene, may be used to produce antibodies against the human counterpart of the gene that has been knocked out (Claesson M H et al., (1994) Scan J Immunol 40:257-264; Declerck P J et al., (1995) J Biol Chem. 270:8397-400).

In another embodiment, the genetically modified rat is a "knock-down" animal having an alteration in its genome that results in altered expression (e.g., decreased expression) of the tumor suppressor gene, e.g., by introduction of mutations to the tumor suppressor gene, or by operatively inserting a regulatory sequence that provides for altered expression of an endogenous copy of the tumor suppressor gene.

Genetically modified rats can also be produced that contain selected systems allowing for regulated expression of the transgene. One example of such a system that may be produced is the cre/loxP recombinase system of bacteriophage P1 (Lakso et al., PNAS (1992) 89:6232-6236; U.S. Pat. No. 4,959,317). If a cre/loxP recombinase system is used to regulate expression of the transgene, animals containing transgenes encoding both the Cre recombinase and a selected protein are required. Such animals can be provided through the construction of "double" genetically modified animals, e.g., by mating two genetically modified animals, one containing a transgene encoding a selected protein and the other containing a transgene encoding a recombinase. Another example of a recombinase system is the FLP recombinase system of Saccharomyces cerevisiae (O'Gorman et al. (1991) Science 251:1351-1355; U.S. Pat. No. 5,654,182). In a preferred embodiment, both Cre-LoxP and Flp-Frt are used in the same system to regulate expression of the transgene, and for sequential deletion of vector sequences in the same cell (Sun X et al (2000) Nat Genet 25:83-6).

The genetically modified rats can be used in genetic studies to further elucidate the tumor suppressor pathway, as animal models of disease and disorders implicating defective tumor suppressor function, and for in vivo testing of candidate therapeutic agents, such as those identified in screens described below. The candidate therapeutic agents are administered to a genetically modified animal having altered tumor suppressor function and phenotypic changes are compared with appropriate control animals such as genetically modified animals that receive placebo treatment, and/or animals with unaltered tumor suppressor expression that receive candidate therapeutic agent.

The invention also features novel genetically modified animals with a genetically engineered modification in the gene encoding tumor suppressor proteins. In one aspect, the invention features a genetically modified non-human mammal, wherein a gene encoding tumor suppressor gene is provided as follows:

Roundabout, Axon Guidance Receptor, Homolog 1 (Robo1)

The Robo1 gene is a receptor and member of the neural cell adhesion family. Robo1 is involved in axon guidance and binds directly to the netrin receptor Deleted in colorectal carcinoma (Dcc). In humans mutations in Robo1 increase the susceptibility to develop breast cancer, renal cell carcinoma, and non-small cell lung cancer. Robo1 knockout mice display bronchial epithelial abnormalities which are associated with early lung cancer.

p53

The p53 gene is a tumor suppressor gene. That is, its activity stops the formation of tumors. If a person inherits only one functional copy of the p53 gene from their parents, they are predisposed to cancer and usually develop several independent tumors in a variety of tissues in early adulthood. This condition is rare, and is known as Li-Fraumeni syndrome. However, mutations in p53 are found in most tumor types, and so contribute to the complex network of molecular events leading to tumor formation.

The human p53 gene has been mapped to chromosome 17. In the cell, p53 protein binds DNA, which in turn stimulates another gene to produce a protein called p21 that interacts with a cell division-stimulating protein (cdk2). When p21 is complexed with cdk2, the cell cannot pass through to the next stage of cell division. Mutant p53 can no longer bind DNA in an effective way, and as a consequence the p21 protein is not made available to act as the 'stop signal' for cell division. Thus cells divide uncontrollably, and form tumors.

Tumor suppressor genes were first identified by making cell hybrids between tumor and normal cells. A chromosome from the normal cell reverted to the transformed phenotype on some occasions. Several familial cancers have been shown to be associated with the loss of function of a tumor suppressor gene. They include the retinoblastoma susceptibility gene (RB), Wilms' tumors (WT1), neurofibromatosis type-1 (NF1), familial adenomatosis polyposis coli (FAP), von Hippel-Lindau syndrome (VHL), and those identified through loss of heterozygosity such as in colorectal carcinomas (called DCC for deleted in colon carcinoma) and p53 which was originally thought to be a proto-oncogene. However, the wild-type p53 protein suppresses the activity of mutant alleles of p53 which are the oncogenic forms of p53.

In humans, loss of heterozygosity at the short arm of chromosome 17 has been associated with tumors of the lung, colon and breast. This region of chromosome 17 includes the p53 gene. The inheritance of a mutated p53 allele is the cause of Li-Fraumeni syndrome (LFS). LFS is a disorder that greatly increases the risk of several types of cancer including sarcomas, breast cancers, acute leukemias and brain tumors. The disorder is named for the two physicians who first recognized and described the syndrome: Frederick Pei Li and Joseph F. Fraumeni, Jr.

The p53 gene was originally discovered because the protein product complexes with the SV40 large T antigen. It was first thought that p53 was a dominant oncogene since cDNA clones isolated from tumor lines were able to cooperate with the RAS oncogene in transformation assays. This proved to be misleading since the cDNA clones used in all these studies were mutated forms of wild-type p53 and cDNAs from normal tissue were later shown to be incapable of RAS co-transformation. The mutant p53 proteins were shown to be altered in stability and conformation as well as binding to hsp70.

The protein encoded by p53 is a nuclear localized phosphoprotein. A domain near the N-terminus of the p53 protein is highly acidic like similar domains found in various transcription factors. When this domain is fused to the DNA-binding domain of the yeast GAL4 protein, the resulting chimera is able to activate transcription from genes containing GAL4 response elements. This suggests that p53 may be involved in transcriptional regulation. In vitro, p53 has been shown to bind DNA that contains at least 2 copies of the motif 5'-PuPuC(A/T)(A/T)GPyPyPy-3'. This sequence motif suggests that p53 may bind to DNA as a tetramer. Binding as a tetrameric complex explains the fact that mutant p53 proteins act in a dominant manner. They are present in complexes with wild type p53 and alter the function of the normal tetramer.

p53 forms a complex with SV40 large T antigen, as well as the E1B transforming protein of adenovirus and E6 protein of human papilloma viruses. Complexing with these tumor antigens increases the stability of the p53 protein. This increased stability of p53 is characteristic of mutant forms found in tumor lines. The complexes of T antigens and p53 render p53 incapable of binding to DNA and inducing transcription. A cellular protein, originally identified in a spontaneous transformed mouse cell line and termed MDM2, has been shown to bind to p53. Complexing of p53 and MDM2 results in loss of p53 mediated trans-activation of gene expression. Significantly, amplification of the MDM2 gene is observed in a significant fraction of most common human sarcomas.

Retinoblastoma (RB)

In the familial form of this disease individuals inherit a mutant, loss of function allele from an affected parent. A subsequent later somatic mutational event inactivates the normal allele resulting in retinoblastoma development. This leads to an apparently dominant mode of inheritance. The requirement for an additional somatic mutational event at the unaffected allele means that penetration of the defect is not always complete.

In sporadic forms of tumors involving the RB locus 2, somatic mutational events must occur, the second of which must occur in the descendants of the cell receiving the first mutation. This combination of mutational events is extremely rare.

The locus of the RB gene in humans, identified cytogenetically, is chromosome 13q14.1. A 4.7 kb RB transcript has been identified (by chromosomal walking and subsequent Northern blotting with genomic DNA probes) and subsequently cloned. The RB gene encompasses 27 exons that span 180 kb of chromosome 13. Two of the introns in this gene are extremely large, 35 kb and 70 kb. The RB RNA encodes a p110 kDa protein (pRB) of 928 amino acids. pRB is a nuclear-localized phosphoprotein. pRB is not detectable in any retinoblastoma cells. However, surprisingly detectable levels of pRB can be found in most proliferating cells even though there are a restricted number of tissues affected by mutations in the RB gene (i.e. retina, bone and connective tissue).

Many different types of mutations can result in loss of RB function. The largest percentage (30%) of retinoblastomas contains large scale deletions. Splicing errors, point mutations and small deletions in the promoter region have also been observed in some retinoblastomas.

The germ line mutations at RB occur predominantly during spermatogenesis, as opposed to oogenesis. However, the somatic mutations occur with equal frequency at the paternal or maternal locus. In contrast, somatic mutations at RB in sporadic osteosarcomas occur preferentially at the paternal locus. This may be the result of genomic imprinting.

The major function of pRB is in the regulation of cell cycle progression. Its ability to regulate the cell cycle correlates to the state of phosphorylation of pRB. Phosphorylation is maximal at the start of S phase and lowest after mitosis and entry into G1. Stimulation of quiescent cells with mitogen induces phosphorylation of pRB, while in contrast, differentiation induces hypophosphorylation of pRB. It is, therefore, the hypophosphorylated form of pRB that suppresses cell proliferation. One of the most significant substrates for phosphorylation by the G1 cyclin-CDK complexes that regulate progression through the cell cycle is pRB. pRB forms a complex with the E2F family of transcription factors, a result of which renders E2F inactive. When pRB is phosphorylated by G1 cyclin-CDK complexes, it is released from E2F allowing E2F to transcriptionally activate genes. In the context of the cell cycle, E2F increases the transcription of the S-phase cyclins as well as leads to increases in its own transcription.

One element in the growth suppressive pathway of pRB involves the MYC gene. Proliferation of keratinocytes by TGF-β is accompanied by suppression of MYC expression. The inhibition of MYC expression can be abrogated by introducing vectors that express the SV40 and adenovirus large T antigens, which bind pRB. Therefore, a link exists between TGF-β, pRB and MYC expression in keratinocytes.

Transformation by the DNA tumor viruses, SV40, adeno, polyoma, human papilloma and BK is accomplished by binding of the transforming proteins of these viruses to pRB when pRB is in the hypophosphorylated (and thus the proliferation inhibitory) state.

Does it help us or hurt us to add a paragraph or two for each known tumor suppressor gene describing the phenotype in mice (or other models)? What about info such as the genetic loci in rats?

Wilms tumor is a form of nephroblastoma. This childhood cancer is the most common form of solid tumor in children with a frequency of approximately 1 in 10,000. In addition, Wilms tumor accounts for 8% of all childhood cancers. The cancer results from the malignant transformation of abnormally persistent renal stem cells. Several different genetic loci have been associated with the development of Wilms tumor with the most prominent being located on chromosome 11. Either one (unilateral) or both (bilateral) kidneys can be involved. Sporadic evolution of Wilms tumors is associated with chromosomal deletions, identified cytogenetically, at both 11p13 and 11p15 in humans. The 11p15 deletions may involve the IGF-2 or c-Ha-RAS loci. There are also familial forms of Wilms tumor that do not involve either locus.

In some patients, the potential Wilms tumor gene at 11p13 is lost as part of a deleted region of about 345 kb. This region contains a single transcription unit identified as WT1 that spans 50-60 kb, contains 10 exons, which undergo alternative splicing resulting in the generation of at least four different WT1 mRNAs. Adding to the complexity and difficulty in assigning a function to the WT1 locus is that, as a consequence of alternative splicing, alternative translational start codon usage and RNA editing, there are at least 24 different isoforms of WT1 protein. Several functional domains have been identified in each of the WT1 proteins. The differences between many of the encoded proteins are not striking, but differential interactions between the WT1 proteins with distinct targets may result some level of differential control. The first hint of the potential function for WT1 came from the identification of four zinc finger domains suggesting it is a transcription factor. Several protein forms have a three amino acid insertion (KTS) between the third and fourth zinc finger domains. Additional forms have an additional 17 amino acid sequence in exon 5 due to alternative splicing. There is a potential leucine zipper motif in the center of the protein indicating that WT1 may associate with other leucine zipper containing proteins. The NH2-terminal 180 amino acids are involved in self-association. The WT1 proteins can act as transcriptional activators or repressors dependent upon the cellular or chromosomal context.

Several other genes or chromosomal regions have been shown to be associated with Wilms tumor and these have been identified as WT2 (chromosome 11p15.5), WT3 (chromosome 16q), WT4 (chromosome 17q12-q21), and WT5 (chromosome 7p15-p11.2). Mutations in BRCA2, glipican-3 (GPC3), and WTX (an X chromosome allele) have also been described in Wilms tumor.

Neurofibromatosis Type 1 (NF1)

All cases of neurofibromatosis in humans arise by inheritance of a mutant allele. Roughly 50% of all affected individuals carry new mutations which appear to arise paternally, possibly reflecting genomic imprinting. Germ line mutations at the NF1 locus result in multiple abnormal melanocytes (café-au-lait spots) and benign neurofibromas. Some patients also develop benign pheochromocytomas and CNS tumors. A small percentage of patients develop neurofibrosarcomas which are likely to be Schwann cell-derived.

Assignment of the NF1 locus in humans to chromosome 17q11.2 was done by linkage studies of affected pedigrees. The NF1 locus is extremely large, as is the transcript encoded by the locus. The mRNA is 11-13 kb and contains a 7.5 kb coding region. The protein encoded is 2485 amino acids and shares striking homology to rasGAP. The NF1 protein has been given the name neurofibromin. Expression of NF1 is observed in all tissues thus far examined.

Development of benign neurofibromas versus malignant neurofibrosarcomas may be the difference between inactivation of one NF1 allele versus both alleles, respectively. However, changes other than at the NF1 locus are clearly indicated in the genesis of neurofibrosarcomas. A consistent loss of genetic material on the short arm of chromosome 17 is seen in neurofibrosarcomas but not neurofibromas. The losses at 17p affect the wild type p53 locus and may be associated with a mutant p53 allele on the other chromosome.

Characterization of the NF1 protein was carried out by generating antibodies against both fusion proteins and synthetic peptides. These antibodies specifically recognize a 220 kDa protein, in both human and rat spinal cord. Neurofibromin is most abundant in the nervous system. Immunostaining of tissue sections indicates that neurons, oligodendrocytes, and nonmyelinating Schwann cells contained neurofibromin, whereas astrocytes and myelinating Schwann cells do not. In schwannoma cell lines from patients with neurofibromatosis, loss of neurofibromin is associated with impaired regulation of the GTP-bound form of the proto-oncogene RAS (GTP-RAS). Analysis of other neural crest-derived tumor cell lines showed that some melanoma and neuroblastoma cell lines established from tumors occurring in patients without neurofibromatosis also contained reduced or undetectable levels of neurofibrom in, with concomitant genetic abnormalities of the NF1 locus. In contrast to the schwannoma cell lines, however, GTP-RAS was appropriately regulated in the melanoma and neuroblastoma lines that were deficient in neurofibromin. These results demonstrate that some neural crest tumors not associated with neurofibromatosis have acquired somatically inactivated NF1 genes and suggested a tumor-suppressor function for neurofibromin that is independent of RAS GTPase activation.

Familial Adenomatosis Polyposis (FAP)

Somatic mutations in the adenomatous polyposis coli (APC) gene appear to initiate colorectal cancer development in the general population. Germ line mutations in the APC gene are responsible for a syndrome called familial adenomatous polyposis (FAP). Mutations in the APC gene exhibit a dominant pattern of inheritance. Multiple colonic polyp development characterizes FAR These polyps arise during the second and third decades of life and become malignant carcinomas and adenomas later in life. Genetic linkage analysis assigned the APC locus to 5q21 in humans. This region of the chromosome is also involved in non-familial forms of colon cancer. FAP adenomas appear as a result of loss-of-function mutations to the APC gene. This is characteristic of tumor suppressors.

Identification of the APC gene was aided by the observation that two patients contained deletions at the locus spanning 100 kb of DNA. Three candidate genes in this region, DP1, SRP19 and DP2.5 were examined for mutations that could be involved in APC. The DP2.5 gene has sustained 4 distinct mutations specific to APC patients indicating this to be the APC gene. To date, more than 120 different germ line and somatic mutations have been identified in the APC gene. The vast majority of these mutations lead to COOH-terminal truncation of the APC protein.

In humans, the APC gene contains 15 exons, spanning approximately 125 kb of DNA. Northern blotting detects RNA of around 10 kb. An alternative form of exon 9 (9A) was also found that splices into the interior of exon 9, removing 101 amino acids from the full length APC transcript. The protein coding region of the APC gene is also extremely large encompassing 2844 amino acids. No similarities to known proteins were found, except for several stretches of sequence related to intermediate filament proteins.

Using antibodies specific for the NH2-terminus of APC, it is possible to co-precipitate additional APC-associated proteins. One of these APC-associated proteins is β-catenin. The catenins are a family of proteins that interact with the cytoplasmic portion of the cadherins (cell-cell adhesion family of proteins), thus linking the cadherins to the actin cytoskeleton.

Catenins are equally important in the signaling cascade initiated by the

Wnt family of proteins, which are involved in embryonic patterning and development of the nervous system. The Wnt proteins are secreted factors that interact with cell-surface receptors. Wnt-receptor interaction induces the activity of the cytoplasmic phosphoprotein "disheveled". Activated disheveled protein inhibits the serine/threonine kinase glycogen synthase kinase-3P (GSK-3P). When GSK-3β is inhibited, β-catenin becomes hypophosphorylated. The hypophosphorylated form of β-catenin migrates to the nucleus and interacts with transcription factors (in particular with T-cell factor/lymphoid enhancer-binding factor-1 (TCF/LEF-1), thereby inducing expression of various genes. The suspected role of APC in this pathway is to bind phosphorylated β-catenin. The APC-β-catenin complex stimulates the breakdown of β-catenin. Therefore, mutations which lead to a loss of APC, or to a loss of the portion of the APC protein that interacts with β-catenin, would lead to constitutive activation of TCF/LEF-1 and unrestricted growth.

Deleted in Colon Carcinoma (DCC)

Loss of heterozygosity (LOH) on chromosome 18 in humans is frequently observed in colorectal carcinomas (73%) and in advanced adenomas (47%), but only occasionally in earlier-stage adenomas (11 to 13%). The area of chromosome 18 which is observed to be lost resides between 18q21.3 and the telomere. A 370 kb stretch of DNA from the region of 18q suspected to contain a tumor suppressor gene was cloned. Expressed exons were used as probes for screening cDNA libraries to obtain clones that encoded a gene which was given the name DCC (deleted in colorectal carcinomas). A YAC contig, containing the entire DCC coding region, has been characterized showing that the DCC gene spans approximately 1.4 Mbp and contains 29 exons.

The expression of the DCC gene has been detected in most normal tissues, including colonic mucosa. Somatic mutations have been observed within the DCC gene in colorectal cancers. The types of mutations observed included a homozygous deletion of the 5' end, a point mutation within one of the introns, and 10 examples of DNA insertions within a 170 bp fragment immediately downstream of one of the exons.

Evaluation of sporadic colon cancers for allelic deletions defined an area of chromosome 18 that included two candidate tumor suppressors. One was DPC4 (see Table 1) and the other was DCC. DPC4 is deleted in up to one-third of cases of sporadic colon cancer assayed and DCC, or a closely linked gene, was deleted in the remaining tumors. Tumor suppressor genes located on chromosome 17p and 18q are critically involved in the development of most gastric cancers. Involvement of DCC may be rather selective for gastrointestinal cancers. Loss of DCC gene expression is also an important factor in the development or progress of pancreatic adenocarcinoma.

The DCC protein is a transmembrane protein of the immunoglobulin superfamily and has structural features in common with certain types of cell-adhesion molecules, including neural-cell adhesion molecule (N-CAM). It is known that the establishment of neuronal connections requires the accurate guidance of developing axons to their targets. This guidance process involves both attractive and repulsive cues in the extracellular environment. The netrins and semaphorins are proteins that can function as diffusible attractants or repellents for developing neurons. However, the receptors and signal transduction mechanisms through which they produce their effects are poorly understood. Netrins are chemoattractants for commissural axons in the vertebral spinal cord. Recent work has shown that DCC is expressed on spinal commissural axons and possesses netrin-1-binding activity. This suggests that DCC is a receptor or a component of a receptor that mediates the effects of netrin-1 on commissural axons. Genetic evidence showing an interaction between DCC and netrin homologs in *C. elegans* (the UNC-40 protein) and *Drosophila melanogaster* (the frazzled protein) supports the role of DCC as a receptor in the axonal guidance pathway. Mice carrying a null allele of DCC harbor defects in axonal projections that are similar to those seen in netrin-1-deficient mice, further supporting the interaction between DCC and axon development.

von Hippel-Lindau Syndrome (VHL)

Individuals afflicted with von Hipplel-Lindau syndrome (VHL) inherit one normal copy and one mutant copy of the VHL gene. As a consequence of somatic mutation or loss of the normal VHL gene, individuals are predisposed to a wide array of tumors that include renal cell carcinomas, retinal angiomas, cerebellar hemangioblastomas and pheochromocytomas. In addition, some individuals with VHL sustain somatic alterations to both wild-type genes. This latter phenomenon is evident in the majority of sporadic clear cell renal carcinomas.

One characteristic feature of tumors from VHL patients is the high degree of vascularization, primarily as a result of the constitutive expression of the vascular endothelial growth factor (VEGF) gene. Many of the hypoxia-inducible factor (HIF) controlled genes are also constitutively expressed in these tumors whether or not high oxygen levels are present. In addition, the VHL gene has been shown to be required for cells to exit out of the cell cycle during nutrient depletion.

The role of the protein encoded by the VHL locus (pVHL) has been deduced from studies on the alterations in HIF control of hypoxia-inducible genes in VHL tumors. HIF is composed of an α-subunit and a β-subunit. The α-subunit is encoded by one of three genes (HIF1α, HIF2α, and HIF3α). The β-subunit (HIF1β) is also known as the aryl hydrocarbon receptor nuclear translocator, ARNT. Normally the HIFα subunits are degraded in the presence of oxygen due to the regulated addition of multiple ubiquitin molecules. Polyubiquitination is a key modification directing proteins for rapid degradation by the proteosome machinery. Cells lacking pVHL do not ubiquitinate HIF1α. These observations led to the identification that pVHL was a component of a ubiquitin ligase complex that is responsible for polyubinitination of HIF1α subunits.

The invention also features novel genetically modified cells and animals with a genetically modified modification in a gene encoding tumor suppressor proteins. In one aspect, the invention features genetically modified rat cells or rats, wherein a gene modification occurs in a gene encoding a tumor suppressor gene provide in Table 1

TABLE 1

| Tumor Suppressor Gene | Function | Rat Chromosomal Location |
|---|---|---|
| p53 | cell cycle regulation, apoptosis | 10q4 |
| RB1 | cell cycle regulation | 15q2 |
| WT1 | transcriptional regulation | 3q32 |
| NF1, protein; neurofibromin 1 | catalysis of RAS inactivation | 10q24 |
| NF2, protein; merlin or neurofibromin 2 | linkage of cell membrane to actin cytoskeleton | 14q21 |
| APC | signaling through adhesion molecules to nucleus | 18p12 |
| TSC1, protein; hamartin | forms complex with TSC2 protein, inhibits signaling to downstream effectors of mTOR | 3p12 |

TABLE 1-continued

| Tumor Suppressor Gene | Function | Rat Chromosomal Location |
|---|---|---|
| TSC2, protein; tuberin | see TSC1 above | 10q12 |
| DPC4, also known as SMAD4 | regulation of TGF-β/BMP signal transduction | 18q21.1 |
| DCC | transmembrane receptor involved in axonal guidance via netrins | 18q12.2 |
| BRCA1 | cell cycle control, controlling protein degradation, DNA damage repair, and transcriptional regulation; interacts with Rad51 in DNA repair | 10q32.1 |
| BRCA2 | transcriptional regulation of genes involved in DNA repair and homologous recombination | 12p12 |
| PTEN | phosphoinositide 3-phosphatase, protein tyrosine phosphatase | Chromosome 1 236771027 . . . 236837261 |
| LKB1, a nuclear localized kinase, also called STK11 (serine-threonine kinase 11) | phosphorylates and activates AMP-activated kinase (AMPK), AMPK involved in stress responses, lipid and glucose metabolism | 7q11 |
| MSH2 | DNA mismatch repair | 6q12 |
| MLH1 | DNA mismatch repair | 8q32 |
| CDH1, protein; E-cadherin | cell-cell adhesion protein | 19q12 |
| VHL | regulation of transcription elongation through activation of a ubiquitin ligase complex | 4q41.3-q42.1 |
| p16INK4α, also called CDKN2A, protein; cyclin-dependent kinase inhibitor 2A | cell-cycle regulation | 5q32 |
| PTCH, protein; patched | transmembrane receptor for sonic hedgehog (shh), involved in early development through repression of action of smoothened | 17q14 |
| MEN1 | intrastrand DNA crosslink repair | 1q43 |
| E2F1 | cell cycle and action of tumor suppressor proteins and is also a target of the transforming proteins of small DNA tumor viruses | 3q41 |
| CHEK2 | DNA damage, replication, cell cycle progression | 12q16 |
| CASP7 | execution-phase of cell apoptosis | 1q55 |
| CDKN1A | Regulator of cell cycle progression at G1 | Chromosome 17 |
| SMARCB1 | Relives chromatin structures and regulation of transcriptional machinery | 20q12 |
| BRAF | Regulating the MAP kinase/ERKs signaling pathway, which affects cell division, differentiation, and secretion | 4q21-q22 |
| KIT | Type 3 transmembrane receptor for MGF (mast cell growth factor, also known as stem cell factor | |
| RET | Cell-surface molecules that transduce signals for cell growth and differentiation | 4q42 |
| CASP3 | Execution phase apoptosis | 16q11 |
| EGFR | Induces receptor dimerization and tyrosine autophosphorylation and leads to cell proliferation | 14q22 |
| JUN | Specific target DNA sequences to regulate gene expression | 5q34.1 |
| GSTM1 | Class of enzymes functions in the detoxification of electrophilic compounds, including carcinogens, therapeutic drugs, environmental toxins and products of oxidative stress, by conjugation with glutathione. | 2q34 |
| GSTT1 | Catalyze the conjugation of reduced glutathione to a variety of electrophilic and hydrophobic compounds | 20p12 |
| MTHFR | Conversion of 5,10-methylenetetrahydrofolate to 5-methyltetrahydrofolate | 5q36 |
| GSTP1 | Detoxification by catalyzing the conjugation of many hydrophobic and electrophilic compounds with reduced glutathione | 1q42 |
| CYP1A1 | Expression is induced by some polycyclic aromatic hydrocarbons (PAHs) | 8q24 |
| XRCC1 | Repair of DNA single-strand breaks formed by exposure to ionizing radiation and alkylating agents | 1q21 |
| ERCC2 | Excision repair | 1q21 |
| NAT2 | Activate and deactivate arylamine and hydrazine drugs and carcinogens | 16p14 |
| TNF | multifunctional proinflammatory cytokine | 20p12 |
| IL1B | Cytokine is produced by activated macrophages as a proprotein | 3q36 |
| IL10 | Cytokine produced primarily by monocytes and to a lesser extent by lymphocytes | 13q13 |
| AR | Steroid-hormone activated transcription factor | Xq22q32 |
| PI3KCG | Modulation of extracellular signaling | 6q16 |
| AKT1 | Suppression of apoptosis | 6q32 |
| FAS (Cd95) | Programmed cell death | 1q52 |
| ST5 | Suppression of tumorigenicity | 1q33 |
| ST7 | Suppression of tumorigenicity | 4q21 |
| ST14 | Suppression of tumorigenicity | 8q13 |
| MSH6 | Recognition of mismatched nucleotides | 6q12 |
| WT1 | Transcription factor control, Wilm's tumor | 3q32 |
| STK11 | Regulation of cell polarity | 7q11 |

Methods

The methods used in the present invention are comprised of a combination of genetic introduction methods, genetic modification or mutagenesis mechanisms, and vector delivery methods. For all genetic modification or mutagenesis mechanisms one or more introduction and delivery method may be employed. The invention may include but is not limited to the methods described below.

Genetic Introduction Methods

In one introduction method, the tumor suppressor gene is mutated directly in the germ cells of an adult animal. This method usually involves the creation of a transgenic founder animal by pronuclear injection. Rat oocytes are microinjected with DNA into the male pronucleus before nuclear fusion. The microinjected DNA creates a transgenic founder rat. In this method, a female rat is mated and the fertilized eggs are flushed from their oviducts. After entry of the sperm into the egg, the male and female pronuclei are separate entities until nuclear fusion occurs. The male pronucleus is larger are can be identified via dissecting microscope. The egg can be held in place by micromanipulation using a holding pipette. The male pronucleus is then microinjected with DNA that can be genetically modified. The microinjected eggs are then implanted into a surrogate pseudopregnant female which was mated with a vasectomized male for uterus preparation. The foster mother gives birth to transgenic founder animals. If the transgenic DNA encodes the appropriate components of a mutagenesis system, such as transposase and a DNA transposon, then mutagenesis will occur directly in the germ cells of founder animals and some offspring will contain new mutations. Chemical mutagenesis can also be used to cause direct germ line mutations.

In another introduction method, the tumor suppressor gene is mutated in the early embryo of a developing animal. The mutant embryonic cells develop to constitute the germ cells of the organism, thereby creating a stable and heritable mutation. Several forms of mutageneis mechanisms can be introduced this way including, but not limited to, zinc finger nucleases and delivery of gene traps by a retrovirus.

In another introduction method, the tumor-suppressor gene is mutated in a pluripotent cell. These pluripotent cells can proliferate in cell culture and be genetically modified without affecting their ability to differentiate into other cell types including germ line cells. Genetically modified pluripotent cells from a donor are microinjected into a recipient blastocyst, or in the case of spermatogonial stem cells can be injected into the rete testis of a recipient animal. Recipient genetically modified blastocysts are implanted into pseudopregnant surrogate females. The progeny which have a genetic modification to the germ line can then be established, and lines homozygous for the genetic modification can be produced by interbreeding.

In another introduction method, the tumor-suppressor gene is mutated in a somatic cell and then used to create a genetically modified animal by somatic cell nuclear transfer. Somatic cell nuclear transfer uses embryonic, fetal, or adult donor cells which are isolated, cultured, and/or modified to establish a cell line. Individual donor cells are fused to an enucleated oocyte. The fused cells are cultured to blastocyst stage, and then transplanted into the uterus of a pseudopregnant female. Alternatively the nucleus of the donor cell can be injected directly into the enucleated oocyte. See U.S. Appl. Publ. No. 20070209083.

Genetic Modification Methods

Mobile DNA Technology

DNA transposons are discrete mobile DNA segments that are common constituents of plasmid, virus, and bacterial chromosomes. These elements are detected by their ability to transpose self-encoded phenotypic traits from one replicon to another, or to transpose to a known gene and inactivate it. Transposons, or transposable elements, include a piece of nucleic acid bounded by repeat sequences. Active transposons encode enzymes (transposases) that facilitate the insertion of the nucleic acid into DNA sequences.

The lifecycle and insertional mutagenesis of DNA transposon sleeping beauty (SB) is depicted in FIG. 1. In its lifecycle, the SB encodes a transposase protein. That transposase recognizes the inverted terminal repeats (ITRs) that flank the SB transposon. The transposase then excises SB and reintegrates it into another region of the genome. Mutagenesis via sleeping beauty is depicted. The mechanism is similar to the life cycle, but transposase is not encoded by the transposon, but instead is encoded elsewhere in the genome The sleeping beauty (SB) mutagenesis breeding and screening scheme is depicted in FIG. 2. One rat referred to as the "driver" rat contains the (SB) transposase within its genome. A second rat, the "donor" rat contains the transposon which has the transposase recognizable inverted terminal repeats (ITRs). The two rats are bred to create the "seed" rat which has an active transposon containing transposase and ITRs. The transposon recognizes the ITRs, excises the transposon, and inserts the it elsewhere in the rat's genome. This insertion event often disrupts coding, regulatory, and other functional regions in the genome to create knockout rat models. The "seed" rat is bred with wild type rats which beget heterozygous G1 mutants. If the transposon has inserted into the genome the event will be recorded via size comparison of DNA by Southern blot analysis. The exact location of the transposon insertion is determined by PCR sequencing of the flanking endogenous rat genome, producing a sequence tag.

The sequences for the DNA transposons sleeping beauty (SB) piggyback (PG) functional domains are shown in FIG. 3. The SB and PB transposase (SB and PB Tpase) sequences encode the protein that recognizes the ITRs and carries out the excision and re-integration. The 3' and 5' ITRs are the flanking sequences which the respective transposases recognizes in order to carry out excision and reintegration elsewhere in the genome.

Figure 4:
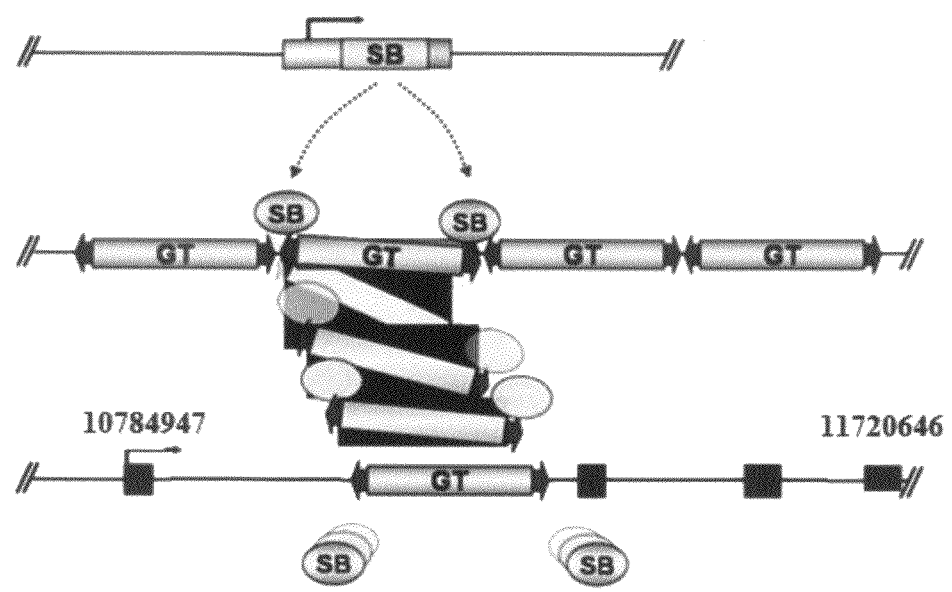

The DNA transposon sleeping beauty (SB) was used by the inventors to create a knockout rat in the Robo1 gene. The mechanism is depicted in FIG. 4, and is the same as that described above. The transposase is encoded, and the protein recognizes the ITRs of the transposon, The transposon is then excised and reinserted into the second intron of the rat Robo1 gene which resides on chromosome 11, location 11p11 between base pairs 11280254 and 11280285.

In another embodiment, the present invention utilizes the transposon piggyBac, and sequence configurations outside of piggyBac, for use as a mobile genetic element as described in U.S. Pat. No. 6,962,810. The Lepidopteran transposon piggyBac is capable of moving within the genomes of a wide variety of species, and is gaining prominence as a useful gene transduction vector. The transposon structure includes a complex repeat configuration consisting of an internal repeat (IR), a spacer, and a terminal repeat (TR) at both ends, and a single open reading frame encoding a transposase.

The Lepidopteran transposable element piggyBac transposes via a unique cut-and-paste mechanism, inserting exclusively at 5' TTAA 3' target sites that are duplicated upon insertion, and excising precisely, leaving no footprint (Elick et al., 1996b; Fraser et al., 1996; Wang and Fraser 1993).

In another embodiment, the present invention utilizes the Sleeping

Beauty transposon system for genome manipulation as described, for example, in U.S. Pat. No. 7,148,203. In one embodiment, the system utilizes synthetic, salmonid-type Tel-like transposases (SB) with recognition sites that facilitate transposition. The transposase binds to two binding-sites within the inverted repeats of salmonid elements, and appears to be substrate-specific, which could prevent cross-mobilization between closely related subfamilies of fish elements.

In another aspect of this invention, the invention relates to a transposon gene transfer system to introduce DNA into the DNA of a cell comprising: a nucleic acid fragment comprising a nucleic acid sequence positioned between at least two inverted repeats wherein the inverted repeats can bind to an SB protein and wherein the nucleic acid fragment is capable of integrating into DNA of a cell; and a transposase or nucleic acid encoding a transposase. In one embodiment, the transposase is provided to the cell as a protein and in another the transposase is provided to the cell as nucleic acid. In one embodiment the nucleic acid is RNA and in another the nucleic acid is DNA. In yet another embodiment, the nucleic acid encoding the transposase is integrated into the genome of the cell. The nucleic acid fragment can be part of a plasmid or a recombinant viral vector. Preferably, the nucleic acid sequence comprises at least a portion of an open reading frame and also preferably, the nucleic acid sequence comprises at least a regulatory region of a gene. In one embodiment the regulatory region is a transcriptional regulatory region and the regulatory region is selected from the group consisting of a promoter, an enhancer, a silencer, a locus-control region, and a border element. In another embodiment, the nucleic acid sequence comprises a promoter operably linked to at least a portion of an open reading frame.

In the transgene flanked by the terminal repeats, the terminal repeats can be derived from one or more known transposons. Examples of transposons include, but are not limited to the following: Sleeping Beauty (Izsvak Z, Ivies Z. and Plasterk R H. (2000) Sleeping Beauty, a wide host-range transposon vector for genetic transformation in vertebrates. J. Mol. Biol. 302:93-102), mos1 (Bessereau J L, et al. (2001) Mobilization of a *Drosophila* transposon in the *Caenorhabditis elegans* germ line. Nature. 413(6851):70-4; Zhang L, et al. (2001) DNA-binding activity and subunit interaction of the mariner transposase. Nucleic Acids Res. 29(17):3566-75, piggybac (Tamura T. et al. Germ line transformation of the silkworm Bombyx mori L. using a piggyBac transposon-derived vector. Nat Biotechnol. 2000 January; 18(1):81-4), Himar1 (Lampe D J, et al. (1998) Factors affecting transposition of the Himar1 mariner transposon in vitro. Genetics. 149(11):179-87), Hermes, To12 element, Pokey, Tn5 (Bhasin A, et al. (2000) Characterization of a Tn5 pre-cleavage synaptic complex. J Mol Biol 302:49-63), Tn7 (Kuduvalli P N, Rao J E, Craig N L. (2001) Target DNA structure plays a critical role in Tn7 transposition. EMBO J 20:924-932), Tn916 (Marra D, Scott J R. (1999) Regulation of excision of the conjugative transposon Tn916. Mol Microbiol 2:609-621), Tc1/mariner (Izsvak Z, Ivies Z4 Hackett P B. (1995) Characterization of a Tc-1 like transposable element in zebrafish (Danio rerio). Mol. Gen. Genet. 247:312-322), Minos and S elements (Franz G and Savakis C. (1991) Minos, a new transposable element from *Drosophila hydci*, is a member of the Tc1-like family of transposons. Nucl. Acids Res. 19:6646; Merriman P J, Grimes C D, Ambroziak J, Hackett D A, Skinner P, and Simmons M J. (1995) S elements: a family of Tc1-like transposons in the genome of *Drosophila melanogaster*. Genetics 141:1425-1438), Quetzal elements (Ke Z, Grossman G L, Cornel A J, Collins F H. (1996) Quetzal: a transposon of the Tc1 family in the mosquito Anopheles albimanus. Genetica 98:141-147); Txr elements (Lam W L, Seo P, Robison K, Virk S, and Gilbert W. (1996) Discovery of amphibian Tc1-like transposon families. J Mol Biol 257:359-366), Tc1-like transposon subfamilies (Ivies Z, Izsvak Z, Minter A, Hackett P B. (1996) Identification of functional domains and evolution of Tc1-like transposable elements. Proc. Natl. Acad Sci USA 93: 5008-5013), Tc3 (Tu Z. Shao H. (2002) Intra- and inter-specific diversity of Tc-3 like transposons in nematodes and insects and implications for their evolution and transposition. Gene 282:133-142), ICESt1 (Burrus V et al. (2002) The ICESt1 element of *Streptococcus thermophilus* belongs to a large family of integrative and conjugative elements that exchange modules and change their specificity of integration. Plasmid. 48(2): 77-97), maT, and P-element (Rubin G M and Spradling A C. (1983) Vectors for P element mediated gene transfer in *Drosophila*. Nucleic Acids Res. 11:6341-6351). These references are incorporated herein by reference in their entirety for their teaching of the sequences and uses of transposons and transposon ITRs.

Translocation of Sleeping Beauty (SB) transposon requires specific binding of SB transposase to inverted terminal repeats (ITRs) of about 230 bp at each end of the transposon, which is followed by a cut-and-paste transfer of the transposon into a target DNA sequence. The ITRs contain two imperfect direct repeats (DRs) of about 32 bp. The outer DRs are at the extreme ends of the transposon whereas the inner DRs are located inside the transposon, 165-166 bp from the outer DRs. Cui et al. (J. Mol Biol 318:1221-1235) investigated the roles of the DR elements in transposition. Within the 1286-bp element, the essential regions are contained in the intervals bounded by coordinates 229-586, 735-765, and 939-1066, numbering in base pairs from the extreme 5' end of the element. These regions may contain sequences that are necessary for transposase binding or that are needed to maintain proper spacing between binding sites.

Transposons are bracketed by terminal inverted repeats that contain binding sites for the transposase. Elements of the IR/R subgroup of the Tc1/mariner superfamily have a pair of transposase-binding sites at the ends of the 200-250 bp long inverted repeats (IRs) (Izsvak, et al. 1995). The binding sites contain short, 15-20 bp direct repeats (DRs). This characteristic structure can be found in several elements from evolutionarily distant species, such as Minos and S elements in flies (Franz and Savakis, 1991; Merriman et al, 1995), Quetzal elements in mosquitoes (Ke et al, 1996), Txr elements in frogs (Lam et al, 1996) and at least three Tc1-like transposon subfamilies in fish (Ivies et al., 1996), including SB [Sleeping Beauty] and are herein incorporated by reference.

Whereas Tc1 transposons require one binding site for their transposase in each IR, Sleeping Beauty requires two direct repeat (DR) binding sites within each IR, and is therefore classified with Tc3 in an IR/DR subgroup of the Tc1/mariner superfamily (96,97). Sleeping Beauty transposes into TA dinucleotide sites and leaves the Tc1/mariner characteristic footprint, i.e., duplication of the TA, upon excision. The non-viral plasmid vector contains the transgene that is flanked by IR/DR sequences, which act as the binding sites for the transposase. The catalytically active transposase may be expressed from a separate (trans) or same (cis) plasmid system. The transposase binds to the IR/DRs, catalyzes the excision of the flanked transgene, and mediates its integration into the target host genome.

Naturally occurring mobile genetic elements, known as retrotransposons, are also candidates for gene transfer vehicles. This mutagenesis method generally involves the delivery of a gene trap.

Retrotransposons are naturally occurring DNA elements which are found in cells from almost all species of animals, plants and bacteria which have been examined to date. They are capable of being expressed in cells, can be reverse transcribed into an extrachromosomal element and reintegrate into another site in the same genome from which they originated.

Retrotransposons may be grouped into two classes, the retrovirus-like LTR retrotransposons, and the non-LTR elements such as human L1 elements, Neurospora TAD elements (Kinsey, 1990, Genetics 126:317-326), I factors from Drosophila (Bucheton et al., 1984, Cell 38:153-163), and R2Bm from Bombyx mori (Luan et al., 1993, Cell 72: 595-605). These two types of retrotransposon are structurally different and also retrotranspose using radically different mechanisms.

Unlike the LTR retrotransposons, non-LTR elements (also called polyA elements) lack LTRs and instead end with polyA or A-rich sequences. The LTR retrotransposition mechanism is relatively well-understood; in contrast, the mechanism of retrotransposition by non-LTR retrotransposons has just begun to be elucidated (Luan and Eickbush, 1995, Mol. Cell. Biol. 15:3882-3891; Luan et al., 1993, Cell 72:595-605). Non-LTR retrotransposons can be subdivided into sequence-specific and non-sequence-specific types. L1 is of the latter type being found to be inserted in a scattered manner in all human, mouse and other mammalian chromosomes.

Some human L1 elements (also known as a LINEs) can retrotranspose (express, cleave their target site, and reverse transcribe their own RNA using the cleaved target site as a primer) into new sites in the human genome, leading to genetic disorders.

Further included in the invention are DNAs which are useful for the generation of mutations in a cell, which mutations are useful for assessing the frequency with which selected cells undergo insertional mutagenesis for the generation of genetically modified animals and the like. Engineered L1 elements can also be used as retrotransposon mutagens. Sequences can be introduced into the L1 that increases its mutagenic potential or facilitates the cloning of the interrupted gene. DNA sequences useful for this application of the invention include marker DNAs, such as GFP, that are specifically engineered to integrate into genomic DNA at sites which are near to the endogenous genes of the host organism. Other potentially useful DNAs for delivery are regulatory DNA elements, such as promoter sequences, enhancer sequences, retroviral LTR elements and repressors and silencers. In addition, genes which are developmentally regulated are useful in the invention.

Viral Mutagenesis Methods

Viral vectors are often created using a replication defective virus vector with a genome that is partially replaced by the genetic material of interest (e.g. gene trap, selectable marker, and/or a therapeutic gene). The viral vector is produced by using a helper virus to provide some of the viral components that were deleted in the replication defective virus, which results in an infectious recombinant virus whose genome encodes the genetic material of interest. Viral vectors can be used to introduce an insertion mutation into the rat's genome. Integration of the viral genetic material is often carried out by the viral enzyme integrase. Integrase brings the ends of viral DNA together and converts the blunt ends into recessed ends. Integrase created staggered ends on chromosomal DNA. The recessed ends of the viral DNA are then joined with the overhangs of genomic DNA, and the single stranded regions are repaired by cellular mechanisms. Some recombinant virus vectors are equipped with cell uptake, endosomal escape, nuclear import, and expression mechanisms allowing the genetic material of interest to be inserted and expressed in the rat's genome. The genetic material introduced via viral vectors can genetically modify the rat's genome but is not limited to disrupting a gene, inserting a gene to be expressed, and by delivery of interfering RNA. Viral vectors can be used in multiple methods of delivery. The most common mode of delivery is the microinjection of a replication deficient viral vector (e.g. retroviral, adenoviral) into an early embryo (1-4 day) or one cell pronuclear egg. After viral vector delivery the embryo is cultured in vitro and transferred to recipient rats to create genetically modified progeny.

In one embodiment, insertion mutations can be created by delivery of a gene trap vector into the rat genome. The gene trap vector consists of a cassette that contains selectable reporter tags. Upstream from this cassette is a 3' splice acceptor sequence. Downstream from the cassette lays a termination sequence poly adenine repeat tail (polyA).

The splice accepter sequence allows the gene trap vector to be spliced into chromosomal mRNA. The polyA tail signals the premature interruption of the transcription. The result is a truncated mRNA molecule that has decreased function or is completely non-functional. The gene trap method can also be utilized to introduce exogenous DNA into the genome.

In another embodiment an enhancer trap is used for insertional mutagenesis. An enhancer trap is a transposable element vector that carries a weak minimal promoter which controls a reporter gene. When the transposable element is inserted the promoter drives expression of the reporter gene. The expression of the reporter gene also displays the expression patterns of endogenous genes. Enhancer trapping results in genetic modification and can be used for gain-of-function genetics. The Gal4-mediated expression system is an example of an enhancer trap.

Further included are one or more selectable marker genes. Examples of suitable prokaryotic marker genes include, but are not limited to, the ampicillin resistance gene, the kanamycin resistance gene, the gene encoding resistance to chloramphenicol, the lacZ gene and the like. Examples of suitable eukaryotic marker genes include, but are not limited to, the hygromycin resistance gene, the green fluorescent protein (GFP) gene, the neomycin resistance gene, the zeomycin gene, modified cell surface receptors, the extracellular portion of the IgG receptor, composite markers such as .beta.-geo (a lac/neo fusion) and the like.

In one embodiment, the gene trap will need to be integrated into the host genome and an integrating enzyme is needed. Integrating enzymes can be any enzyme with integrating capabilities. Such enzymes are well known in the art and can include but are not limited to transposases, integrases (including DDE transposases), recombinases including but not limited to tyrosine site-specific recombinases (integrase) and other site-specific recombinases (e.g., cre), bacteriophage integrases, retrotransposases, and retroviral integrases.

The integrating enzymes of the present invention can be any enzyme with integrating capabilities. Such enzymes are well known in the art and can include but are not limited to transposases, integrases (including DDE transposases), tyrosine site-specific recombinases (integrase), recombinases, site-specific recombinases (e.g., cre), bacteriophage integrases, integron, retrotransposases, retroviral integrases and terminases.

Disclosed are compositions, wherein the integrating enzyme is a transposase. It is understood and herein contemplated that the transposase of the composition is not limited and to any one transposase and can be selected from at least the group consisting of Sleeping Beauty (SB), Tn7, Tn5, mos1, piggybac, Himar1, Hermes, Tol2 element, Pokey, Minos, S elements, P-element, 1CESt1, Quetzal elements, Tn916, maT, Tc1/mariner and Tc3.

Where the integrating enzyme is a transposase, it is understood that the transposase of the composition is not limited and to any one transposase and can be selected from at least the group consisting of Sleeping Beauty (SB), Tn7, Tn5, Tn916, Tc1/mariner, Minos and S elements, Quetzal elements, Txr elements, maT, mos1, piggybac, Himar1, Hermes, Tol2 element, Pokey, P-element, and Tc3. Additional transposases may be found throughout the art, for example, U.S. Pat. No. 6,225,121, U.S. Pat. No. 6,218,185 U.S. Pat. No. 5,792,924 U.S. Pat. No. 5,719,055, U.S. Patent Application No. 20020028513, and U.S. Patent Application No. 20020016975 and are herein incorporated by reference in their entirety. Since the applicable principal of the invention remains the same, the compositions of the invention can include transposases not yet identified.

Also disclosed are integrating enzymes of the disclosed compositions wherein the enzyme is an integrase. For example, the integrating enzyme can be a bacteriophage integrase. Such integrase can include any bacteriophage integrase and can include but is not limited to lamda bacteriophage and mu bacteriophage, as well as Hong Kong 022 (Cheng Q., et al. Specificity determinants for bacteriophage Hong Kong 022 integrase: analysis of mutants with relaxed core-binding specificities. (2000) Mol Microbiol. 36(2):424-36.), HP1 (Hickman, A. B., et al. (1997). Molecular organization in site-specific recombination: The catalytic domain of bacteriophage HP1 integrase at 2.7 A resolution. Cell 89: 227-237), P4 (Shoemaker, N B, et al. (1996). The Bacteroides mobilizable insertion element, NBU1, integrates into the 3' end of a Leu-tRNA gene and has an integrase that is a member of the lambda integrase family. J Bacteriol. 178(12):3594-600.), P1 (Li Y, and Austin S. (2002) The P1 plasmid in action: time-lapse photomicroscopy reveals some unexpected aspects of plasmid partition. Plasmid. 48(3):174-8.), and T7 (Rezende, L. F., et al. (2002) Essential Amino Acid Residues in the Single-stranded DNA-binding Protein of Bacteriophage T7. Identification of the Dimer Interface. J. Biol. Chem. 277, 50643-50653.). Integrase maintains its activity when fused to other proteins.

Also disclosed are integrating enzymes of the disclosed compositions wherein the enzyme is a recombinase. For example, the recombinase can be a Cre recombinase, Flp recombinase, HIN recombinase, or any other recombinase. Recombinases are well-known in the art. An extensive list of recombinases can be found in Nunes-Duby S E, et al. (1998) Nuc. Acids Res. 26(2): 391-406, which is incorporated herein in its entirety for its teachings on recombinases and their sequences.

Also disclosed are integrating enzymes of the disclosed compositions wherein the enzyme is a retrotransposase. For example, the retrotransposase can be a Gate retrotransposase (Kogan G L, et al. (2003) The GATE retrotransposon in *Drosophila melanogaster*: mobility in heterochromatin and aspects of its expression in germ line tissues. Mol Genet Genomics. 269(2):234-42).

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

Zinc Finger Nucleases

In another method a zinc finger nuclease creates site-specific deletions via double stranded DNA breaks that are repaired by non-homologous end joining (NHEJ). Zinc finger nucleases may also be used to create an insertion mutation by combining the ZFN with a homologously integrating cassette to create an insertion in the genomic DNA. Therefore, this genetic modification method can be used for both targeted (site-specific) DNA insertions and targeted DNA deletions. In one embodiment, the method involves transformation of a cell with a nucleic acid or mRNA construct minimally comprising DNA encoding a chimeric zinc finger nuclease (ZFN), which can be used to create a DNA deletion. In another embodiment, a second DNA construct can be provided that will serve as a template for repair of the cleavage site by homologous recombination. In this embodiment, a DNA insertion may be created. The DNA insertion may contain a gene trap cassette. In one embodiment, this method can be combined with spermatogonial stem cell technology or embryonic stem cell technology, as mentioned above. In another embodiment, this method can be combined with mobile DNA technology. This technique can also be done directly in the rat embryo.

Nucleic Acid Modification Methods

In one embodiment, a random mutation is created with a chemical mutagen and then a screen is performed for insertions in a particular tumor suppressor gene. Chemical mutagens such as methane-sulfonic acid ethylester (EMS), N-ethyl-N-nitrosourea (ENU), diepoxyoctane and UV/trimethylpsorlalen may be employed to create nucleic acid sequence mutations.

Sequence editing gene therapies can also be used that involve the delivery of small DNA fragments, hybrid DNA/RNA molecules, and modified DNA polymers to create sequence mismatches and nucleic acid mutations. RNA/DNA hybrids are molecules composed of a central stretch of DNA flanked by short RNA sequences that form hairpin structures. The RNA/DNA hybrids can produce single base-pair substitutions and deletions resulting in nucleotide imitations. Some other sequence editing examples include triplex forming oligonucleotides, small fragment homologous replacement, single stranded DNA oligonucleotides, and adeno associated virus (AAV) vectors.

The invention also is directed to genetic expression modification or mutagenesis may be carried out by delivery of a transgene that works in trans.

In one genetic modification method, RNA interference may be used to alter the expression of a gene. In another genetic modification method, the delivery of a transgene encoding a dominant negative protein may alter the expression of a target gene.

Vector Delivery Methods

The mutagenesis methods of this invention may be introduced into one or more cells using any of a variety of techniques known in the art such as, but not limited to, microinjection, combining the nucleic acid fragment with lipid vesicles, such as cationic lipid vesicles, particle bombardment, electroporation, DNA condensing reagents (e.g., calcium phosphate, polylysine or polyethyleneimine) or incorporating the nucleic acid fragment into a viral vector and contacting the viral vector with the cell. Where a viral vector is used, the viral vector can include any of a variety of viral vectors known in the art including viral vectors selected from the group consisting of a retroviral vector, an adenovirus vector or an adeno-associated viral vector.

DNA or other genetic material may be delivered through viral and non-viral vectors. These vectors can carry exogenous DNA that is used to genetically modify the genome of the rat. For example Adenovirus (AdV), Adeno-associated virus (AAV), and Retrovirus (RV) which contain LTR regions flanking a gene trap, transgene, cassette or interfering RNA are used to integrate and deliver the genetic material. Another delivery method involves non-viral vectors such as plasmids used for electroporation and cationic lipids used for lipofection. The non-viral vectors usually are engineered to have mechanisms for cell uptake, endosome escape, nuclear import, and expression. An example would be a non-viral vector containing a specific nuclear localization sequence and sequence homology for recombination in a targeted region of the genome. Another aspect of vector delivery is the method by which the vector is delivered to genomic DNA. Some of these methods are microinjection of DNA into early or one cell embryos, pluripotent stem cells, embryonic stem cells, and nuclear transfer.

There are a number of compositions and methods which can be used to deliver nucleic acids to cells, either in vitro or in vivo. For example, the nucleic acids can be delivered through a number of direct delivery systems such as, electroporation, lipofection, calcium phosphate precipitation, plasmids, cosmids, or via transfer of genetic material in cells or carriers such as cationic liposomes. Appropriate means for transfection, including chemical transfectants, or physicomechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed non-viral vectors for example, lipids such as liposomes, such as cationic liposomes (e.g., DOTMA, DOPE, DC-cholesterol) or anionic liposome, or polymersomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. Am. J. Resp. Cell. Mol. Biol. 1:95-100 (1989); Feigner et al. Proc. Natl. Acad. Sci USA 84:7413-7417 (1987); U.S. Pat. No. 4,897, 355. Furthermore, the vector can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

These vectors may be targeted to a particular cell type via antibodies, receptors, or receptor ligands. The following references are examples of the use of this technology to target specific proteins to tumor tissue and are incorporated by reference herein (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129:57-80, (1992); and Roffler, et al., Biochem. Pharmacol, 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue and are incorporated by reference herein (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis have been reviewed (Brown and Greene, DNA and Cell Biology 10:6, 399-409 (1991)).

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can be come integrated into the host genome.

TP53 domains and loss of function mutations

TP53 is a 391 amino acid length protein in rats. The protein contains three essential core domains: DNA-binding, residues 100-290; tetramerisation and oligomerization domain, residues 323-354; transactivation domain, residues 1-47.

Regulatory elements: p53 has two promoters one located 100-250 bp upstream of the first exon, the other is located within the first intron (bp 272-293). There are two transcriptional start sites in exon 1 (bp 1-169), 20 bp downstream.

TP53 splicing: exon1 (bp 1-169) exon2 (bp 170-271) exon 3 (bp 272-293) exon 4 (294-572) STS 1 (bp 300-498) STS 2 (bp 314-572) exon 5 (bp573-756) STS 3 (bp 675-749) exon 6 (bp 757-869) exon 7 (bp 870-979) STS 4 (bp 950-1148) STS 5 (bp 954-1028) exon 8 (bp 980-1116) exon 9 (bp 1117-1190) exon 10 (bp 1191-1297) exon 11 (bp 1298-2589) STS 5 (bp 1449-1565) STS 6 (bp 1906-2052) STS 7 (bp 2441-2517) poly A signal (bp 2550-2555) poly A site (bp2567) coding sequence CDS (bp 198-1379).

Alternate splicing occurs in intron 2 (bp 314-572), and between exons 9 and 10 (bp 1190-1191). Natural variants that occur are a Glycine (G) to Serine (S) variant at position 103, and a Glutamic acid (E) to Glycine (G) at position 256.

Post-translational modifications which are essential for full activity: Acetylation of Lys-303, 371,380: Phosphorylation at Ser-9, 15, 97, 390 by Hipk4, Prpk, Ck2 respectively. Phosphorylation at Thr-18 by Vrk1: Phosphorylation upon UV radiation (for repair) and O-(5'phospho-RNA) Ser-390: Monomethylation of Lys 368, 370.

Loss of function amino acid changes. In one example, a genetically modified rat is created with a disruption within one or more of the following loss of function nucleotide segments:

| Set 1 Amino Acid | Loss of function |
|---|---|
| 273 | A nonsense mutation resulting in substituting a premature stop codon for the Cysteine at position 273 in exon 7. The mutation is within the DNA binding domain and results in a complete loss of Tp53 function |
| 202 | A missense mutation resulting in substituting a Valine for the Glutamic acid at position 202 in exon 6. The mutation is within the DNA binding domain and results in a loss of Tp53 function. |
| 293-354 | Interference with Beta-catenin-dependent TCF signaling. Transactivation of multiple genes including: RGC, WAF1 5', BAX, PIG3 Tetramerisation Downregulation (Vrk1) DNA-binding Growth suppression Dynein binding AP2alpha binding |
| 364-393 | Upregulation (p21wafl) Cell cycle arrest Interference with Beta-catenin-dependent TCF signaling |
| 115-135 | DNA-binding Transactivation of multiple genes including: P53R2, GADD45, CD95-Fas, PCNA, AIP1, PA26, 14-3-3s, RGC, WAF1, MDM2-RE2, MDM2 PUMA, PIG3, BAX, CPT, DOX, Cyclin G Sensitivity to UV-gamma irradiation Upregulation of multiple genes and proteins including: puma, p21wafl, APO, mdm2 |
| 272-286 | Cell cycle arrest Gamma irradiation resistance Transactivation of multiple genes including: RGC, WAF1, BAX, BAI1 NOXA, PA26, PCNA, PIDD, PTGF-beta__FBS01, KILLER/DR5, GML, DNA binding Upregulation of multiple genes and proteins including: p21wafl, GADD45, P53R2 Transrepression of multiple genes and proteins including: C-JUN, C-FOS Growth Suppression |
| 164-194 | Transactivation of multiple genes Loses ability to cooperate with Ras, HPV E7, and other oncogenes in the transformation of primary cells |
| 237-250 | Transactivation of multiple genes Loses ability to cooperate with Ras, HPV E7, and other oncogenes in the transformation of primary cells |
| 102-113 | Transactivation of multiple genes Loses ability to cooperate with Ras, HPV E7, and other oncogenes in the transformation of primary cells |
| 138-163 | Transactivation of multiple genes Loses ability to cooperate with Ras, HPV E7, and other oncogenes in the transformation of primary cells |
| 195-236 | Transactivation of multiple genes Loses ability to cooperate with Ras, HPV E7, and other oncogenes in the transformation of primary cells |
| 250-271 | Transactivation of multiple genes Loses ability to cooperate with Ras, HPV E7, and other oncogenes in the transformation of primary cells |
| 288-291 | Transactivation of multiple genes Loses ability to cooperate with Ras, HPV E7, and other oncogenes in the transformation of primary cells |
| 53-54, 58, 63-100 | Transactivation of multiple genes including: RGC, WAF1, BAX, PIG3, P55CON DNA binding-P55CON Upregulation of multiple genes and proteins including: PIG3, WAF1, CD95-Fas, APAF1, APO |
| 30-49 | Transrepression: HSP70 Transactivation of multiple genes including: WAF1, MDM2, P55CON, RGC, PCNA, Growth Suppression Etoposide sensitivity |
| 14-22 | Transactivation of multiple genes including: P55CON, MDM2, PUMA, AIP1, APO Transrepression of multiple genes including: CMV Cisplatin sensitivity |

| Set 2 Amino Acid | Region description |
|---|---|
| 1-83 | Interaction with HRMT1L2 |
| 1-44 | Transcription activation (acidic) |
| 66-110 | Interaction with WWOX |
| 100-370 | Interaction with HIPK1 |
| 116-292 | Interaction with AXIN1 |
| 241-248 | Interacts with the 53BP2 SH3 domain |
| 256-294 | Interaction with E4F1 |
| 300-393 | Interaction with CARM1 |
| 319-360 | Interaction with HIPK2 |
| 325-356 | Oligomerization |
| 359-363 | Interaction with USP7 |
| 368-387 | Basic (repression of DNA-binding) |
| 305-321 | Bipartite nuclear localization signal |
| 339-350 | Nuclear export signal |
| 370-372 | [KR]-[STA]-K motif |
| Metal | |

-continued

| Binding | |
|---|---|
| 176, 179, 238, 242 | Zinc binding |

| Allelic Variants | |
|---|---|
| Codon 248, 258, 245, 252 | Li-Fraumeni syndrome-1 |
| Codon 72 polymorphism | pro72-to-arg is caused by polymorphism rather than mutation, and is an indication for disease susceptibility, and apoptosis induction |
| Codon 249 | Cervical cancer |
| Codon 157 | Hepatocellular carcinoma |
| Codon 242 | Intracranial Ependymoma |
| N-terminal | MDM2 binding site |

-continued

| | |
|---|---|
| 80-94 | Proline rich domain important for the apoptotic activity |
| 316-325 | nuclear localization signaling domain |

TP53 Phenotypes

Disruption of the p53 pathway plays a role in cell cycle control, apoptosis, angiogenesis, carcinogenesis, and the phenotypes of various model organisms (and humans). Some p53 mutations result in partial loss of function or "knockdown" and others result in full loss of function mutations or "knockout".

The p53 activity resulting from a loss of function in one or several p53 effectors has completely different and variable phenotypes; some resulting in less severe tumor development or no tumor development. Complete loss of function or "knockout" of p53 resulting in loss of function in all of its effectors always results in early onset tumor development in known animal models.

TABLE

Phenotypes in p53 Mutations

| Mutation | | Phenotype |
|---|---|---|
| Complete loss of function, Knockout | The insertion creates a 450-base pair deletion; which corresponded to 106 nucleotides in exon 5 and 350 nucleotides in intron 4, in highly conserved domains | Early onset multiple primary neoplasms of different cell types Malignant lymphomas in thymus, heart, lung, spleen, liver, kidney, brain, haemangiosarcomas, osteosarcomas, and undifferentiated sarcomas |
| Complete loss of function, Knockout | Neo-resistant gene insertion replaced about 40% of p53 from exon 2 to intron 6 | Of the 49 homozygotes 46 died by six months. At least 41 had obvious tumors, and many had multiple tumors in various tissues. Tumor distribution of homozygotes included lymphoma, rhabdomyosarcoma, fibrosarcoma, anaplastic sarcoma, hemangiosarcoma, and teratoma |
| Complete loss of function, Knockout | A nonsense mutation resulting in substituting a premature stop codon for the Cysteine at position 273 in exon 7. | Homozygous rats develop a wide range of tumors including lymphoma, rhabdomyosarcoma, fibrosarcoma, anaplastic sarcoma, hemangiosarcoma, and teratoma. Heterozygous rats also develop tumors which display a loss of heterozygosity (LOH) similar to human cancers that arise from Tp53 mutations. |
| Partial loss of function, knockdown | A missense mutation resulting in substituting a Valine for the Glutamic acid at position 202 in exon 6. | Homozygous rats develop tumors in a more age dependent manner indicating a partial loss of Tp53 function. Heterozygous rats develop tumors that display a loss of heterozygosity (LOH) similar to human cancers that arise from Tp53 mutations. |
| Partial loss of function, knockdown | Serine to alanine at position 389 (S389A) amino acid exchange | sensitivity to UV-gamma radiation |

TABLE-continued

Phenotypes in p53 Mutations

| | Mutation | Phenotype |
|---|---|---|
| Partial loss of function, knockdown | Point mutations in two amino acid exchanges L25Q and W26S (p53QS) | Impaired DNA damage induced G1 cell cycle arrest activity, and it performed selective apoptosis, MDM2−/− p53+ exhibit embryonic lethality |

CLUSTAL 2.0.10 multiple sequence alignment of rat and mouse p53 amino acid sequence. The sequence alignment shows close homology between the mouse and rat p53 sequence. The homology of conserved domains and knowledge of insertion mutagenesis allows evidence that mutagenesis will create a total knockout rat p53.

```
rattus ---
MEDSQSDMSIELPLSQETFSCLWKLLPPDDILPTTATGSPNSMEDLFLPQDVAELLE           57
mus
MTAMEESQSDISLELPLSQETFSGLWKLLPPEDILP-----SPHCMDDLLLPQDVEEFFE        55
:**:*:********.***:  :.*::***  *:.* rattus
GPEEALQVSAPAAQEPGTEAPAPVAPASATPWPLSSSVPSQKTYQGNYGFHLGFLQSGT       116
mus
GPSEALRVSGAPAAQDPVTETPGPVAPAPATPWPLSSFVPSQKTYQGNYGFHLGFLQSGT      115
.*:.***:*.**:*.***.*** *************** * rattus
AKSVMCTYSISLNKLECQLAKTCPVQLWVTSTPPPGTRVRAMAIYKKSQHMTEVVRRCPH      176
mus
AKSVMCTYSPPLNKLFCQLAKTCPVQLWVSATPPAGSRVRAMAIYKKSQHMTEVVRRCPH      175
*******  .** *************:.*.*:************************ rattus
HERCSDGDGLAPPQHLIRVEGNPYAEYLDDRQTERHSVVVPYEPPEVGSDYTTIHYKYMC      236
mus
HERCSDGDGLAPPQHLIRVEGNLYPEYLEDRQTERHSVVVPYEPPEAGSEYTTIHYKYMC      235
********************** *.*:************..********** rattus
NSSCMGGMNRRPILTIITLEDSSGNLLGRDSFEVRVCACPGRDRRTEEENFRKKEEHCPE      296
mus
NSSCMGGMNRRPILTIITLEDSSGNLLGRDSFEVRVCACPGRDRRTEEENFRKKEVLCPE      295
**************************************************** * rattus
LPPGSAKRALPTSTSSSPQQKKKPLDGEYFTLKIRGRERFEMFRELNEALELKDARAAEE      356
mus
LPPGSAKRALPTCTSASPPQKKKPLDGEYFTLKIRGRKRFEMFRELNEALELKDAHATEE      355
************.**:**.*:************:****************:*:**

rattus
SGDSRAHSSYPKTKKGQSTSRHKKPMIKKVGPDSD                                391
mus
SGDSRAHSSYLKTKKGQSTSRHKKTMVKKVGPDSD                                390
**********.*************.*:********
``` p53 Knockout, Complete Loss of Function Phenotypes

Brandley et al. created a null p53 mouse model by using a targeting vector in murine embryonic stem cells which contain p53 with a PolII-neo expression cassette. The insertion created a 450-base pair deletion; which corresponded to 106 nucleotides in exon 5 and 350 nucleotides in intron 4. The deletion included p53 highly conserved regions.

The embryonic stem cells with the targeted p53 mutation were used to generate chimeric mice via microinjection into C57BL/6 blastocysts and implantation into pseudopregnant females. Cross-breading of heterozygotes produced 23% homozygous p53 null progeny; which appeared morphologically normal. This indicated that p53 function in not required for development.

The original heterozygotes, homozygotes for p53 null mutation and wild type mice were observed for spontaneous neoplasms. None of the 95 wild-type mice developed tumors or illness. By 9 months 2 of the 96 heterozygotes developed tumors. Of the 35 homozygous for p53 null mutation mice, 26 (74%) developed visible neoplasms by 6 months. The tumor onset was variable some appeared early; tumor development accelerated drastically between 15-25 weeks of age.

The tumors were found in a variety of cell types with no one cancer being dominant. Multiple primary neoplasms of different cell types and origin were observed. Malignant lymphomas in thymus, heart, lung, spleen, liver, kidney, brain were observed. Haemangiosarcomas, osteosarcomas, and undifferentiated sarcomas were present. (7)

In order to confirm that p53 is not required for normal mouse development and strongly dictates tumor occurrence and dispersion Jacks et al. created a p53 mutation which destroyed 40% coding capacity and completely eliminated synthesis of p53 protein.

A neomycin resistance gene was used to disrupt p53 from the targeting vector in D3 ES cells. The neo gene replaced about 40% of p53 from exon 2 to intron 6. The heterozygous ES cells were injected into C57BL/6 blastocysts; wild type, heterozygotes, and homozygote progeny were begot.

Development of homozygous p53−/− mice was normal. Of the heterozygotes 17% died at 17 months due to tumors that included: osteosarcoma, brain, lung adenocarcinoma, hair matrix tumor, hepatoma, lyomyosarcoma. They concluded that the heterozygotes exhibited loss of heterozygosity and were similar to the human disease Li-Fraumeni syndrome.

The homozygote p53 null mice were highly predisposed to malignancy and advanced rate of tumorigenesis compared to heterozygotes. Of the 49 homozygotes 46 died by six months. At least 41 had obvious tumors, and many had multiple tumors in various tissues. Tumor distribution of homozygotes included lymphoma, rhabdomyosarcoma, fibrosarcoma, anaplastic sarcoma, hemangiosarcoma, and teratoma. (8)

p53 Partial Loss of Function: Knockdown

Phosphorylation of p53 is an important regulation factor for its function. Upon UV irradiation mouse p53 serine at position 389 (S389) is phosphorylated and apoptosis is initiated. In order to study the impact of non-phosphorylated p53 on spontaneous and UV induced tumor onset Bruins et al. created serine to alanine point mutation at position 389 (S389A) mice. A targeting vector with a point mutation S389A on exon 11 of p53 was electroporated into J1 ES cells, heterozygotes (p53 A/+) were injected into blastocysts and then C57BL/6 mice to create heterozygous (p53 A/+) and homozygous (p53 S389A) lines. They studied the mice for differences in sensitivity to UV beta/gamma, p53 DNA binding activity, p53 activation of targeted genes, and spontaneous tumor development. p53 S389A mutant had at or near wild-type p53 activity except in sensitivity to UV-gamma radiation. WT cells rapidly accumulate p53 in response to UV-gamma, but p53(S389A) cells do not display p53 accumulation upon UV-gamma damage. There was no increase in spontaneous or induced tumor formation in p53 (S389A) mice. (11)

Transcriptional activation of p53 effector proteins is crucial to p53 functions of cell cycle arrest, apoptosis, and response to DNA damage. Johnson et al. created a knock-in ES model (as described) with point mutations in two amino acid exchanges L25Q and W26S (p53QS). The p53QS protein was able to activate Bax; it had impaired DNA damage induced G1 cell cycle arrest activity, and it performed selective apoptosis. The p53QS protein was completely unable to undergo apoptosis due to DNA damage, was partially deficient during serum deprivation, and had significant apoptosis when exposed to hypoxia. Also the point mutations disallow mdm2 to bind to p53QS. With the loss of this essential regulation element and p53 apoptosis still partially intact p53QS mice exhibit early embryonic lethality. (12)

p53 missense mutations are common in human cancers. Lui et al. created a p53 arginine to histidine amino acid mutation at position 172 of p53 via homologous recombination as described. This mutation also caused a deletion of the G-nucleotide at a splice joint. The p53(R172H) mice were susceptible to spontaneous tumors at a similar rate to p53+/− mice but not as severe as p53−/− mice. However, the p53 (R172H) mice exhibited a different tumor spectrum. Carcinomas were more frequent (29% vs 10%) and lymphomas were less frequent (16% vs 25%) in p53(R172H) vs p53+/− mice. Furthermore, loss of heterozygosity (LOH) was also less frequent in p53(R172H) tumors suggesting a p53 gain of function tumorigenesis allele. (13)

Cyclin dependent kinase inhibitor 2A (CDKN2A) encodes protein p14(ARF) which binds to p53 regulator; mouse double minute 2 (MDM2). p14(ARF) binds to MDM2 preventing it from inactivating p53. Mutations in CDKN2A (frequently in exon 1B) have manifested patients with melanomas; the CDKN2A mutations specifically inactivate p14 (ARF). The mutations described exhibit p53 importance in cell cycle control in melanoma.

Apoptic protease activating factor-1 (APAF-1) is a downstream effector of p53 conciliated apoptosis, and is inactivated in melanomas. (1)

CDKN2A targeted knockout mice which are null for ARF protein function have tumorigenesis phenotype and are animal models for melanoma. (2) Clinical studies have indicated that CDKN2A disruption is involved in patients with melanoma and various other neoplasms. (3)

MDM2 binds to p53 and targets its destruction.(4) MDM2 over-expression in common in sporadic melanomas. (5) However, when a mouse genetically modified model was created with a hypomorphic allele of MDM2 only certain components of p53 apoptosis were affected. This indicated that other regulators of p53 other that MDM2 determine its activity. Therefore, a hypermorphic MDM2 model would not have the exact phenotype as a p53 knockout model. (6) Clinical studies of patients with SNP 309 of MDM2 showed a higher level of MDM2 RNA and more constriction of p53. These patients showed accelerated tumor formation. (4)

By replacing the proline rich domain (PRD) in p53 Toledo et al. were able to determine that both MDM2 and MDM4 regulate p53 tumor suppressor activity. The PRD of p53 resides between residues 58-98 and contains five PXXP repeating motifs. They compared spontaneous tumor onset of p53 WT, p53−/−(KO), and p53 (−PRD) C57Bl/6 mice. p53WT mice did not form tumors, p53(−PRD) mice showed very few tumors at 12 months, and p53−/−(KO) mice all developed fatal tumors by 10 months.(9)

53BP1 is a conserved checkpoint protein which is specific the DNA double strand break repair. The protein binds to the central DNA binding domain of p53. The protein enhances p53 mediated transcription and is a substrate for ATM. Ward et al. used a targeting vector to replace 53BP1 exon spanning nucleotides 3777-4048 of mouse 53BP rendering the protein null. The vector was electroporated into 129/SvE ES cells, injected into C57BL/6 blastocysts and crossed to create 53BP−/− mice. The 53BP−/− mice showed slow growth, sensitivity to ionization, and cell cycle arrest deficiency. The mice did not develop tumors significantly compared to a p53 KO mouse. (10)

p53 phosphorylation site ser18 is important for transactivation of p53 effector proteins. Armata et al created a p53 (S18A) amino acid exchange mutant mouse model using techniques as described. The p53(S18A) mutant was unable to transactivate PUMA expression and apoptosis, but was able to function in DNA damage induced cell cycle arrest. p53(S18A) exhibited no early tumor onset; however, fibrosarcoma, leukemia, leiomyosarcoma, myxosarcoma tumors did form with similar onset and frequency to p53+/− mice. The mice also displayed aging associated phenotypes. (14)

Retinoblastoma 1 (Rb1) Domains and Loss of Function Mutations

Loss of function amino acid changes. In one example, a genetically modified rat is created with a disruption within one or more of the following loss of function nucleotide segments:

| Amino Acid | Region description |
| --- | --- |
| 373-771 | Binding pocket |
| 373-579 | Domain A |
| 580-639 | Spacer |
| 640-771 | Domain B |
| 763-928 | Interact with Limd1 |
| 771-928 | Domain C |
| 870-876 | Nuclear localization signal |
| 10-18 | Poly-A |
| 20-29 | Poly-Pro |

Wilms tumor 1 (WT1) domains and loss of function mutations

Loss of function mutations and amino acid changes. In one example, a genetically modified rat is created with a disruption within one or more of the following loss of function nucleotide segments:

| Amino Acid | Region description |
| --- | --- |
| 322-346 | Zinc finger domain |
| 352-376 | Zinc finger domain |
| 382-404 | Zinc finger domain |
| 413-437 | Zinc finger domain |
| 366-380 | DNA binding |
| 392-400 | DNA binding |
| 407-409 | KST motif |
| 27-82 | Proline rich |
| 423 | DNA binding |
| 429 | DNA binding |
| 368-457 | Transcriptional repressor |

Adenomatous Polyposis Coli (APC) Domains and Loss of Function Mutations

Loss of function mutations and amino acid changes. In one example, a genetically modified rat is created with a disruption within one or more of the following loss of function nucleotide segments

| Amino Acid | Region description |
| --- | --- |
| 451-493 | ARM-Armadillo/beta-catenin-like repeats |
| 503-545 | ARM-Armadillo/beta-catenin-like repeats |
| 546-589 | ARM-Armadillo/beta-catenin-like repeats |
| 590-636 | ARM-Armadillo/beta-catenin-like repeats |
| 637-681 | ARM-Armadillo/beta-catenin-like repeats |
| 682-723 | ARM-Armadillo/beta-catenin-like repeats |
| 724-765 | ARM-Armadillo/beta-catenin-like repeats |
| 1864-1891 | Highly charged region |
| 1-62 | Coil-coil |
| 125-260 | Coil-coil |
| 2802-2805 | Microtubule localization signal |
| 2840-2842 | PDZ binding |
| 1-728 | Leu-rich |
| 739-2931 | Ser-rich |
| 1130-1155 | Asp/Glu rich |
| 1556-1575 | Asp/Glu rich |
| 2670-2843 | EB1 binding domain |
| 157-208 | Suppressor APC domain |

Deleted in Colorectal Carcinoma (DCC) Domains and Loss of Function

Loss of function mutations and amino acid changes. In one example, a genetically modified rat is created with a disruption within one or more of the following loss of function nucleotide segments

| Amino Acid | Region description |
| --- | --- |
| 26-1097 | Extracellular domain |
| 1098-1122 | Transmembrane |
| 1123-1447 | Intracellular domain |
| 26-416 | Ig like domain |
| 429-1048 | Fibronectin domain |
| 1073-1445 | Neiogenin C-terminus |

Breast Cancer 1 (Brca1) Domains and Loss of Function

Loss of function mutations and amino acid changes. In one example, a genetically modified rat is created with a disruption within one or more of the following loss of function nucleotide segments

| Amino Acid | Region description |
| --- | --- |
| 1642-1736 | BRCT1 domain |
| 1756-1855 | BRCT2 domain |
| 24-65 | Zinc finger RING type domain |
| 18-236 | RAD18; RING-finger-containing E3 ubiquitin ligase |

Breast Cancer 2 (BRCA2) Domains and Loss of Function

Loss of function mutations and amino acid changes. In one example, a genetically modified rat is created with a disruption within one or more of the following loss of function nucleotide segments

| Amino Acid | Region description |
| --- | --- |
| 984-1018 | BRCA2 1 repeat |
| 1197-1231 | BRCA2 2 repeat |
| 1405-1439 | BRCA2 3 repeat |
| 1503-1537 | BRCA2 4 repeat |
| 1645-1669 | BRCA2 5 repeat |
| 1828-1845 | BRCA2 6 repeat |
| 1939-1973 | BRCA2 7 repeat |
| 1-40 | Interaction with PALB2 |
| 2313-2475 | Interaction with FANCD2 |

Phosphatase and Tensin Homolog (PTEN) Domains and Loss of Function

Loss of function mutations and amino acid changes. In one example, a genetically modified rat is created with a disruption within one or more of the following loss of function nucleotide segments

| Amino Acid | Region description |
| --- | --- |
| 14-185 | Phosphatase tensin type |
| 190-350 | C2 tensin type |
| 401-403 | PDZ binding domain |
| 188-349 | C2 domain of PTEN tumour-suppressor protein |

Von Hippel-Lindau Tumor Suppressor (VHL) Domains and Loss of Function

Loss of function mutations and amino acid changes. In one example, a genetically modified rat is created with a disruption within one or more of the following loss of function nucleotide segments

| Amino Acid | Region description |
| --- | --- |
| 123-132 | Interaction with Elongin BC complex |
| 14-53 | Repeat domains |
| 100-155 | Involved in binding to CCT complex |

Cyclin-Dependent Kinase Inhibitor 2A (Cdkn2a) Domains and Loss of Function

Loss of function mutations and amino acid changes. In one example, a genetically modified rat is created with a disruption within one or more of the following loss of function nucleotide segments

| Amino Acid | Region description |
| --- | --- |
| 11-40 | ANK 1 repeat |
| 44-72 | ANK 2 repeat |
| 77-106 | ANK 3 repeat |
| 110-135 | ANK 4 repeat |

Patched Homolog 1 (Ptch) Domains and Loss of Function

Loss of function mutations and amino acid changes. In one example, a genetically modified rat is created with a disruption within one or more of the following loss of function nucleotide segments

| Amino Acid | Region description |
| --- | --- |
| 1-1447 | Cytoplasmic, Transmembrane, Extracellular |
| 438-498 | SSD domain |
| 14-31 | Gly-rich |

Multiple Endocrine Neoplasia 1 (MEN1) Domains and Loss of Function

Loss of function mutations and amino acid changes. In one example, a genetically modified rat is created with a disruption within one or more of the following loss of function nucleotide segments

| Amino Acid | Region description |
| --- | --- |
| 219-395 | Interaction with FANCD2 |

Cadherin 1, Type 1, E-Cadherin (CDH1) Domains and Loss of Function.

Loss of function mutations and amino acid changes. In one example, a genetically modified rat is created with a disruption within one or more of the following loss of function nucleotide segments

| Amino Acid | Region description |
| --- | --- |
| 24-713 | Extracellular |
| 714-734 | Transmembrane |
| 735-886 | Cytoplasmic |
| 159-266 | Cadherin 1 |
| 267-379 | Cadherin 2 |
| 380-490 | Cadherin 3 |
| 491-597 | Cadherin 4 |
| 598-701 | Cadherin 5 |
| 762-773 | Required for binding CTNND1 and PSEN1 |
| 815-886 | Required for binding alpha, beta |
| 842-857 | Ser-rich |

MutL Homolog 1, Colon Cancer, Nonpolyposis Type 2 (MLH1)

Loss of function mutations and amino acid changes. In one example, a genetically modified rat is created with a disruption within one or more of the following loss of function nucleotide segments

| Amino Acid | Region description |
| --- | --- |
| 410-650 | Interaction with EXO1 |
| 211-335 | Tranducer domain |
| 31-124 | HTPase domain |

MutS Homolog 2, Colon Cancer, Nonpolyposis Type 1 (MSH2) Loss of Function and Domains Loss of function mutations and amino acid changes. In one example, a genetically modified rat is created with a disruption within one or more of the following loss of function nucleotide segments

| Amino Acid | Region description |
| --- | --- |
| 669-676 | ATP nucleotide binding region |
| 601-671 | Interaction with EXO1 |
| 663-853 | ABC_MSH2 |
| 18-132 | MutS1 domain |
| 158-284 | MutS II domain |
| 297-612 | MutS II domain |

Serine/Threonine Kinase 11 (STK11) Domains and Loss of Function

Loss of function mutations and amino acid changes. In one example, a genetically modified rat is created with a disruption within one or more of the following loss of function nucleotide segments

| Amino Acid | Region description |
| --- | --- |
| 49-309 | Protein kinase catalytic domain |
| 55-63 | ATP nucleotide binding |

SMAD Family Member 4 (SMAD4) Domains and Loss of Function

Loss of function mutations and amino acid changes. In one example, a genetically modified rat is created with a disruption within one or more of the following loss of function nucleotide segments

| Amino Acid | Region description |
| --- | --- |
| 18-142 | MH1 small DNA binding domain |
| 323-552 | MH2 C terminal domain |
| 275-320 | SAD |
| 451-466 | Poly-Ala |

Tuberous Sclerosis 1 (TSC1) Domains and Loss of Function

Loss of function mutations and amino acid changes. In one example, a genetically modified rat is created with a disruption within one or more of the following loss of function nucleotide segments

| Amino Acid | Region description |
| --- | --- |
| 721-919 | Coiled-coil |
| 970-994 | Coiled-coil |
| 1038-1043 | Poly-Ser |

Tuberous Sclerosis 2 (TSC2) Domains and Loss of Function

Loss of function mutations and amino acid changes. In one example, a genetically modified rat is created with a disruption within one or more of the following loss of function nucleotide segments

| Amino Acid | Region description |
| --- | --- |
| 1533-1760 | Rap-GAP |
| 557-904 | Tuberin domain |

Neurofibromin 1 (NF1) Domains and Loss of Function

Loss of function mutations and amino acid changes. In one example, a genetically modified rat is created with a disruption within one or more of the following loss of function nucleotide segments

| Amino Acid | Region description |
| --- | --- |
| 1237-1432 | Ras-GAP domain |
| 1561-1790 | CRAL-TRIO domain |
| 1354-1357 | Poly-Ser region |
| 1560-1706 | Lipid binding domain |

Neurofibromin 2 (NF2) Domains and Loss of Function

Loss of function mutations and amino acid changes. In one example, a genetically modified rat is created with a disruption within one or more of the following loss of function nucleotide segments

| Amino Acid | Region description |
| --- | --- |
| 22-311 | FERM domain |
| 327-465 | Glu-rich region |

Additional specific loss of function mutations. In one example, a genetically modified rat is created with a mutation within one or more of the following tumor suppressor genes.

| Tumor Suppressor Gene | Mutation Type | Location |
| --- | --- | --- |
| Brinp3 | Transposon gene trap insertion | Intron 7 |
| Dcc | Transposon gene trap insertion | Intron 1 |
| ErbB4 | Transposon gene trap insertion | Intron 2 |
| Snx25 | Transposon gene trap insertion | Intron 5 |
| Pebp4 | Transposon gene trap insertion | Intron 2 |
| Robo1 | Transposon gene trap insertion | Intron 2 |
| Spata13 | Transposon gene trap insertion | Intron 2 |
| Abcc1 | Amino acid change | L852Q |
| Abcg2 | Amino acid change | E59X, D65G |
| Cadm3 | Amino acid change | I93F, T300M |
| Ccr4 | Amino acid change | W198X |
| CyP2B2 | Amino acid change | D337V |
| Dicer1 | Amino acid change | I1593N |
| Fbxo10 | Amino acid change | V34G |
| Fzd6 | Amino acid change | T339A, D170V |
| Fzd7 | Amino acid change | I433T, E308G |
| Gpr124 | Amino acid change | I924F |
| Gpr87 | Amino acid change | P46L, R255C |
| Gprc5d | Amino acid change | I38T |
| I18rb | Amino acid change | N267I, C307X, H305Q |
| Oxgr1 | Amino acid change | N294K |
| Piwil2 | Amino acid change | V619A |
| Pparg | Amino acid change | V483M |
| Ptger2 | Amino acid change | E106K |
| Ptpn13 | Amino acid change | G1865R |
| Rara | Amino acid change | S414P, V309D, S327G |
| Smo | Amino acid change | L357P |
| Sstr2 | Amino acid change | V64D |
| Sstr5 | Amino acid change | V226A |
| Trpm5 | Amino acid change | M570K |
| Xrcc5 | Amino acid change | S266P |
| Xrcc6 | Amino acid change | N279D |

Examples

The rat and progenies thereof of the present invention may be any rat or progenies thereof, so long as they are a rat or progenies thereof in which genome is modified so as to have decreased or deleted activity of the tumor suppressor gene.

Gene Disruption Technique which Targets at a Gene Encoding Robo1 and p53

The gene disruption method may be any method, so long as it can disrupt the gene of the target enzyme. Examples include a homologous recombination method, a method using retrovirus, a method using transposon, and the like.

(a) Preparation of the Rat and Progenies thereof of the Present Invention by Homologous Recombination The rat and the progenies thereof of the present invention can be produced by modifying a target gene on chromosome through a homologous recombination technique which targets at a gene encoding the tumor suppressor gene. The target gene on chromosome can be modified by using a method described in Gene Targeting, A Practical Approach, IRL Press at Oxford University Press (1993) (hereinafter referred to as "Gene Targeting, A Practical Approach"); or the like, for example.

Based on the nucleotide sequence of the genomic DNA, a target vector is prepared for homologous recombination of a target gene to be modified (e.g., structural gene of the tumor suppressor gene, or a promoter gene). The prepared target vector is introduced into an embryonic stem cell and a cell in which homologous recombination occurred between the target gene and target vector is selected.

The selected embryonic stem cell is introduced into a fertilized egg according to a known injection chimera method or aggregation chimera method, and the embryonic stem cell-introduced fertilized egg is transplanted into an oviduct or uterus of a pseudopregnant female rat to thereby select germ line chimeras.

The selected germ line chimeras are crossed, and individuals having a chromosome into which the introduced target vector is integrated by homologous recombination with a gene region on the genome which encodes the tumor suppressor protein are selected from the born offspring.

The selected individuals are crossed, and homozygotes having a chromosome into which the introduced target vector is integrated by homologous recombination with a gene region on the genome which encodes the tumor suppressor protein in both homologous chromosomes are selected from the born offspring. The obtained homozygotes are crossed to obtain offspring to thereby prepare the rat and progenies thereof of the present invention.

(b) Preparation of the Rat and Progenies thereof of the Present Invention by a Method Using a Transposon The rat and progenies thereof of the present invention can be prepared by using a transposon system similar to that described in Nature Genet., 25, 35 (2000) or the like, and then by selecting a mutant of the tumor suppressor gene.

The transposon system is a system in which a mutation is induced by randomly inserting an exogenous gene, such as a gene trap, into chromosome, wherein an exogenous gene interposed between transposons is generally used as a vector for inducing a mutation, and a transposase expression vector for randomly inserting the gene into the chromosome is introduced into the cell at the same time. Any transposase can be used, so long as it is suitable for the sequence of the transposon to be used. As the exogenous gene, any gene can be used, so long as it can induce a mutation in the DNA of the cell.

The rat and progenies thereof of the present invention can be prepared by introducing a mutation into a gene encoding the tumor suppressor gene, and then by selecting a rat of interest in which the DNA is mutated.

Specifically, the method includes a method in which a rat of interest in which the mutation occurred in the gene encoding the Robo1 or p53 protein is selected from mutants born from generative cells which are subjected to mutation-inducing treatment or spontaneously generated mutants. In another embodiment, the tumor-suppressor gene is one of several known tumor-suppressor genes, such as (Abcb4, Abcc1, Abcg2, Actb, Ahr, Akt, Akt1, Akt2, Akt3, Amhr2, Anxa7, Apc, Ar, Atm, Axin2, B2m, Bard1, Bcl2l1, Becn1, Bhlha15, Bin1, Blm, Braf, Brca1, Brca2, Brca3, Braf, Brcata, Brinp3, Brip1, Bub1b, Bwscr1a, Cadm3, Casc1, Casp3, Casp7, Casp8, Cav1, Ccnd1, Ccr4, Ccs1, Cd28, Cdc25a, Cd95, Cdh1, Cdkn1a, Cdkn1b, Cdkn2a, Cdkn1b, Cdkn2c, Chek1, Chek2, Crcs1, Crcs10, Crcs11, Crcs2, Crcs3, Crcs4, Crcs5, Crcs6, Crcs7, Crcs8, Crcs9, Ctnnb1, Cyp1a1, Cyp2a6, Cyp2b2, Dcc, Dkc1, Dicer1, Dmtf1, Dnmt1, E2f1, Eaf2, Eef1a1, Egfr, Egfr4, Erbb2, Erbb4, Ercc2, Ercc6, Ercc8, Errfi1, Esr1, Etv4, Faslg, Fbxo10, Fgfr3, Fntb, Foxm1, Foxn1, Fzd6, Fzd7, Fzr1, Gadd45a, Gast, Gnai2, Gpc1, Gpr124, Gpr87, Gprc5a, Gprc5d, Grb2, Gstm1, Gstm5, Gstp1, Gstt1, H19, H2afx, Hck, Lims1, Hdac, Hic1, Hmmr, Hnpcc8, Hprt, Hras, Htatip2, Il1b, Il10, Il12, Il6, Il8rb Inha, Itgav, Jun, Jak3, Kit, Klf4, Kras, Kras2, Lig1, Lig4, Lkb1, Lmo7, Lncr1, Lncr2, Lncr3, Lncr4, Ltbp4, Lyz2, Lzts1, Mad1l1, Mad2l1, Mapk14, Mcc, Mcm4, Men1, Met, Mgat5, Mif, Mlh1, Mlh3, Mmp8, Mnt, Mpo, Msh2, Msh3, Msh6, Msmb, Mthfr, Mutyh, Myh11, Nat2, Nbn, Ncoa3, Neil1, Nf1, Nf2, Nfe211, Nhej1, Nkx2-1, Nkx2-9, Nkx3-1, Nqo1, Nras, Nudt1, Ogg1, Oxgr1, Palb2, Park2, Pggt1b, Pgr, Pi3k, Pik3ca, Piwil2, Pla2g2a, Plg, Plk3, Pms1, Pms2, Pold1, Pole, Ppard, Pparg, Ppfia2, Ppm1d, Prdm2, Prdx1, Prkar1a, Ptch, Pten, Prom1, Psca, Ptch1, Ptf1a, Ptger2, Ptpn13, Ptprj, Rara, Rad51, Rassf1, Rb, Rb1, Rb1cc1, Rb12, Recgl4, Ret, Rgs5, Rhoc, Rint1, Robo1, Rpl38, S100a4, Smad4, Smarcb1, Smo, Snx25, Spata13, Srpx, Ssic1, Sstr2, Sstr5, Stat3, St5, St7, St14, Stk11, Suds3, Tap1, Tbx21, Terc, Tnf, Tp53, Trpm5, Tsc2, Tsc1, Vhl, Wt1, Wt2, Xrcc1, Xrcc5, and Xrcc6). The generative cell includes cells capable of forming an individual such as a sperm, an ovum or pluripotent cells. The generative cell may also be a rat somatic cells.

Examples in which several methods which are described have been employed by the inventors to create the invented cancer model phenotype in Rattus norvegicus are described below.

Genetic modification of Rattus norvegicus tumor suppressor gene Roundabout, axon guidance receptor, homolog 1 (Robo1) was carried out by a DNA transposon insertional mutagenesis method similar to that described in Nature Genet., 25, 35 (2000). The DNA transposon-mediated genetically modified allele was designated Robo1Tn(sb-T2/Bart3) 2.327Mcwi. The mutant strain symbol for the tumor suppressor rat was designated F344-Robo1Tn(sb-T2/Bart3) 2.327Mcwi. The DNA transposon insertion occurred on chromosome 11; within intron 2 of the Robo1 gene in the rat's genome. The sequence tag map position was between base pairs 11280254-11280285. The sequence tag was:

TACATACACTGGGCACTGGGTTTGACAACTAG

Thus, a DNA transposon was inserted into the rat Robo1 gene rendering the gene completely inactive. Robo1−/− Knockout (KO) rats display bronchial epithelial abnormalities associated with early lung cancer compared to wild type (WT) rats. Robo1−/−KO rats had an increased tumorigenesis rate when compared to WT rats. Therefore, the DNA insertional mutagenesis method has produced an example of a genetically modified tumor suppressor rat model.

Genetic modification of Rattus norvegicus tumor suppressor gene tumor protein p53 (p53, TRP53; MGC112612; TP53) was carried out using DNA transposon insertional mutagenesis method similar to that described in Nature Genet., 25, 35 (2000). The DNA transposon-mediated genetically modified allele was designated TP53Tn(sb-T2/Bart3) 1.56Mcwi. The mutant strain symbol for the tumor suppressor rat was designated F344-TP53Tn(sb-T2/Bart3) 1.56Mcwi. The DNA transposon insertion occurred on chromosome 10; within intron 1 of the TP53 gene in the rat's genome.

The phenotype of p53−/− knockout (KO) rats (earlier described) is the spontaneous tumor growth. In p53−/−KO rats tumorigenesis and malignant transformation occurs at a substantially increased rate when compared to wild type (WT) rats. Obvious tumors occur in all homozygous animals, and have multiple tumors in various tissues. Tumor distribution of homozygotes included but is not limited to lymphoma, rhabdomyosarcoma, fibrosarcoma, anaplastic sarcoma, hemangiosarcoma, and teratoma. Therefore, the transposon-mediated p53−/−KO rat has produced an example of a genetically modified tumor suppressor rat model.

The practice of the present invention will employ, unless otherwise indicated, conventional techniques of molecular biology (including recombinant techniques), microbiology, cell biology and biochemistry, which are within the skill of the art.

The invention claimed is:

1. A genetically modified rat, or progeny of the rat, wherein the rat or its progeny comprise in at least some of its cells a genome comprising a disruption of one or more tumor suppressor genes that results in a misexpression of the one or more tumor suppressor genes, wherein the rat or its progeny exhibits a cancer phenotype.

2. The genetically modified rat of claim 1, wherein said one or more tumor suppressor genes are conditionally misexpressed.

3. The genetically modified rat of claim 1, wherein the misexpression results in decreased expression of said one or more tumor suppressor genes.

4. The genetically modified rat of claim 1, wherein the cells are pluripotent cells.

5. The genetically modified rat of claim 1, wherein the cells are somatic cells.

6. The genetically modified rat of claim 1, wherein the one or more tumor suppressor genes are disrupted by removal of DNA encoding all or part of the tumor suppressor protein.

7. The genetically modified rat of claim 1, wherein the one or more tumor suppressor genes are disrupted by insertion mutation.

8. The genetically modified rat of claim 1, wherein the one or more tumor suppressor genes are disrupted by transposon insertion mutation.

9. The genetically modified rat of claim 1, wherein the one or more tumor suppressor genes are disrupted by deletion mutation.

10. The genetically modified rat of claim 1, wherein the one or more tumor suppressor genes are disrupted by the introduction of a cassette or gene trap by recombination.

11. The genetically modified rat of claim 1, wherein the genetically modified rat is homozygous for the one or more disrupted genes.

12. The genetically modified rat of claim 1, wherein the genetically modified rat is heterozygous for the one or more disrupted genes.

13. The genetically engineered rat of claim 1, wherein the tumor suppressor gene is selected from the group consisting of Abcb4, Abcc1, Abcg2, Actb, Ahr, Akt, Akt1, Akt2, Akt3, Amhr2, Anxa7, Apc, Ar, Atm, Axin2, B2m, Bard1, Bcl2l1, Becn1, Bhlha15, Bin1, Blm, Braf, Brca1, Brca2, Brca3, Braf, Brcata, Brinp3, Brip1, Bub1b, Bwscr1a, Cadm3, Casc1, Casp3, Casp7, Casp8, Cav1, Ccnd1, Ccr4, Ccs1, Cd28, Cdc25a, Cd95, Cdh1, Cdkn1a, Cdkn1b, Cdkn2a, Cdkn2b, Cdkn2c, Chek1, Chek2, Crcs1, Crcs10, Crcs11, Crcs2, Crcs3, Crcs4, Crcs5, Crcs6, Crcs7, Crcs8, Crcs9, Ctnnb1, Cyp1a1, Cyp2a6, Cyp2b2, Dcc, Dkc1, Dicer1, Dmtf1, Dnmt1, E2f1, Eaf2, Eef1a1, Egfr, Egfr4, Erbb2, Erbb4, Ercc2, Ercc6, Ercc8, Errfi1, Esr1, Etv4, Faslg, Fbxo10, Fgfr3, Fntb, Foxm1, Foxn1, Fzd6, Fzd7, Fzr1, Gadd45a, Gast, Gnai2, Gpc1, Gpr124, Gpr87, Gprc5a, Gprc5d, Grb2, Gstm1, Gstm5, Gstp1, Gstt1, H19, H2afx, Hck, Lims1, Hdac, Hic1, Hmmr, Hnpcc8, Hprt, Hras, Htatip2, Il1b, Il10, Il2, Il6, Il8rb Inha, Itgav, Jun, Jak3, Kit, Klf4, Kras, Kras2, Lig1, Lig4, Lkb1, Lmo7, Lncr1, Lncr2, Lncr3, Lncr4, Ltbp4, Lyz2, Lzts1, Mad1ll1, Mad2l1, Mapk14, Mcc, Mcm4, Men1, Met, Mgat5, Mif, Mlh1, Mlh3, Mmp8, Mnt, Mpo, Msh2, Msh3, Msh6, Msmb, Mthfr, Mutyh, Myh11, Nat2, Nbn, Ncoa3, Neil1, Nf1, Nf2, Nfe2l1, Nhej1, Nkx2-1, Nkx2-9, Nkx3-1, Nqo1, Nras, Nudt1, Ogg1, Oxgr1, Palb2, Park2, Pggt1b, Pgr, Pi3k, Pik3ca, Piwil2, Pla2g2a, Plg, Plk3, Pms1, Pms2, Pold1, Pole, Ppard, Pparg, Ppfia2, Ppm1d, Prdm2, Prdx1, Prkar1a, Ptch, Pten, Prom1, Psca, Ptch1, Ptf1a, Ptger2, Ptpn13, Ptprj, Rara, Rad51, Rassf1, Rb, Rb1, Rb1cc1, Rbl2, Recgl4, Ret, Rgs5, Rhoc, Rint1, Robo1, Rpl38, S100a4, Smad4, Smarcb1, Smo, Snx25, Spata13, Srpx, Ssic1, Sstr2, Sstr5, Stat3, St5, St7, St14, Stk11, Suds3, Tap1, Tbx21, Terc, Tnf Tp53, Trpm5, Tsc2, Tsc1, Vhl, Wt1, Wt2, Xrcc1, Xrcc5, and Xrcc6.

14. The genetically engineered rat of claim 1, wherein the tumor suppressor gene is selected from the group consisting of Casp7, Dcc, and p53.

15. A genetically engineered rat, or progeny of the rat, wherein the rat or its progeny comprise in at least some of its cells a genome comprising a disruption of one or more tumor suppressor genes that results in the rat or its progeny exhibiting a cancer phenotype.

16. The genetically modified rat of claim 15, wherein the one or more tumor suppressor genes are disrupted by deletion mutation.

17. The genetically modified rat of claim 15, wherein the one or more tumor suppressor genes are disrupted by the introduction of a cassette or gene trap by recombination.

18. The genetically engineered rat of claim 15 wherein the disruption causes the rat to have a greater susceptibility to cancer.

19. The genetically engineered rat of claim 15, wherein the disruption causes a complete loss-of-function phenotype.

20. The genetically engineered rat of claim 15, wherein the disruption causes a partial loss-of-function phenotype.

21. The genetically engineered rat of claim 15 wherein the tumor suppressor gene is selected from the group consisting of Abcb4, Abcc1, Abcg2, Actb, Ahr, Akt, Akt1, Akt2, Akt3, Amhr2, Anxa7, Apc, Ar, Atm, Axin2, B2m, Bard1, Bcl2l1, Becn1, Bhlha15, Bin1, Blm, Braf, Brca1, Brca2, Brca3, Braf, Brcata, Brinp3, Brip1, Bub1b, Bwscr1a, Cadm3, Casc1, Casp3, Casp7, Casp8, Cav1, Ccnd1, Ccr4, Ccs1, Cd28, Cdc25a, Cd95, Cdh1, Cdkn1a, Cdkn1b, Cdkn2a, Cdkn2b, Cdkn2c, Chek1, Chek2, Crcs1, Crcs10, Crcs11, Crcs2, Crcs3, Crcs4, Crcs5, Crcs6, Crcs7, Crcs8, Crcs9, Ctnnb1, Cyp1a1, Cyp2a6, Cyp2b2, Dcc, Dkc1, Dicer1, Dmtf1, Dnmt1, E2f1, Eaf2, Eef1a1, Egfr, Egfr4, Erbb2, Erbb4, Ercc2, Ercc6, Ercc8, Errfi1, Esr1, Etv4, Faslg, Fbxo10, Fgfr3, Fntb, Foxm1, Foxn1, Fzd6, Fzd7, Fzr1, Gadd45a, Gast, Gnai2, Gpc1, Gpr124, Gpr87, Gprc5a, Gprc5d, Grb2, Gstm1, Gstm5, Gstp1, Gstt1, H19, H2afx, Hck, Lims1, Hdac, Hic1, Hmmr, Hnpcc8, Hprt, Hras, Htatip2, Il1b, Il10, Il2, Il6, Il8rb Inha, Itgav, Jun, Jak3, Kit, Klf4, Kras, Kras2, Lig1, Lig4, Lkb1, Lmo7, Lncr1, Lncr2, Lncr3, Lncr4, Ltbp4, Lyz2, Lzts1, Mad1ll1, Mad2l1, Mapk14, Mcc, Mcm4, Men1, Met, Mgat5, Mif, Mlh1, Mlh3, Mmp8, Mnt, Mpo, Msh2, Msh3, Msh6, Msmb, Mthfr, Mutyh, Myh11, Nat2, Nbn, Ncoa3, Neil1, Nf1, Nf2, Nfe2l1, Nhej1, Nkx2-1, Nkx2-9, Nkx3-1, Nqo1, Nras, Nudt1, Ogg1, Oxgr1, Palb2, Park2, Pggt1b, Pgr, Pi3k, Pik3ca, Piwil2, Pla2g2a, Plg, Plk3, Pms1, Pms2, Pold1, Pole, Ppard, Pparg, Ppfia2, Ppm1d, Prdm2, Prdx1, Prkar1a, Ptch, Pten, Prom1, Psca, Ptch1, Ptf1a, Ptger2, Ptpn13, Ptprj, Rara, Rad51, Rassf1, Rb, Rb1, Rb1cc1, Rbl2, Recgl4, Ret, Rgs5, Rhoc, Rint1, Robo1, Rpl38, S100a4, Smad4, Smarcb1, Smo, Snx25, Spata13, Srpx, Ssic1, Sstr2, Sstr5, Stat3, St5, St7, St14, Stk11, Suds3, Tap1, Tbx21, Terc, Tnf, Tp53, Trpm5, Tsc2, Tsc1, Vhl, Wt1, Wt2, Xrcc1, Xrcc5, and Xrcc6.

22. The genetically engineered rat of claim 15, wherein the tumor suppressor gene is selected from the group consisting of Casp7, Dcc, and p53.

23. The genetically engineered rat of claim 15, wherein the one or more tumor suppressor genes are disrupted by transposon insertion mutations.

24. The genetically modified rat of claim 15, wherein the rat is homozygous for the one or more disrupted genes.

25. The genetically modified rat of claim 15, wherein the rat is heterozygous for the one or more disrupted genes.

26. A screening method for identifying a compound useful for treating a hyperproliferative condition, comprising
  (a) providing an assay system comprising a model system comprising a genetically modified rat or progeny of the rat, wherein the rat or its progeny comprise in at least some its cells a genome comprising a disruption of one or more tumor suppressor genes, wherein the rat or its progeny exhibits a cancer phenotype;
  (b) contacting the model system with a candidate test agent; and
  (c) detecting a phenotypic change in the model system that indicates that the tumor suppressor function is restored when compared relative to wild-type cells.

27. The screening method of claim 26, wherein the one or more tumor suppressor genes are disrupted by removal of DNA encoding all or part of the tumor suppressor protein.

28. The screening method of claim 26, wherein the one or more tumor suppressor genes are disrupted by transposon insertion mutations.

29. The screening method of claim 26, wherein the one or more tumor suppressor genes are disrupted by deletion mutation.

30. The screening method of claim 26, wherein the one or more tumor suppressor genes are disrupted by the introduction of a cassette or gene trap by recombination.

31. The screening method of claim 26, wherein the tumor suppressor gene is selected from the group consisting of Abcb4, Abcc1, Abcg2, Actb, Ahr, Akt, Akt1, Akt2, Akt3, Amhr2, Anxa7, Apc, Ar, Atm, Axin2, B2m, Bard1, Bcl2l1, Becn1, Bhlhal5, Bin1, Blm, Braf, Brca1, Brca2, Brca3, Braf, Brcata, Brinp3, Brip1, Bub1b, Bwscr1a, Cadm3, Casc1, Casp3, Casp7, Casp8, Cav1, Ccnd1, Ccr4, Ccs1, Cd28, Cdc25a, Cd95, Cdh1, Cdkn1a, Cdkn1b, Cdkn2a, Cdkn2b, Cdkn2c, Chek1, Chek2, Crcs1, Crcs10, Crcs11, Crcs2, Crcs3, Crcs4, Crcs5, Crcs6, Crcs7, Crcs8, Crcs9, Ctnnb1, Cyp1a1, Cyp2a6, Cyp2b2, Dcc, Dkc1, Dicer1, Dmtf1, Dnmt1, E2f1, Eaf2, Eef1a1, Egfr, Egfr4, Erbb2, Erbb4, Ercc2, Ercc6, Ercc8, Errfi1, Esr1, Etv4, Faslg, Fbxo10, Fgfr3, Fntb, Foxm1, Foxn1, Fzd6, Fzd7, Fzr1, Gadd45a, Gast, Gnai2, Gpc1, Gpr124, Gpr87, Gprc5a, Gprc5d, Grb2, Gstm1, Gstm5, Gstp1, Gstt1, H19, H2afx, Hck, Lims1, Hdac, Hic1, Hmmr, Hnpcc8, Hprt, Hras, Htatip2, Il1b, Il10, Il2, Il6, Il8rb Inha, Itgav, Jun, Jak3, Kit, Klf4, Kras, Kras2, Lig1, Lig4, Lkb1, Lmo7, Lncr1, Lncr2, Lncr3, Lncr4, Ltbp4, Lyz2, Lzts1, Mad1l1, Mad2l1, Mapk14, Mcc, Mcm4, Men1, Met, Mgat5, Mif, Mlh1, Mlh3, Mmp8, Mnt, Mpo, Msh2, Msh3, Msh6, Msmb, Mthfr, Mutyh, Myh11, Nat2, Nbn, Ncoa3, Neil1, Nf1, Nf2, Nfe2l1, Nhej1, Nkx2-1, Nkx2-9, Nkx3-1, Nqo1, Nras, Nudt1, Ogg1, Oxgr1, Palb2, Park2, Pggt1b, Pgr, Pi3k, Pik3ca, Piwil2, Pla2g2a, Plg, Plk3, Pms1, Pms2, Pold1, Pole, Ppard, Pparg, Ppfia2, Ppm1d, Prdm2, Prdx1, Prkar1a, Ptch, Pten, Prom1, Psca, Ptch1, Ptf1a, Ptger2, Ptpn13, Ptprj, Rara, Rad51, Rassf1, Rb, Rb1, Rb1cc1, Rb12, Recgl4, Ret, Rgs5, Rhoc, Rint1, Robo1, Rpl38, S100a4, Smad4, Smarcb1, Smo, Snx25, Spata13, Srpx, Ssic1, Sstr2, Sstr5, Stat3, St5, St7, St14, Stk11, Suds3, Tap1, Tbx21, Terc, Tnf, Tp53, Trpm5, Tsc2, Tsc1, Vhl, Wt1, Wt2, Xrcc1, Xrcc5, and Xrcc6.

32. The screening method of claim 26, wherein the tumor suppressor gene is selected from the group consisting of Casp7, Dcc, and p53.

33. A screening method for identifying a compound useful for treating a hyperproliferative condition, comprising (a) providing an assay system comprising a model system comprising a genetically engineered rat or progeny of the rat, wherein the rat or its progeny comprise in at least some of its cells a genome comprising a disruption of one or more tumor suppressor gene that causes a cancer phenotype in said genetically modified rat;
  (b) contacting the model system with a candidate test agent; and
  (c) detecting a change in tumor suppressor polypeptide expression or activity between the presence and absence of the candidate test agent indicates the presence of a candidate modulating agent.

34. The screening method of claim 33 wherein said cancer is selected from haemangiosarcomas, osteosarcomas, undifferentiated sarcomas, rhabdomyosarcoma, fibrosarcoma, anaplastic sarcoma, or a combination thereof.

* * * * *

UNITED STATES PATENT AND TRADEMARK OFFICE
CERTIFICATE OF CORRECTION

PATENT NO. : 8,722,964 B2  
APPLICATION NO. : 12/766284  
DATED : May 13, 2014  
INVENTOR(S) : Eric M. Ostertag et al.

Page 1 of 2

It is certified that error appears in the above-identified patent and that said Letters Patent is hereby corrected as shown below:

In the Claims

Claim 1, Column 65, line 2, reads "...genetically modified rat..."; which should be deleted and replaced with "...genetically engineered rat...."

Claim 2, Column 65, line 8, reads "...genetically modified rat..."; which should be deleted and replaced with "...genetically engineered rat...."

Claim 3, Column 65, line 11, reads "...genetically modified rat..."; which should be deleted and replaced with "...genetically engineered rat...."

Claim 4, Column 65, line 14, reads "...genetically modified rat..."; which should be deleted and replaced with "...genetically engineered rat...."

Claim 5, Column 65, line 16, reads "...genetically modified rat..."; which should be deleted and replaced with "...genetically engineered rat...."

Claim 6, Column 65, line 18, reads "...genetically modified rat..."; which should be deleted and replaced with "...genetically engineered rat...."

Claim 7, Column 65, line 21, reads "...genetically modified rat..."; which should be deleted and replaced with "...genetically engineered rat...."

Claim 8, Column 65, line 24, reads "...genetically modified rat..."; which should be deleted and replaced with "...genetically engineered rat...."

Claim 9, Column 65, line 27, reads "...genetically modified rat..."; which should be deleted and replaced with "...genetically engineered rat...."

Signed and Sealed this  
Fifth Day of August, 2014

Michelle K. Lee  
*Deputy Director of the United States Patent and Trademark Office*

Claim 10, Column 65, line 30, reads "...genetically modified rat..."; which should be deleted and replaced with "...genetically engineered rat...."

Claim 11, Column 65, line 33, reads "...genetically modified rat..."; which should be deleted and replaced with "...genetically engineered rat...."

Claim 12, Column 65, line 36, reads "...genetically modified rat..."; which should be deleted and replaced with "...genetically engineered rat...."

Claim 13, Column 65, line 58, reads "...Mad1ll1..."; which should be deleted and replaced with "...Mad1l1...."

Claim 16, Column 66, line 13, reads "...genetically modified rat..."; which should be deleted and replaced with "...genetically engineered rat...."

Claim 17, Column 66, line 16, reads "...genetically modified rat..."; which should be deleted and replaced with "...genetically engineered rat...."

Claim 21, Column 66, line 42, reads "...Il8rb Inha..."; which should be deleted and replaced with "...Il8rb, Inha...."

Claim 24, Column 66, line 64, reads "...genetically modified rat..."; which should be deleted and replaced with "...genetically engineered rat...."

Claim 25, Column 66, line 66, reads "...genetically modified rat..."; which should be deleted and replaced with "...genetically engineered rat...."

Claim 26, Column 67, line 4, reads "...genetically modified rat..."; which should be deleted and replaced with "...genetically engineered rat...."

Claim 31, Column 67, line 30, reads "...Braf, Brca1, Brca2, Brca3, Braf, Brcata..."; which should be deleted and replaced with "...Braf, Brca1, Brca2, Brca3, Brcata...."

Claim 33, Column 68, line 27, reads "...gene..."; which should be deleted and replaced with "...genes...."

Claim 33, Column 68, line 28, reads "...genetically modified rat..."; which should be deleted and replaced with "...genetically engineered rat...."